(12) United States Patent
Hruska et al.

(10) Patent No.: US 8,741,840 B2
(45) Date of Patent: Jun. 3, 2014

(54) BMP-7 FOR USE IN TREATING NEOINTIMAL HYPERPLASIA

(75) Inventors: Keith Hruska, Creve Coeur, MO (US); Eric T. Choi, St. Louis, MO (US)

(73) Assignee: Washington University, St. Louis, MO (US)

( * ) Notice: Subject to any disclaimer, the term of this patent is extended or adjusted under 35 U.S.C. 154(b) by 46 days.

(21) Appl. No.: 12/867,562

(22) PCT Filed: Feb. 13, 2009

(86) PCT No.: PCT/US2009/034069
§ 371 (c)(1),
(2), (4) Date: Jan. 18, 2011

(87) PCT Pub. No.: WO2009/102966
PCT Pub. Date: Aug. 20, 2009

(65) Prior Publication Data
US 2011/0111054 A1    May 12, 2011

Related U.S. Application Data

(60) Provisional application No. 61/028,499, filed on Feb. 13, 2008.

(51) Int. Cl.
*A61K 38/18*     (2006.01)

(52) U.S. Cl.
USPC .......... 514/8.8; 514/13.3; 514/15.4; 514/16.5

(58) Field of Classification Search
None
See application file for complete search history.

(56) References Cited

U.S. PATENT DOCUMENTS

| | | | |
|---|---|---|---|
| 4,968,590 | A | 11/1990 | Kuberasampath et al. |
| 5,011,691 | A | 4/1991 | Oppermann et al. |
| 5,266,683 | A | 11/1993 | Oppermann et al. |
| 5,411,941 | A | 5/1995 | Grinna et al. |
| 5,834,188 | A | 11/1998 | Harada et al. |
| 6,040,431 | A | 3/2000 | Keck et al. |
| 6,273,598 | B1 | 8/2001 | Keck et al. |
| 6,723,698 | B2 | 4/2004 | Rueger et al. |
| 2002/0028453 | A1 | 3/2002 | Keck et al. |
| 2002/0049159 | A1 | 4/2002 | Rueger et al. |
| 2003/0185792 | A1 | 10/2003 | Keck et al. |

FOREIGN PATENT DOCUMENTS

| | | |
|---|---|---|
| EP | 0601106 | 5/2000 |
| EP | 0876401 | 6/2007 |
| JP | 2004-523537 | 8/2004 |
| JP | 2006-516020 | 6/2006 |
| JP | 2008-516971 | 5/2008 |
| WO | WO 88/00205 | 1/1988 |
| WO | WO 92/00382 | 1/1992 |
| WO | WO 92/15323 | 9/1992 |
| WO | WO 93/04692 | 3/1993 |
| WO | WO 93/05172 | 3/1993 |
| WO | WO 93/05751 | 4/1993 |
| WO | WO 93/16099 | 8/1993 |
| WO | WO 94/03200 | 2/1994 |
| WO | WO 93/09229 | 5/1994 |
| WO | WO 94/10203 | 5/1994 |
| WO | WO 94/15949 | 7/1994 |
| WO | WO 94/15966 | 7/1994 |
| WO | WO 94/21681 | 9/1994 |
| WO | WO 94/26892 | 11/1994 |
| WO | WO 94/26893 | 11/1994 |
| WO | WO 95/01801 | 1/1995 |
| WO | WO 95/01802 | 1/1995 |
| WO | WO 95/16035 | 1/1995 |
| WO | WO 95/10539 | 4/1995 |
| WO | WO 95/33830 | 12/1995 |
| WO | WO 96/01316 | 1/1996 |
| WO | WO 96/01845 | 1/1996 |
| WO | WO 96/14335 | 5/1996 |
| WO | WO 96/36710 | 11/1996 |
| WO | WO 97/26277 | 7/1997 |
| WO | WO 02/062335 | 8/2002 |
| WO | WO 2004/019876 | 3/2004 |
| WO | WO 2006/044657 | 4/2006 |

OTHER PUBLICATIONS

Ortho Biotech Products to return BMP-7 program to Curis: Dairydrugnews.com (Daily Essentials), May 22, 2007.
Davies et al., "Pathophysiological mechanisms of vascular calcification in end-stage renal disease," Kidney Int, 60:472-479 (2001).
Hruska et al., "Bone morphogenetic proteins in vascular calcification," Circ Res, 97:105-114 (2005).
Hruska et al., "Connections between vascular calcification and progression of chronic kidney disease: therapeutic alternatives," Kidney Int Suppl, Suppl 99, S142-S151 (2005).
Hruska et al., "Osteoporosis and cardiovascular disease: lessons from chronic kidney disease," Clinical Cases in Mineral and Bone Metabolism, 5:35-39 (2008).
Lund et al., "CKD induces an adynamic bone disorder and vascular calcification amenable to skeletal anabolism in the metabolic syndrome," 26th Annual Meeting of the American Society for Bone and Mineral Rese Arch, 19:S473 (2004) (Abstract only).
Mathew et al., "Function and effect of bone morphogenetic protein-7 in kidney bone and the bone-vascular links in chronic kidney disease," European Journal of Clinical Investigation, 36:43-50, Suppl. 2 (2006).
Mathew et al., "The mechanism of phosphorus as a cardiovascular risk factor in CKD," J Am Soc Nephrol, 19:1092-1105 (2008).
Stompór, "An overview of the pathophysiology of vascular calcification in chronic kidney disease," Peritoneal Dialysis International, Pergamon Press, NY, 27:S215-S222, Suppl. 2 (2007).
Asahina et al., "Human osteogenic protein-1 induces chondroblastic, osteoblastic, and/or adipocytic differentiation of clonal murine target cells," Exp Cell Res, 222:38-47 (1996).
Aubin et al., "The osteoblast lineage," In: Principles of Bone Biology, edited by Bilezikian JP, Raisz LG, Rodan GA, New York, Academic Press, pp. 51-67 (1996).

(Continued)

*Primary Examiner* — Elizabeth C Kemmerer
(74) *Attorney, Agent, or Firm* — Ropes & Gray LLP

(57) ABSTRACT

The present invention relates to prevention and treatment of vascular sclerosis, vascular calcification (VC) and neointimal hyperplasia using a morphogen.

3 Claims, 36 Drawing Sheets

(56) References Cited

OTHER PUBLICATIONS

Beck et al., "Phosphate is a specific signal for induction of osteopontin gene expression," Proc Natl Acad Sci, 97:8352-8357 (2000).
Berl et al., "Kidney-heart interactions: epidemiology, pathogenesis, and treatment," Clin J Am Soc Nephrol, 1:8-18 (2006).
Biber et al., "PDZ interactions and proximal tubular phosphate reabsorption,"Am J Physiol Renal Physiol, 287:871-875 (2004).
Block et al., "Effects of sevelamer and calcium on coronary artery calcification in patients new to hemodialysis," Kidney Int, 68:1815-1824 (2005).
Boström et al., "Bone morphogenetic protein expression in human atherosclerotic lesions," J Clin Invest, 91:1800-1809 (1993).
Celeste et al., "Identification of transforming growth factor beta family members present in bone-inductive protein purified from bovine bone," Proc Natl Acad Sci, 87:9843-9847 (1990).
Chen et al., "Vascular calcification in chronic kidney disease," Sem Nephrol, 24:61-68 (2004).
Cheng et al., "Msx2 promotes osteogenesis and suppresses adipogenic differentiation of multipotent mesenchymal progenitors," J Biol Chem, 278:45969-45977 (2003).
Chertow et al., "Sevelamer attenuates the progression of coronary and aortic calcification in hemodialysis patients," Kidney Int, 62:245-252 (2002).
Cinat et al., "A prospective evaluation of PTFE graft patency and surveillance techniques in hemodialysis access," Ann Vasc Surg, 13(2):191-198 (1999).
Davies et al., "BMP-7 is an efficacious treatment of vascular calcification in a murine model of atherosclerosis and chronic renal failure," J Am Soc Neph, 14:1559-1567 (2003).
Davies et al., "Low turnover osteodystrophy and vascular calcification are amenable to skeletal anabolism in an animal model of chronic kidney disease and the metabolic syndrome," J Am Soc Neph, 16:917-928 (2005).
Dayhoff et al., "A Model of Evolutionary Change in Proteins," Chapter 22 Atlas of Protein Sequence and Structure, 5(suppl. 3):345-52 (1978).
Dhore et al., "Differential expression of bone matrix regulatory proteins in human atherosclerotic plaques," Arterioscler Thromb Vasc Biol, 21:1998-2003 (2001).
Doherty et al., "Rationale for the role of osteoclast-like cells in arterial calcification," FASEB J, 16:577-582 (2002).
Dorai et al., "Bone morphogenetic protein-7 (osteogenic protein-1) inhibits smooth muscle cell proliferation and stimulates the expression of markers that are characteristic of SMC phenotype in vitro," J Cellular Physiol, 184:37-45 (2000).
Dorai et al., "Bone Morphogenetic Protein-7 Modulates Genes that Maintain the Vascular Smooth Muscle Cell Phenotype in Culture," J Bone and Joint Surg, 83:S70-S78 (2001).
Ducy et al., "Osf2/Cbfa1: a transcriptional activator of osteoblast differentiation," Cell, 89:747-754 (1997).
Ducy et al., "Two distinct osteoblast-specific cis acting elements control expression of a mouse osteocalcin gene," Mol Cell Biol, 15:1858-1869 (1995).
Ezzahiri et al., "Haemodialysis vascular access and fistula surveillance methods in The Netherlands," Nephrol Dial Transplant, 14(9):2110-2115 (1999).
Go et al., "Chronic kidney disease and the risks of death, cardiovascular events, and hospitalization," New Engl J Med, 351:1296-1305 (2004).
Harris et al., "Recombinant bone morphogenetic protein 2 accelerates the bone cell differentiation program and auto-regulates BMP 2 expression and BMP 2 promoter activity in fetal rat calvariae osteoblast cultures," Mol Cell Different, 3:137-155 (1995).
Hoffmann et al., "Transcriptional control of the tissue-specific, developmentally regulated osteocalcin gene requires a binding motif for the Msx family of homeodomain proteins," Proc Nat'l Acad Sci, 91:12887-12891 (1994).
Jono et al., Phosphate regulation of vascular smooth muscle cell calcification, Circ Res, 87:e10-e17 (2000).
Kestenbaum et al., "Serum phosphate levels and mortality risk among people with chronic kidney disease," J Am Soc Nephrol, 16:520-528 (2005).
Koga et al., "NFAT and Osterix cooperatively regulate bone formation," Nature Medicine, 11:880-885 (2005).
Komori et al., "Targeted Disruption of Cbfa1 Results in a Complete Lack of Bone Formation owing to Maturational Arrest of Osteoblasts," Cell, 89:755-764 (1997).
Lecanda et al., "Regulation of bone matrix protein expression and induction of differentiation of human osteoblasts and human bone marrow stromal cells by bone morphogenetic protein-2," J Cell Biochem, 67:386-398 (1997).
Lee et al., "BMP-2 induced osterix expression is mediated by Dlx5 but is independent of Runx2," Biochem Biophys Res Com, 309:689-694 (2003).
Lee et al., "Cost analysis of ongoing care of patients with end-stage renal disease: the impact of dialysis modality and dialysis access," Am J Kidney Dis, 40(3):611-622 (2002).
Lee, "Expression of growth/differentiation factor 1 in the nervous system: conservation of a bicistronic structure," Proc Natl Acad Sci, 88:4250-4254 (1991).
Leidenfrost et al., "A model of primary atherosclerosis and post-angioplasty restenosis in mice," Am J Pathol, 163(2):773-778 (2003).
Lemann et al. "Use of the serum creatinine to estimate glomerular filtration rate in health and early diabetic nephropathy," Am J Kidney Dis, 16(3): 236-243 (1990).
Li et al., "BMP-2 promotes phosphate uptake, phenotypic modulation, and calcification of vascular smooth muscle cells," Atherosclerosis, 199:271-277 (2008).
Li et al., "Role of the Sodium-Dependent Phosphate Cotransporter, Pit-1, in Vascular Smooth Muscle Cell Calcification," Circ Res, 98:905-912 (2006).
London et al., "Arterial media calcification in end-stage renal diseases: impact on all-cause and cardiovascular mortality," Nephrol Dial Transplant, 18:1731-1740 (2003).
Lund et al., "Successful treatment of an adynamic bone disorder with bone morphogenetic protein-7 in a renal ablation model," J Am Soc Neph, 15:359-369 (2004).
Lyons et al., "Vgr-1, a mammalian gene related to Xenopus Vg-1, is a member of the transforming growth factor beta gene superfamily," Proc Natl Acad Sci, 86:4554-4558 (1989).
Macias-Silva et al., "Specific Activation of Smad1 Signaling Pathways by the BMP7 Type I Receptor, ALK2," J Biol Chem, 273:25628-25636 (1998).
Mattana et al., "Leukocyte-polytetrafluoroethylene interaction enhances proliferation of vascular smooth muscle cells via tumor necrosis factor-alpha secretion," Kidney Int, 52(6):1478-1485 (1997).
Mathew et al., "Bone morphogenetic protein-7 (BMP-7) inhibits vascular calcification (VC) by stimulating the contractile vascular smooth muscle cell (VSMC) phenotype," J Am Soc Nephrol, 16:52a (2005) (Abstract).
Mathew et al., "Reversal of the adynamic bone disorder and decreased vascular calcification in chronic kidney disease by sevelamer carbonate therapy," J Am Soc Nephrol, 18:122-130 (2007).
Moe et al., "Medial artery calcification in ESRD patients is associated with deposition of bone matrix proteins," Kidney International, 61:638-647 (2002).
Moe et al., "Role of calcification inhibitors in the pathogenesis of vascular calcification in chronic kidney disease (CKD)," Kidney Int, 67:2295-2304 (2005).
Moe et al., "Uremia induces the osteoblast differentiation factor Cbfa1 in human blood vessels," Kidney Int, 63:1003-1011 (2003).
Nakashima et al., "The novel zinc finger-containing transcription factor osterix is required for osteoblast differentiation and bone formationm" Cell, 108:17-29 (2002).
Needleman et al., "A general method applicable to the search for similarities in the amino acid sequence of two proteins," J Mol Biol, 48:443-453 (1970).

(56) References Cited

OTHER PUBLICATIONS

Nikkari et al., "Restenosis after vascular reconstruction," Ann Med, 26(2):95-100 (1994).
Ohtake et al., "High Prevalence of Occult Coronary Artery Stenosis in Patients with Chronic Kidney Disease at the Initiation of Renal Replacement Therapy: An Angiographic Examination," Am Soc Nephrol, 16:1141-1148 (2005).
Özkaynak et al., "OP-1 cDNA encodes an osteogenic protein in the TGF-beta family," EMBO J., 9:2085-2093 (1990).
Padgett et al., "A transcript from a *Drosophila* pattern gene predicts a protein homologous to the transforming growth factor-beta family," Nature, 325:81-84 (1987).
Phan et al., "Sevelamer Prevents Uremia-Enhanced Atherosclerosis Progression in Apolipoprotein E-Deficient Mice," Circulation, 112:2875-2882 (2005).
Piscione et al., "BMP-2 and OP-1 exert direct and opposite effects on renal branching morphogenesis," Am J Phys (Renal), 273:F961-F975 (1997).
Piscione et al., "BMP7 controls collecting tubule cell proliferation and apoptosis via Smad1-dependent and -independent pathways," Am J Physiol Renal Physiol, 280:F19-F33 (2001).
Raggi et al., "Cardiac calcification in adult hemodialysis patients. A link between end-stage renal disease and cardiovascular disease?" J Am Coll Cardiol, 39:695-701 (2002).
Reynolds et al., "Human Vascular Smooth Muscle Cells Undergo Vesicle-Mediated Calcification in Response to Changes in Extracellular Calcium and Phosphate Concentrations: A Potential Mechanism for Accelerated Vascular Calcification in ESRD," J Am Soc Nephrol, 15:2857-2867 (2004).
Roy-Chaudhury et al., "Hemodialysis vascular access dysfunction: a cellular and molecular viewpoint," J Am Soc Nephrol, 17(4):1112-1127 (2006).
Sampath et al., "Dissociative extraction and reconstitution of extracellular matrix components involved in local bone differentiation," Proc Natl Acad Sci, 78: 7599-7603 (1981).
Shao et al., "Msx2 promotes cardiovascular calcification by activating paracrine Wnt signals," J Clin Invest, 115:1210-1220 (2005).
Shenoy et al., "A multicenter study of permanent hemodialysis access patency: beneficial effect of clipped vascular anastomotic technique," J Vasc Surg, 38(2):229-235 (2003).
Slinin et al., "Calcium, Phosphorus, Parathyroid Hormone, and Cardiovascular Disease in Hemodialysis Patients: The USRDS Waves 1, 3, and 4 Study," J Am Soc Nephrol, 16:1788-1793 (2005).
Steitz et al., "Smooth muscle cell phenotypic transition associated with calcification," Circ Res, 89:1147-1154 (2001).
Surendran et al., "Wnt-dependent-b-catenin signaling is activated after unilateral ureteral obstruction, and recombinant secreted frizzled-related protein 4 alters the progression of renal fibrosis," J Am Soc Neph, 16:2373-2384 (2005).
Tamagaki et al., "Severe hyperparathyroidism with bone abnormalities and metastatic calcification in rats with adenine-induced uraemia," Nephrol Dial Transplant, 21:651-659 (2006).
Tordoir et al., "Early experience with stretch polytetrafluoroethylene grafts for haemodialysis access surgery: results of a prospective randomised study," Eur J Vasc Endovasc Surg, 9(3):305-309 (1995).
Towler et al., "Diet-induced diabetes activates an osteogenic gene regulatory program in the aortas of low density lipoprotein receptor-deficient mice," J Biol Chem, 273:30427-30434 (1998).
Trion et al., "Vascular smooth muscle cells and calcification in atherosclerosis," Am Heart J, 147:808-814 (2004).
Tyson et al., "Osteo/chondrocytic transcription factors and their target genes exhibit distinct patterns of expression in human arterial calcification," Arterioscler Thromb Vasc Biol, 23:489-494 (2003).
von Heijne, "A new method for predicting signal sequence cleavage sites," Nucleic Acids Research, 14:4683-4691 (1986).
Weeks et al., "A maternal mRNA localized to the vegetal hemisphere in *Xenopus* eggs codes for a growth factor related to TGF-beta," Cell, 51:861-867 (1987).
Wozney et al., "Novel regulators of bone formation: molecular clones and activities," Science, 242:1528-1534 (1988).
Zile et al., "Diastolic heart failure—abnormalities in active relaxation and passive stiffness of the left ventricle," N Eng J Med, 350:1953-1959 (2004).

% Sequence Similarity to Human OP-1 Seven-Cysteine Domain

| Sequence | % Similarity | % Non Conservative |
|---|---|---|
| hOP-1 | 100 | 0 |
| mOP-1 | 100 | 0 |
| hOP-2 | 97 | 3 |
| mOP-2 | 97 | 3 |
| BMP-5 | 97 | 3 |
| BMP-6 | 96 | 4 |
| Vgr-1(PT) | 94 | 6 |
| OP-3 | 91 | 9 |
| 60A | 90 | 10 |
| BMP-4 | 90 | 10 |
| BMP-2 | 89 | 11 |
| dpp | 87 | 13 |
| UNIVIN | 87 | 13 |
| dpp(PT) | 86 | 14 |
| Vg-1 | 86 | 14 |
| CDMP-1 | 85 | 15 |
| CDMP-3 | 83 | 17 |
| GDF-3 | 83 | 17 |
| CDMP-2 | 82 | 18 |
| DORSALIN | 79 | 21 |
| GDF-1(PT) | 78 | 22 |
| GDF-10 | 78 | 22 |
| BMP-3b | 78 | 22 |
| BMP-10 | 78 | 23 |
| BMP-3 | 78 | 23 |
| SCREW | 77 | 23 |
| ADMP | 77 | 24 |
| TGF-β2 | 73 | 27 |
| GDF-1 | 73 | 28 |
| BMP-9 | 73 | 28 |
| NODAL | 71 | 29 |
| inhibinβA | 71 | 29 |
| BMP-15 | 71 | 29 |
| TGF-β3 | 69 | 31 |
| inhibinβB | 69 | 31 |
| inhibinβC | 69 | 31 |
| TGF-β5 | 67 | 33 |
| TGF-β1 | 67 | 33 |
| GDF-12 | 67 | 33 |
| GDF-11 | 66 | 34 |
| TGF-β4 | 66 | 34 |
| GDF-9 | 66 | 34 |
| GDF-8 | 64 | 36 |
| BMP-11 | 60 | 40 |
| GDNF | 49 | 51 |

Fig. 10

SEQ ID NO: 1     Human OP1 amino acid sequence

Met His Val Arg Ser Leu Arg Ala Ala Pro His Ser Phe Val Ala Leu Trp Ala Pro
 1           5               10              15              20
Leu Phe Leu Leu Arg Ser Ala Leu Ala Asp Phe Ser Leu Asp Asn Glu Val His Ser Ser
             25              30              35              40
Phe Ile His Arg Arg Leu Arg Ser Gln Glu Arg Arg Glu Met Gln Arg Glu Ile Leu Ser
             45              50              55              60
Ile Leu Gly Leu Pro His Arg Pro Arg Pro His Leu Gln Gly Lys His Asn Ser Ala Pro
             65              70              75              80
Met Phe Met Leu Asp Leu Tyr Asn Ala Met Ala Val Glu Glu Gly Gly Pro Gly Gly
             85              90              95              100
Gln Gly Phe Ser Tyr Pro Tyr Lys Ala Val Phe Ser Thr Gln Gly Pro Pro Leu Ala Ser
             105             110             115             120
Leu Gln Asp Ser His Phe Leu Thr Asp Ala Asp Met Val Met Ser Phe Val Asn Leu Val
             125             130             135             140
Glu His Asp Lys Glu Phe Phe His Pro Arg Tyr His His Arg Glu Phe Arg Phe Asp Leu
             145             150             155             160
Ser Lys Ile Pro Glu Gly Glu Ala Val Thr Ala Ala Glu Phe Arg Ile Tyr Lys Asp Tyr
             165             170             175             180
Ile Arg Glu Arg Phe Asp Asn Glu Thr Phe Arg Ile Ser Val Tyr Gln Val Leu Gln Glu
             185             190             195             200
His Leu Gly Arg Glu Ser Asp Leu Phe Leu Leu Asp Ser Arg Thr Leu Trp Ala Ser Glu
             205             210             215             220
Glu Gly Trp Leu Val Phe Asp Ile Thr Ala Thr Ser Asn His Trp Val Val Asn Pro Arg
             225             230             235             240
His Asn Leu Gly Leu Gln Leu Ser Val Glu Thr Leu Asp Gly Gln Ser Ile Asn Pro Lys
             245             250             255             260
Leu Ala Gly Leu Ile Gly Arg His Gly Pro Gln Asn Lys Gln Pro Phe Met Val Ala Phe
             265             270             275             280
Phe Lys Ala Thr Glu Val His Phe Arg Ser Ile Arg Ser Thr Gly Ser Lys Gln Arg Ser
             285             290             295             300
Gln Asn Arg Ser Lys Thr Pro Lys Asn Gln Glu Ala Leu Arg Met Ala Asn Val Ala Glu
             305             310             315             320
Asn Ser Ser Ser Asp Gln Arg Gln Ala Cys Lys Lys His Glu Leu Tyr Val Ser Phe Arg
             325             330             335             340
Asp Leu Gly Trp Gln Asp Trp Ile Ile Ala Pro Glu Gly Tyr Ala Ala Tyr Tyr Cys Glu
             345             350             355             360
Gly Glu Cys Ala Phe Pro Leu Asn Ser Tyr Met Asn Ala Thr Asn His Ala Ile Val Gln
             365             370             375             380
Thr Leu Val His Phe Ile Asn Pro Glu Thr Val Pro Lys Pro Cys Cys Ala Pro Thr Gln
             385             390             395             400
Leu Asn Ala Ile Ser Val Leu Tyr Phe Asp Asp Ser Ser Asn Val Ile Leu Lys Lys Tyr
             405             410             415             420
Arg Asn Met Val Val Arg Ala Cys Gly Cys His
             425             430

Figure 13

SEQ ID NO: 2    Amino acid sequence of conserved 6 Cysteine skeleton of human OP-1

Leu Tyr Val Ser Phe Arg Asp Leu Gly Trp Gln Asp Trp Ile Ile Ala
Pro Glu Gly Tyr Ala Ala Tyr Tyr Cys Glu Gly Glu Cys Ala Phe Pro
Leu Asn Ser Tyr Met Asn Ala Thr Asn His Ala Ile Val Gln Thr Leu
Val His Phe Ile Asn Pro Glu Thr Val Pro Lys Pro Cys Cys Ala Pro
Thr Gln Leu Asn Ala Ile Ser Val Leu Tyr Phe Asp Asp Ser Ser Asn
Val Ile Leu Lys Lys Tyr Arg Asn Met Val Val Arg Ala Cys Gly Cys
His

Figure 14

SEQ ID NO: 3   Amino acid sequence of morphogenically active full-length human OP-1

```
Ser Thr Gly Ser Lys Gln Arg Ser Gln Asn Arg Ser Lys Thr Pro Lys
            5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Ser Asn Val Ile Leu Lys Lys Tyr
        115                 120                 125

Arg Asn Met Val Val Arg Ala Cys Gly Cys His
    130                 135
```

Figure 15

SEQ ID NO: 4    Mature mouse OP-1 amino acid sequence

| | | | | | | | | | | | | | | | | | | | |
|---|---|---|---|---|---|---|---|---|---|---|---|---|---|---|---|---|---|---|---|
|Met|His|Val|Arg|Ser|Leu|Arg|Ala|Ala|Ala|Pro|His|Ser|Phe|Val|Ala|Leu|Trp|Ala|Pro|
|1| | | |5| | | | |10| | | | |15| | | | |20|
|Leu|Phe|Leu|Leu|Arg|Ser|Ala|Leu|Ala|Asp|Phe|Ser|Leu|Asp|Asn|Glu|Val|His|Ser|Ser|
| | | | |25| | | | |30| | | | |35| | | | |40|
|Phe|Ile|His|Arg|Arg|Leu|Arg|Ser|Gln|Glu|Arg|Arg|Glu|Met|Gln|Arg|Glu|Ile|Leu|Ser|
| | | | |45| | | | |50| | | | |55| | | | |60|
|Ile|Leu|Gly|Leu|Pro|His|Arg|Pro|Arg|Pro|His|Leu|Gln|Gly|Lys|His|Asn|Ser|Ala|Pro|
| | | | |65| | | | |70| | | | |75| | | | |80|
|Met|Phe|Met|Leu|Asp|Leu|Tyr|Asn|Ala|Met|Ala|Val|Glu|Glu|Ser|Gly|Pro|Asp|Gly|Gln|
| | | | |85| | | | |90| | | | |95| | | | |100|
|Gly|Phe|Ser|Tyr|Pro|Tyr|Lys|Ala|Val|Phe|Ser|Thr|Gln|Gly|Pro|Pro|Leu|Ala|Ser|Leu|
| | | | |105| | | | |110| | | | |115| | | | |120|
|Gln|Asp|Ser|His|Phe|Leu|Thr|Asp|Ala|Asp|Met|Val|Met|Ser|Phe|Val|Asn|Leu|Val|Glu|
| | | | |125| | | | |130| | | | |135| | | | |140|
|His|Asp|Lys|Glu|Phe|Phe|His|Pro|Arg|Tyr|His|His|Arg|Glu|Phe|Arg|Phe|Asp|Leu|Ser|
| | | | |145| | | | |150| | | | |155| | | | |160|
|Lys|Ile|Pro|Glu|Gly|Glu|Ala|Val|Thr|Ala|Ala|Glu|Phe|Arg|Ile|Tyr|Lys|Asp|Tyr|Ile|
| | | | |165| | | | |170| | | | |175| | | | |180|
|Arg|Glu|Arg|Phe|Asp|Asn|Glu|Thr|Phe|Gln|Ile|Thr|Val|Tyr|Gln|Val|Leu|Gln|Glu|His|
| | | | |185| | | | |190| | | | |195| | | | |200|
|Ser|Gly|Arg|Glu|Ser|Asp|Leu|Phe|Leu|Leu|Asp|Ser|Arg|Thr|Ile|Trp|Ala|Ser|Glu|Glu|
| | | | |205| | | | |210| | | | |215| | | | |220|
|Gly|Trp|Leu|Val|Phe|Asp|Ile|Thr|Ala|Thr|Ser|Asn|His|Trp|Val|Val|Asn|Pro|Arg|His|
| | | | |225| | | | |230| | | | |235| | | | |240|
|Asn|Leu|Gly|Leu|Gln|Leu|Ser|Val|Glu|Thr|Leu|Asp|Gly|Gln|Ser|Ile|Asn|Pro|Lys|Leu|
| | | | |245| | | | |250| | | | |255| | | | |260|
|Ala|Gly|Leu|Ile|Gly|Arg|His|Gly|Pro|Gln|Asn|Lys|Gln|Pro|Phe|Met|Val|Ala|Phe|Phe|
| | | | |265| | | | |270| | | | |275| | | | |280|
|Lys|Ala|Thr|Glu|Val|His|Leu|Arg|Ser|Ile|Arg|Ser|Thr|Gly|Gly|Lys|Gln|Arg|Ser|Gln|
| | | | |285| | | | |290| | | | |295| | | | |300|
|Asn|Arg|Ser|Lys|Thr|Pro|Lys|Asn|Gln|Glu|Ala|Leu|Arg|Met|Ala|Ser|Val|Ala|Glu|Asn|
| | | | |305| | | | |310| | | | |315| | | | |320|
|Ser|Ser|Ser|Asp|Gln|Arg|Gln|Ala|Cys|Lys|Lys|His|Glu|Leu|Tyr|Val|Ser|Phe|Arg|Asp|
| | | | |325| | | | |330| | | | |335| | | | |340|
|Leu|Gly|Trp|Gln|Asp|Trp|Ile|Ile|Ala|Pro|Glu|Gly|Tyr|Ala|Ala|Tyr|Tyr|Cys|Glu|Gly|
| | | | |345| | | | |350| | | | |355| | | | |360|
|Glu|Cys|Ala|Phe|Pro|Leu|Asn|Ser|Tyr|Met|Asn|Ala|Thr|Asn|His|Ala|Ile|Val|Gln|Thr|
| | | | |365| | | | |370| | | | |375| | | | |380|
|Leu|Val|His|Phe|Ile|Asn|Pro|Asp|Thr|Val|Pro|Lys|Pro|Cys|Cys|Ala|Pro|Thr|Gln|Leu|
| | | | |385| | | | |390| | | | |395| | | | |400|
|Asn|Ala|Ile|Ser|Val|Leu|Tyr|Phe|Asp|Asp|Ser|Ser|Asn|Val|Ile|Leu|Lys|Lys|Tyr|Arg|
| | | | |405| | | | |410| | | | |415| | | | |420|
|Asn|Met|Val|Val|Arg|Ala|Cys|Gly|Cys|His| | | | | | | | | | |
| | | | |425| | | | |430| | | | | | | | | | |

Figure 16

SEQ ID NO: 5    Mature human OP-2 amino acid sequence

```
Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
            35                  40                  45

Asp Leu Gly Trp Leu Asp Trp Val Ile Ala Pro Gln Gly Tyr Ser Ala
        50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Met Pro
                85                  90                  95

Asp Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
            115                 120                 125

Arg Asn Met Val Val Lys Ala Cys Gly Cys His
            130                 135
```

Figure 17

SEQ ID NO: 6    Mature mouse OP-2 amino acid sequence

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
            35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
            85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

Figure 18

SEQ ID NO: 7          Drosophia DPP amino acid sequence

```
Met Arg Ala Trp Leu Leu Leu Ala Val Leu Ala Thr Phe Gln Thr Ile Val Arg Val Ala Ser
 1               5                   10                  15                  20
Thr Glu Asp Ile Ser Gln Arg Phe Ile Ala Ala Ile Ala Pro Val Ala Ala His Ile Pro Leu Ala
                25                  30                  35                  40
Ser Ala Ser Gly Ser Gly Ser Gly Arg Ser Gly Ser Arg Ser Gly Gly Ala Ser Thr Ser Thr Ala
 45                  50                  55                  60                  65
Leu Ala Lys Ala Phe Asn Pro Phe Ser Glu Pro Ala Ser Phe Ser Asp Ser Asp Lys Ser His Arg
                 70                  75                  80                  85
Ser Lys Thr Asn Lys Lys Pro Ser Lys Ser Asp Ala Asn Arg Gln Phe Asn Glu Val His Lys Pro
         90                  95                  100                 105                 110
Arg Thr Asp Gln Leu Glu Asn Ser Lys Asn Met Ser Lys Gln Leu Val Asn Lys Pro Asn His Asn
                115                 120                 125                 130
Lys Met Ala Val Lys Glu Gln Arg Ser His His Lys Lys Ser His His His Arg Ser His Gln Pro
         135                 140                 145                 150
Lys Gln Ala Ser Ala Ser Thr Glu Ser His Gln Ser Ser Ser Ile Glu Ser Ile Phe Val Glu Glu
155                 160                 165                 170                 175
Pro Thr Leu Val Leu Asp Arg Glu Val Ala Ser Ile Asn Val Pro Ala Asn Ala Lys Ala Ile Ile
                180                 185                 190                 195
Ala Glu Gln Gly Pro Ser Thr Tyr Ser Lys Glu Ala Leu Ile Lys Asp Lys Leu Lys Pro Asp Pro
         200                 205                 210                 215                 220
Ser Thr Leu Val Glu Ile Glu Lys Ser Leu Leu Ser Leu Phe Asn Met Lys Arg Pro Pro Lys Ile
                225                 230                 235                 240
Asp Arg Ser Lys Ile Ile Ile Pro Glu Pro Met Lys Lys Leu Tyr Ala Glu Ile Met Gly His Glu
         245                 250                 255                 260
Leu Asp Ser Val Asn Ile Pro Lys Pro Gly Leu Leu Thr Lys Ser Ala Asn Thr Val Arg Ser Phe
265                 270                 275                 280                 285
Thr His Lys Asp Ser Lys Ile Asp Asp Arg Phe Pro His His His Arg Phe Arg Leu His Phe Asp
                290                 295                 300                 305
Val Lys Ser Ile Pro Ala Asp Glu Lys Leu Lys Ala Ala Glu Leu Gln Leu Thr Arg Asp Ala Leu
         310                 315                 320                 325                 330
Ser Gln Gln Val Val Ala Ser Arg Ser Ser Ala Asn Arg Thr Arg Tyr Gln Val Leu Val Tyr Asp
                335                 340                 345                 350
Ile Thr Arg Val Gly Val Arg Gly Gln Arg Glu Pro Ser Tyr Leu Leu Leu Asp Thr Lys Thr Val
         355                 360                 365                 370
Arg Leu Asn Ser Thr Asp Thr Val Ser Leu Asp Val Gln Pro Ala Val Asp Arg Trp Leu Ala Ser
375                 380                 385                 390                 395
Pro Gln Arg Asn Tyr Gly Leu Leu Val Glu Val Arg Thr Val Arg Ser Leu Lys Pro Ala Pro His
                400                 405                 410                 415
His His Val Arg Leu Arg Arg Ser Ala Asp Glu Ala His Glu Arg Trp Gln His Lys Gln Pro Leu
         420                 425                 430                 435                 440
Leu Phe Thr Tyr Thr Asp Asp Gly Arg His Lys Ala Arg Ser Ile Arg Asp Val Ser Gly Gly Glu
                445                 450                 455                 460
Gly Gly Gly Lys Gly Gly Arg Asn Lys Arg Gln Pro Arg Arg Pro Thr Arg Arg Lys Asn His Asp
         465                 470                 475                 480
Asp Thr Cys Arg Arg His Ser Leu Tyr Val Asp Phe Ser Asp Val Gly Trp Asp Trp Ile Val
485                 490                 495                 500                 505
Ala Pro Leu Gly Tyr Asp Ala Tyr Tyr Cys His Gly Lys Cys Pro Phe Pro Leu Ala Asp His Phe
                510                 515                 520                 525
Asn Ser Thr Asn His Ala Val Val Gln Thr Leu Val Asn Asn Met Asn Pro Gly Lys Val Pro Lys
         530                 535                 540                 545                 550
Ala Cys Cys Val Pro Thr Gln Leu Asp Ser Val Ala Met Leu Tyr Leu Asn Asp Gln Ser Thr Val
                555                 560                 565                 570
Val Leu Lys Asn Tyr Gln Glu Met Thr Val Val Gly Cys Gly Cys Arg
         575                 580                 585
```

Figure 19

SEQ ID NO: 8    Xenopus VG1 amino acid sequence

```
Met Val Trp Leu Arg Leu Trp Ala Phe Leu His Ile Leu Ala Ile Val Thr Leu Asp Pro
 1           5                   10                  15                  20

Glu Leu Lys Arg Arg Glu Glu Leu Phe Leu Arg Ser Leu Gly Phe Ser Ser Lys Pro Asn
             25                  30                  35                  40

Pro Val Ser Pro Pro Pro Val Pro Ser Ile Leu Trp Arg Ile Phe Asn Gln Arg Met Gly
             45                  50                  55                  60

Ser Ser Ile Gln Lys Lys Lys Pro Asp Leu Cys Phe Val Glu Glu Phe Asn Val Pro Gly
             65                  70                  75                  80

Ser Val Ile Arg Val Phe Pro Asp Gln Gly Arg Phe Ile Ile Pro Tyr Ser Asp Asp Ile
             85                  90                  95                  100

His Pro Thr Gln Cys Leu Glu Lys Arg Leu Phe Phe Asn Ile Ser Ala Ile Glu Lys Glu
             105                 110                 115                 120

Glu Arg Val Thr Met Gly Ser Gly Ile Glu Val Gln Pro Glu His Leu Leu Arg Lys Gly
             125                 130                 135                 140

Ile Asp Leu Arg Leu Tyr Arg Thr Leu Gln Ile Thr Leu Lys Gly Met Gly Arg Ser Lys
             145                 150                 155                 160

Thr Ser Arg Lys Leu Leu Val Ala Gln Thr Phe Arg Leu Leu His Lys Ser Leu Phe Phe
             165                 170                 175                 180

Asn Leu Thr Glu Ile Cys Gln Ser Trp Gln Asp Pro Leu Lys Asn Leu Gly Leu Val Leu
             185                 190                 195                 200

Glu Ile Phe Pro Lys Lys Glu Ser Ser Trp Met Ser Thr Ala Asn Asp Glu Cys Lys Asp
             205                 210                 215                 220

Ile Gln Thr Phe Leu Tyr Thr Ser Leu Leu Thr Val Thr Leu Asn Pro Leu Arg Cys Lys
             225                 230                 235                 240

Arg Pro Arg Arg Lys Arg Ser Tyr Ser Lys Leu Pro Phe Thr Ala Ser Asn Ile Cys Lys
             245                 250                 255                 260

Lys Arg His Leu Tyr Val Glu Phe Lys Asp Val Gly Trp Gln Asn Trp Val Ile Ala Pro
             265                 270                 275                 280

Gln Gly Tyr Met Ala Asn Tyr Cys Tyr Gly Glu Cys Pro Tyr Pro Leu Thr Glu Ile Leu
             285                 290                 295                 300

Asn Gly Ser Asn His Ala Ile Leu Gln Thr Leu Val His Ser Ile Glu Pro Glu Asp Ile
             305                 310                 315                 320

Pro Leu Pro Cys Cys Val Pro Thr Lys Met Ser Pro Ile Ser Met Leu Phe Tyr Asp Asn
             325                 330                 335                 340

Asn Asp Asn Val Val Leu Arg His Tyr Glu Asn Met Ala Val Asp Glu Cys Gly Cys Arg
             345                 350                 355                 360
```

Figure 20

SEQ ID NO: 9        Mouse Vgr-1 amino acid sequence

Met Arg Lys Met Gln Lys Glu Ile Leu Ser Val Leu Gly Pro Pro His Arg Pro Arg Pro
 1               5                  10                 15                  20
Leu His Gly Leu Gln Gln Pro Gln Pro Pro Val Leu Pro Pro Gln Gln Gln Gln Gln Gln
                25                  30                 35                  40
Gln Gln Gln Gln Thr Ala Arg Glu Glu Pro Pro Gly Arg Leu Lys Ser Ala Pro Leu
                45                  50                 55                  60
Phe Met Leu Asp Leu Tyr Asn Ala Leu Ser Asn Asp Asp Glu Glu Asp Gly Ala Ser Glu
                65                  70                 75                  80
Gly Val Gly Gln Glu Pro Gly Ser His Gly Gly Ala Ser Ser Ser Gln Leu Arg Gln Pro
                85                  90                 95                 100
Ser Pro Gly Ala Ala His Ser Leu Asn Arg Lys Ser Leu Leu Ala Pro Gly Pro Gly Gly
                105                 110                115                 120
Gly Ala Ser Pro Leu Thr Ser Ala Gln Asp Ser Ala Phe Leu Asn Asp Ala Asp Met Val
                125                 130                135                 140
Met Ser Phe Val Asn Leu Val Glu Tyr Asp Lys Glu Phe Ser Pro His Gln Arg His His
                145                 150                155                 160
Lys Glu Phe Lys Phe Asn Leu Ser Gln Ile Pro Glu Gly Glu Ala Val Thr Ala Ala Glu
                165                 170                175                 180
Phe Arg Val Tyr Lys Asp Cys Val Val Gly Ser Phe Lys Asn Gln Thr Phe Leu Ile Ser
                185                 190                195                 200
Ile Tyr Gln Val Leu Gln Glu His Gln His Arg Asp Ser Asp Leu Phe Leu Leu Asp Thr
                205                 210                215                 220
Arg Val Val Trp Ala Ser Glu Glu Gly Trp Leu Glu Phe Asp Ile Thr Ala Thr Ser Asn
                225                 230                235                 240
Leu Trp Val Val Thr Pro Gln His Asn Met Gly Leu Gln Leu Ser Val Val Thr Arg Asp
                245                 250                255                 260
Gly Leu His Val Asn Pro Arg Ala Ala Gly Leu Val Gly Arg Asp Gly Pro Tyr Asp Lys
                265                 270                275                 280
Gln Pro Phe Met Val Ala Phe Phe Lys Val Ser Glu Val His Val Arg Thr Thr Arg Ser
                285                 290                295                 300
Ala Ser Ser Arg Arg Arg Gln Gln Ser Arg Asn Arg Ser Thr Gln Ser Gln Asp Val Ser
                305                 310                315                 320
Arg Gly Ser Gly Ser Ser Asp Tyr Asn Gly Ser Glu Leu Lys Thr Ala Cys Lys Lys His
                325                 330                335                 340
Glu Leu Tyr Val Ser Phe Gln Asp Leu Gly Trp Gln Asp Trp Ile Ile Ala Pro Lys Gly
                345                 350                355                 360
Tyr Ala Ala Asn Tyr Cys Asp Gly Glu Cys Ser Phe Pro Leu Asn Ala His Met Asn Ala
                365                 370                375                 380
Thr Asn His Ala Ile Val Gln Thr Leu Val His Leu Met Asn Pro Glu Tyr Val Pro Lys
                385                 390                395                 400
Pro Cys Cys Ala Pro Thr Lys Leu Asn Ala Ile Ser Val Leu Tyr Phe Asp Asp Asn Ser
                405                 410                415                 420
Asn Val Ile Leu Lys Lys Tyr Arg Asn Met Val Val Arg Ala Cys Gly Cys His
                425                 430                435

Figure 21

SEQ ID NO: 10      Human CBMP2Λ amino acid sequence CBMP2Λ(fx)

| | | | | | | | | | | | | | | | | | | | |
|---|---|---|---|---|---|---|---|---|---|---|---|---|---|---|---|---|---|---|---|
|Met|Val|Ala|Gly|Thr|Arg|Cys|Leu|Leu|Ala|Leu|Le

SEQ ID NO: 11    Human CBMP2B amino acid sequence CBMPB(fx)

```
Met Ile Pro Gly Asn Arg Met Leu Met Val Val Leu Leu Cys Gln Val Leu Leu Gly Gly
 1               5                  10                  15                  20
Ala Ser His Ala Ser Leu Ile Pro Glu Thr Gly Lys Lys Lys Val Ala Glu Ile Gln Gly
                25                  30                  35                  40
His Ala Gly Gly Arg Arg Ser Gly Gln Ser His Glu Leu Leu Arg Asp Phe Glu Ala Thr
                45                  50                  55                  60
Leu Leu Gln Met Phe Gly Leu Arg Arg Pro Gln Pro Ser Lys Ser Ala Val Ile Pro
                65                  70                  75                  80
Asp Tyr Met Arg Asp Leu Tyr Arg Leu Gln Ser Gly Glu Glu Glu Glu Glu Gln Ile His
                85                  90                  95                  100
Ser Thr Gly Leu Glu Tyr Pro Glu Arg Pro Ala Ser Arg Ala Asn Thr Val Arg Ser Phe
                105                 110                 115                 120
His His Glu Glu His Leu Glu Asn Ile Pro Gly Thr Ser Glu Asn Ser Ala Phe Arg Phe
                125                 130                 135                 140
Leu Phe Asn Leu Ser Ser Ile Pro Glu Asn Glu Val Ile Ser Ser Ala Glu Leu Arg Leu
                145                 150                 155                 160
Phe Arg Glu Gln Val Asp Gln Gly Pro Asp Trp Glu Arg Gly Phe His Arg Ile Asn Ile
                165                 170                 175                 180
Tyr Glu Val Met Lys Pro Pro Ala Glu Val Val Pro Gly His Leu Ile Thr Arg Leu Leu
                185                 190                 195                 200
Asp Thr Arg Leu Val His His Asn Val Thr Arg Trp Glu Thr Phe Asp Val Ser Pro Ala
                205                 210                 215                 220
Val Leu Arg Trp Thr Arg Glu Lys Gln Pro Asn Tyr Gly Leu Ala Ile Glu Val Thr His
                225                 230                 235                 240
Leu His Gln Thr Arg Thr His Gln Gly Gln His Val Arg Ile Ser Arg Ser Leu Pro Gln
                245                 250                 255                 260
Gly Ser Gly Asn Trp Ala Gln Leu Arg Pro Leu Leu Val Thr Phe Gly His Asp Gly Arg
                265                 270                 275                 280
Gly His Ala Leu Thr Arg Arg Arg Ala Lys Arg Ser Pro Lys His His Ser Gln Arg
                285                 290                 295                 300
Ala Arg Lys Lys Asn Lys Asn Cys Arg Arg His Ser Leu Tyr Val Asp Phe Ser Asp Val
                305                 310                 315                 320
Gly Trp Asn Asp Trp Ile Val Ala Pro Pro Gly Tyr Gln Ala Phe Tyr Cys His Gly Asp
                325                 330                 335                 340
Cys Pro Phe Pro Leu Ala Asp His Leu Asn Ser Thr Asn His Ala Ile Val Gln Thr Leu
                345                 350                 355                 360
Val Asn Ser Val Asn Ser Ser Ile Pro Lys Ala Cys Cys Val Pro Thr Glu Leu Ser Ala
                365                 370                 375                 380
Ile Ser Met Leu Tyr Leu Asp Glu Tyr Asp Lys Val Val Leu Lys Asn Tyr Gln Glu Met
                385                 390                 395                 400
Val Val Glu Gly Cys Gly Cys Arg
                405
```

Figure 23

SEQ ID NO: 12    Human BMP3 amino acid sequence

Met Ala Gly Ala Ser Arg Leu Leu Phe Leu Trp Leu Gly Cys Phe Cys Val Ser Leu Ala Gln Gly
1               5                   10                  15                  20

Glu Arg Pro Lys Pro Pro Phe Pro Glu Leu Arg Lys Ala Val Pro Gly Asp Arg Thr Ala Gly Gly
            25                  30                  35                  40

Gly Pro Asp Ser Glu Leu Gln Pro Gln Asp Lys Val Ser Glu His Met Leu Arg Leu Tyr Asp Arg
45              50                  55                  60                  65

Tyr Ser Thr Val Gln Ala Ala Arg Thr Pro Gly Ser Leu Glu Gly Gly Ser Gln Pro Trp Arg Pro
                70                  75                  80                  85

Arg Leu Leu Arg Glu Gly Asn Thr Val Arg Ser Phe Arg Ala Ala Ala Glu Thr Leu Glu Arg
    90                  95                  100                 105                 110

Lys Gly Leu Tyr Ile Phe Asn Leu Thr Ser Leu Thr Lys Ser Glu Asn Ile Leu Ser Ala Thr Leu
                115                 120                 125                 130

Tyr Phe Cys Ile Gly Glu Leu Gly Asn Ile Ser Leu Ser Cys Pro Val Ser Gly Gly Cys Ser His
        135                 140                 145                 150

His Ala Gln Arg Lys His Ile Gln Ile Asp Leu Ser Ala Trp Thr Leu Lys Phe Ser Arg Asn Gln
155                 160                 165                 170                 175

Ser Gln Leu Leu Gly His Leu Ser Val Asp Met Ala Lys Ser His Arg Asp Ile Met Ser Trp Leu
            180                 185                 190                 195

Ser Lys Asp Ile Thr Gln Phe Leu Arg Lys Ala Lys Glu Asn Glu Glu Phe Leu Ile Gly Phe Asn
    200                 205                 210                 215                 220

Ile Thr Ser Lys Gly Arg Gln Leu Pro Lys Arg Arg Leu Pro Phe Pro Glu Pro Tyr Ile Leu Val
                225                 230                 235                 240

Tyr Ala Asn Asp Ala Ala Ile Ser Glu Pro Glu Ser Val Val Ser Ser Leu Gln Gly His Arg Asn
            245                 250                 255                 260

Phe Pro Thr Gly Thr Val Pro Lys Trp Asp Ser His Ile Arg Ala Ala Leu Ser Ile Glu Arg Arg
265                 270                 275                 280                 285

Lys Lys Arg Ser Thr Gly Val Leu Leu Pro Leu Gln Asn Asn Glu Leu Pro Gly Ala Glu Tyr Gln
            290                 295                 300                 305

Tyr Lys Lys Asp Glu Val Trp Glu Glu Arg Lys Pro Tyr Lys Thr Leu Gln Ala Gln Ala Pro Glu
    310                 315                 320                 325                 330

Lys Ser Lys Asn Lys Lys Gln Arg Lys Gly Pro His Arg Lys Ser Gln Thr Leu Gln Phe Asp
                335                 340                 345                 350

Glu Gln Thr Leu Lys Lys Ala Arg Arg Lys Gln Trp Ile Glu Pro Arg Asn Cys Ala Arg Arg Tyr
        355                 360                 365                 370

Leu Lys Val Asp Phe Ala Asp Ile Gly Trp Ser Glu Trp Ile Ile Ser Pro Lys Ser Phe Asp Ala
375                 380                 385                 390                 395

Tyr Tyr Cys Ser Gly Ala Cys Gln Phe Pro Met Pro Lys Ser Leu Lys Pro Ser Asn His Ala Thr
            400                 405                 410                 415

Ile Gln Ser Ile Val Arg Ala Val Gly Val Val Pro Gly Ile Pro Glu Pro Cys Cys Val Pro Glu
    420                 425                 430                 435                 440

Lys Met Ser Ser Leu Ser Ile Leu Phe Phe Asp Glu Asn Lys Asn Val Val Leu Lys Val Tyr Pro
                445                 450                 455                 460

Asn Met Thr Val Glu Ser Cys Ala Cys Arg
            465                 470

Figure 24

SEQ ID NO: 13    Human GDF-1 amino acid sequence

```
Met Pro Pro Pro Gln Gln Gly Pro Cys Gly His His Leu Leu Leu Leu Leu Ala Leu Leu
 1               5                  10                  15                  20
Leu Pro Ser Leu Pro Leu Thr Arg Ala Pro Val Pro Pro Gly Pro Ala Ala Ala Leu Leu
                25                  30                  35                  40
Gln Ala Leu Gly Leu Arg Asp Glu Pro Gln Gly Ala Pro Arg Leu Arg Pro Val Pro Pro
                45                  50                  55                  60
Val Met Trp Arg Leu Phe Arg Arg Arg Asp Pro Gln Glu Thr Arg Ser Gly Ser Arg Arg
                65                  70                  75                  80
Thr Ser Pro Gly Val Thr Leu Gln Pro Cys His Val Glu Glu Leu Gly Val Ala Gly Asn
                85                  90                  95                 100
Ile Val Arg His Ile Pro Asp Arg Gly Ala Pro Thr Arg Ala Ser Glu Pro Val Ser Ala
               105                 110                 115                 120
Ala Gly His Cys Pro Glu Trp Thr Val Val Phe Asp Leu Ser Ala Val Glu Pro Ala Glu
               125                 130                 135                 140
Arg Pro Ser Arg Ala Arg Leu Glu Leu Arg Phe Ala Ala Ala Ala Ala Ala Ala Pro Glu
               145                 150                 155                 160
Gly Gly Trp Glu Leu Ser Val Ala Gln Ala Gly Gln Gly Ala Gly Ala Asp Pro Gly Pro
               165                 170                 175                 180
Val Leu Leu Arg Gln Leu Val Pro Ala Leu Gly Pro Pro Val Arg Ala Glu Leu Leu Gly
               185                 190                 195                 200
Ala Ala Trp Ala Arg Asn Ala Ser Trp Pro Arg Ser Leu Arg Leu Ala Leu Ala Leu Arg
               205                 210                 215                 220
Pro Arg Ala Pro Ala Ala Cys Ala Arg Leu Ala Glu Ala Ser Leu Leu Leu Val Thr Leu
               225                 230                 235                 240
Asp Pro Arg Leu Cys His Pro Leu Ala Arg Pro Arg Arg Asp Ala Glu Pro Val Leu Gly
               245                 250                 255                 260
Gly Gly Pro Gly Gly Ala Cys Arg Ala Arg Arg Leu Tyr Val Ser Phe Arg Glu Val Gly
               265                 270                 275                 280
Trp His Arg Trp Val Ile Ala Pro Arg Gly Phe Leu Ala Asn Tyr Cys Gln Gly Gln Cys
               285                 290                 295                 300
Ala Leu Pro Val Ala Leu Ser Gly Ser Gly Gly Pro Pro Ala Leu Asn His Ala Val Leu
               305                 310                 315                 320
Arg Ala Leu Met His Ala Ala Ala Pro Gly Ala Ala Asp Leu Pro Cys Cys Val Pro Ala
               325                 330                 335                 340
Arg Leu Ser Pro Ile Ser Val Leu Phe Phe Asp Asn Ser Asp Asn Val Val Leu Arg Gln
               345                 350                 355                 360
Tyr Glu Asp Met Val Val Asp Glu Cys Gly Cys Arg
               365                 370
```

SEQ ID NO: 14    Drosophila 60A amino acid sequence

```
Met Ser Gly Leu Arg Asn Thr Ser Glu Ala Val Ala Val Leu Ala Ser Leu Gly Leu Gly Met Val
1               5                   10                  15                  20
Leu Leu Met Phe Val Ala Thr Thr Pro Pro Ala Val Glu Ala Thr Gln Ser Gly Ile Tyr Ile Asp
            25                  30                  35                  40
Asn Gly Lys Asp Gln Thr Ile Met His Arg Val Leu Ser Glu Asp Lys Leu Asp Val Ser Tyr
45                  50                  55                  60                  65
Glu Ile Leu Glu Phe Leu Gly Ile Ala Glu Arg Pro Thr His Leu Ser Ser His Gln Leu Ser Leu
                70                  75                  80                  85
Arg Lys Ser Ala Pro Lys Phe Leu Leu Asp Val Tyr His Arg Ile Thr Ala Glu Glu Gly Leu Ser
    90                  95                  100                 105                 110
Asp Gln Asp Glu Asp Asp Tyr Glu Arg Gly His Arg Ser Arg Arg Ser Ala Asp Leu Glu Glu
                115                 120                 125                 130
Asp Glu Gly Glu Gln Gln Lys Asn Phe Ile Thr Asp Leu Asp Lys Arg Ala Ile Asp Glu Ser Asp
        135                 140                 145                 150
Ile Ile Met Thr Phe Leu Asn Lys Arg His His Asn Val Asp Glu Leu Arg His Glu His Gly Arg
155                 160                 165                 170                 175
Arg Leu Trp Phe Asp Val Ser Asn Val Pro Asn Asp Asn Tyr Leu Val Met Ala Glu Leu Arg Ile
            180                 185                 190                 195
Tyr Gln Asn Ala Asn Glu Gly Lys Trp Leu Thr Ala Asn Arg Glu Phe Thr Ile Thr Val Tyr Ala
    200                 205                 210                 215                 220
Ile Gly Thr Gly Thr Leu Gly Gln His Thr Met Glu Pro Leu Ser Ser Val Asn Thr Thr Gly Asp
                225                 230                 235                 240
Tyr Val Gly Trp Leu Glu Leu Asn Val Thr Glu Gly Leu His Glu Trp Leu Val Lys Ser Lys Asp
            245                 250                 255                 260
Asn His Gly Ile Tyr Ile Gly Ala His Ala Val Asn Arg Pro Asp Arg Glu Val Lys Leu Asp Asp
265                 270                 275                 280                 285
Ile Gly Leu Ile His Arg Lys Val Asp Asp Glu Phe Gln Pro Phe Met Ile Gly Phe Phe Arg Gly
            290                 295                 300                 305
Pro Glu Leu Ile Lys Ala Thr Ala His Ser Ser His His Arg Ser Lys Arg Ser Ala Ser His Pro
    310                 315                 320                 325                 330
Arg Lys Arg Lys Lys Ser Val Ser Pro Asn Asn Val Pro Leu Leu Glu Pro Met Glu Ser Thr Arg
                335                 340                 345                 350
Ser Cys Gln Met Gln Thr Leu Tyr Ile Asp Phe Lys Asp Leu Gly Trp His Asp Trp Ile Ile Ala
            355                 360                 365                 370
Pro Glu Gly Tyr Gly Ala Phe Tyr Cys Ser Gly Glu Cys Asn Phe Pro Leu Asn Ala His Met Asn
375                 380                 385                 390                 395
Ala Thr Asn His Ala Ile Val Gln Thr Leu Val His Leu Leu Glu Pro Lys Lys Val Pro Lys Pro
            400                 405                 410                 415
Cys Cys Ala Pro Thr Arg Leu Gly Ala Leu Pro Val Leu Tyr His Leu Asn Asp Glu Asn Val Asn
    420                 425                 430                 435                 440
Leu Lys Lys Tyr Arg Asn Met Ile Val Lys Ser Cys Gly Cys His
                445                 450                 455
```

Figure 26

SEQ ID NO: 15　　　Human BMP5 amino acid sequence

Met His Leu Thr Val Phe Leu Leu Lys Gly Ile Val Gly Phe Leu Trp Ser Cys Trp Val Leu Val
 1            5                    10                      15                      20

Gly Tyr Ala Lys Gly Gly Leu Gly Asp Asn His Val His Ser Ser Phe Ile Tyr Arg Arg Leu Arg
            25                      30                      35                      40

Asn His Glu Arg Arg Glu Ile Gln Arg Glu Ile Leu Ser Ile Leu Gly Leu Pro His Arg Pro Arg
 45                      50                      55                      60                      65

Pro Phe Ser Pro Gly Lys Gln Ala Ser Ser Ala Pro Leu Phe Met Leu Asp Leu Tyr Asn Ala Met
                70                      75                      80                      85

Thr Asn Glu Glu Asn Pro Glu Glu Ser Glu Tyr Ser Val Arg Ala Ser Leu Ala Glu Glu Thr Arg
     90                      95                      100                     105                     110

Gly Ala Arg Lys Gly Tyr Pro Ala Ser Pro Asn Gly Tyr Pro Arg Arg Ile Gln Leu Ser Arg Thr
               115                      120                     125                     130

Thr Pro Leu Thr Thr Gln Ser Pro Pro Leu Ala Ser Leu His Asp Thr Asn Phe Leu Asn Asp Ala
               135                     140                     145                     150

Asp Met Val Met Ser Phe Val Asn Leu Val Glu Arg Asp Lys Asp Phe Ser His Gln Arg Arg His
 155                     160                     165                     170                     175

Tyr Lys Glu Phe Arg Phe Asp Leu Thr Gln Ile Pro His Gly Glu Ala Val Thr Ala Ala Glu Phe
               180                     185                     190                     195

Arg Ile Tyr Lys Asp Arg Ser Asn Asn Arg Phe Glu Asn Glu Thr Ile Lys Ile Ser Ile Tyr Gln
 200                     205                     210                     215                     220

Ile Ile Lys Glu Tyr Thr Asn Arg Asp Ala Asp Leu Phe Leu Leu Asp Thr Arg Lys Ala Gln Ala
               225                     230                     235                     240

Leu Asp Val Gly Trp Leu Val Phe Asp Ile Thr Val Thr Ser Asn His Trp Val Ile Asn Pro Gln
               245                     250                     255                     260

Asn Asn Leu Gly Leu Gln Leu Cys Ala Glu Thr Gly Asp Gly Arg Ser Ile Asn Val Lys Ser Ala
 265                     270                     275                     280                     285

Gly Leu Val Gly Arg Gln Gly Pro Gln Ser Lys Gln Pro Phe Met Val Ala Phe Phe Lys Ala Ser
               290                     295                     300                     305

Glu Val Leu Leu Arg Ser Val Arg Ala Ala Asn Lys Arg Lys Asn Gln Asn Arg Asn Lys Ser Ser
     310                     315                     320                     325                     330

Ser His Gln Asp Ser Ser Arg Met Ser Ser Val Gly Asp Tyr Asn Thr Ser Glu Gln Lys Gln Ala
               335                     340                     345                     350

Cys Lys Lys His Glu Leu Tyr Val Ser Phe Arg Asp Leu Gly Trp Gln Asp Trp Ile Ile Ala Pro
               355                     360                     365                     370

Glu Gly Tyr Ala Ala Phe Tyr Cys Asp Gly Glu Cys Ser Phe Pro Leu Asn Ala His Met Asn Ala
 375                     380                     385                     390                     395

Thr Asn His Ala Ile Val Gln Thr Leu Val His Leu Met Phe Pro Asp His Val Pro Lys Pro Cys
               400                     405                     410                     415

Cys Ala Pro Thr Lys Leu Asn Ala Ile Ser Val Leu Tyr Phe Asp Asp Ser Ser Asn Val Ile Leu
     420                     425                     430                     435                     440

Lys Lys Tyr Arg Asn Met Val Val Arg Ser Cys Gly Cys His
               445                     450

Figure 27

SEQ ID NO: 16    Human BMP6 amino acid sequence

```
Met Pro Gly Leu Gly Arg Arg Ala Gln Trp Leu Cys Trp Trp Trp Gly Leu Leu Cys Ser Cys Cys
 1           5                  10                 15                 20
Gly Pro Pro Pro Leu Arg Pro Pro Leu Pro Ala Ala Ala Ala Ala Ala Ala Gly Gly Gln Leu Leu
            25                 30                 35                 40
Gly Asp Gly Gly Ser Pro Gly Arg Thr Glu Gln Pro Pro Pro Ser Pro Gln Ser Ser Ser Gly Phe
 45                 50                 55                 60                 65
Leu Tyr Arg Arg Leu Lys Thr Gln Glu Lys Arg Glu Met Gln Lys Glu Ile Leu Ser Val Leu Gly
            70                 75                 80                 85
Leu Pro His Arg Pro Arg Pro Leu His Gly Leu Gln Gln Pro Gln Pro Pro Ala Leu Arg Gln Gln
 90                 95                 100                105                110
Glu Glu Gln Gln Gln Gln Gln Gln Leu Pro Arg Gly Glu Pro Pro Pro Gly Arg Leu Lys Ser Ala
            115                120                125                130
Pro Leu Phe Met Leu Asp Leu Tyr Asn Ala Leu Ser Ala Asp Asn Asp Glu Asp Gly Ala Ser Glu
135                140                145                150
Gly Glu Arg Gln Gln Ser Trp Pro His Glu Ala Ala Ser Ser Ser Gln Arg Arg Gln Pro Pro Pro
155                160                165                170                175
Gly Ala Ala His Pro Leu Asn Arg Lys Ser Leu Leu Ala Pro Gly Ser Gly Ser Gly Gly Ala Ser
            180                185                190                195
Pro Leu Thr Ser Ala Gln Asp Ser Ala Phe Leu Asn Asp Ala Asp Met Val Met Ser Phe Val Asn
200                205                210                215                220
Leu Val Glu Tyr Asp Lys Glu Phe Ser Pro Arg Gln Arg His His Lys Glu Phe Lys Phe Asn Leu
            225                230                235                240
Ser Gln Ile Pro Glu Gly Glu Val Val Thr Ala Ala Glu Phe Arg Ile Tyr Lys Asp Cys Val Met
            245                250                255                260
Gly Ser Phe Lys Asn Gln Thr Phe Leu Ile Ser Ile Tyr Gln Val Leu Gln Glu His Gln His Arg
265                270                275                280                285
Asp Ser Asp Leu Phe Leu Leu Asp Thr Arg Val Val Trp Ala Ser Glu Glu Gly Trp Leu Glu Phe
            290                295                300                305
Asp Ile Thr Ala Thr Ser Asn Leu Trp Val Val Thr Pro Gln His Asn Met Gly Leu Gln Leu Ser
            310                315                320                325                330
Val Val Thr Arg Asp Gly Val His Val His Pro Arg Ala Ala Gly Leu Val Gly Arg Asp Gly Pro
            335                340                345                350
Tyr Asp Lys Gln Pro Phe Met Val Ala Phe Phe Lys Val Ser Glu Val His Val Arg Thr Thr Arg
            355                360                365                370
Ser Ala Ser Ser Arg Arg Arg Gln Gln Ser Arg Asn Arg Ser Thr Gln Ser Gln Asp Val Ala Arg
375                380                385                390                395
Val Ser Ser Ala Ser Asp Tyr Asn Ser Ser Glu Leu Lys Thr Ala Cys Arg Lys His Glu Leu Tyr
            400                405                410                415
Val Ser Phe Gln Asp Leu Gly Trp Gln Asp Trp Ile Ile Ala Pro Lys Gly Tyr Ala Ala Asn Tyr
420                425                430                435                440
Cys Asp Gly Glu Cys Ser Phe Pro Leu Asn Ala His Met Asn Ala Thr Asn His Ala Ile Val Gln
            445                450                455                460
Thr Leu Val His Leu Met Asn Pro Glu Tyr Val Pro Lys Pro Cys Cys Ala Pro Thr Lys Leu Asn
            465                470                475                480
Ala Ile Ser Val Leu Tyr Phe Asp Asp Asn Ser Asn Val Ile Leu Lys Lys Tyr Arg Asn Met Val
485                490                495                500                505
Val Arg Ala Cys Gly Cys His
            510
```

Figure 28

SEQ ID NO: 17    full-length Human OP-1 cDNA sequence

```
gggcgcagcg gggcccgtct gcagcaagtg accgacggcc gggacggccg cctgccccct    60
ctgccacctg gggcggtgcg ggcccggagc ccggagcccg gtagcgcgt  agagccggcg   120
cgatgcacgt gcgctcactg cgagctgcgg cgccgcacag cttcgtggcg ctctgggcac   180
ccctgttcct gctgcgctcc gccctggccg acttcagcct ggacaacgag gtgcactcga   240
gcttcatcca ccggcgcctc cgcagccagg agcggcggga gatgcagcgc gagatcctct   300
ccattttggg cttgccccac cgcccgcgcc cgcacctcca gggcaagcac aactcggcac   360
ccatgttcat gctggacctg tacaacgcca tggcggtgga ggagggcggc gggcccggcg   420
gccagggctt ctcctacccc tacaaggccg tcttcagtac ccagggcccc cctctggcca   480
gcctgcaaga tagccatttc ctcaccgacg ccgacatggt catgagcttc gtcaacctcg   540
tggaacatga caaggaattc ttccacccac gctaccacca tcgagagttc cggtttgatc   600
tttccaagat cccagaaggg gaagctgtca cggcagccga attccggatc tacaaggact   660
acatccggga acgcttcgac aatgagacgt tccggatcag cgtttatcag gtgctccagg   720
agcacttggg cagggaatcg gatctcttcc tgctcgacag ccgtaccctc tgggcctcgg   780
aggagggctg gctggtgttt gacatcacag ccaccagcaa ccactgggtg gtcaatccgc   840
ggcacaacct gggcctgcag ctctcggtgg agacgctgga tgggcagagc atcaaccccca   900
agttggcggg cctgattggg cggcacgggc cccagaacaa gcagcccttc atggtggctt   960
tcttcaaggc cacggaggtc cacttccgca gcatccggtc cacggggagc aaacagcgca  1020
gccagaaccg ctccaagacg cccaagaacc aggaagccct gcggatggcc aacgtggcag  1080
agaacagcag cagcgaccag aggcaggcct gtaagaagca cgagctgtat gtcagcttcc  1140
gagacctggg ctggcaggac tggatcatcg cgcctgaagg ctacgccgcc tactactgtg  1200
agggggagtg tgccttccct ctgaactcct acatgaacgc caccaaccac gccatcgtgc  1260
agacgctggt ccacttcatc aacccggaaa cggtgcccaa gccctgctgt gcgcccacgc  1320
agctcaatgc catctccgtc ctctacttcg atgacagctc caacgtcatc ctgaagaaat  1380
acagaaacat ggtggtccgg gcctgtggct gccactagct cctccgagaa ttcagaccct  1440
ttggggccaa gttttctgg atcctccatt gctcgccttg gccaggaacc agcagaccaa  1500
ctgccttttg tgagaccttc ccctccctat ccccaacttt aaaggtgtga gagtattagg  1560
aaacatgagc agcatatggc ttttgatcag tttttcagtg gcagcatcca atgaacaaga  1620
tcctacaagc tgtgcaggca aaacctagca ggaaaaaaaa acaacgcata agaaaaatg   1680
gccgggccag gtcattggct gggaagtctc agccatgcac ggactcgttt ccagaggtaa  1740
ttatgagcgc ctaccagcca ggccacccag ccgtgggagg aagggggcgt ggcaagggt   1800
gggcacattg gtgtctgtgc gaaaggaaaa ttgacccgga gttcctgta  ataaatgtca  1860
caataaaacg aatgaatg                                                1878
```

SEQ ID NO: 18    full-length Mouse OP-1 cDNA sequence

```
ctgcagcaag tgacctcggg tcgtggaccg ctgccctgcc ccctccgctg ccacctgggg    60
cggcgcgggc ccggtgcccc ggatcgcgcg tagagccggc gcgatgcacg tgcgctcgct   120
gcgcgctgcg gcgccacaca gcttcgtggc gctctgggcg cctctgttct tgctgcgctc   180
cgccctggcc gatttcagcc tggacaacga ggtgcactcc agcttcatcc accggcgcct   240
ccgcagccag gagcggcggg agatgcagcg ggagatcctg tccatcttag ggttgcccca   300
tcgcccgcgc ccgcacctcc agggaaagca taattcggcg cccatgttca tgttggacct   360
gtacaacgcc atggcggtgg aggagagcgg gccggacgga cagggcttct cctacccta   420
caaggccgtc ttcagtaccc agggcccccc tttagccagc tgcaggaca gccacttcct   480
cactgacgcc gacatggtca tgagcttcgt caacctagtg aacatgaca agaattctt    540
ccaccctcga taccaccatc gggagttccg gtttgatctt tccaagatcc cgagggcga   600
acgggtgacc gcagccgaat tcaggatcta aaggactac atccgggagc gatttgacaa   660
cgagaccttc cagatcacag tctatcaggt gctccaggag cactcaggca gggagtcgga   720
cctcttcttg ctggacagcc gcaccatctg ggcttctgag gagggctggt tggtgtttga   780
tatcacagcc accagcaacc actgggtggt caaccctcgg cacaacctgg cttacagct   840
ctctgtggag accctggatg gcagagcat caaccccaag ttggcaggcc tgattggacg   900
gcatggaccc cagaacaagc aacccttcat ggtggccttc ttcaaggcca cggaagtcca   960
tctccgtagt atccggtcca cgggggcaa gcagcgcagc cagaatcgct ccaagacgcc  1020
aaagaaccaa gaggccctga ggatggccag tgtggcagaa acagcagca gtgaccagag  1080
gcaggcctgc aagaaacatg agctgtacgt cagcttccga gaccttggct ggcaggactg  1140
gatcattgca cctgaaggct atgctgccta ctactgtgag ggagagtgcg ccttccctct  1200
gaactcctac atgaacgcca ccaaccacgc catcgtccag acactggttc acttcatcaa  1260
cccagacaca gtacccaagc cctgctgtgc gcccacccag ctcaacgcca tctctgtcct  1320
ctacttcgac gacagctcta atgtcatcct gaagaagtac agaaacatgg tggtccgggc  1380
ctgtggctgc cactagctct tcctgagacc ctgacctttg cgggccaca ccttttccaaa  1440
tcttcgatgt ctcaccatct aagtctctca ctgcccacct ggcgaggag ccaacagacc  1500
aacctctcct gagccttccc ctcacctccc caaccggaag catgtaaggg ttccagaaac  1560
ctgagcgtgc aggcagctga tgagcgccct ttccttctgg cacgtgacgg acaagatcct  1620
accagctacc acagcaaacg cctaagagca ggaaaaatgt ctgccaggaa agtgtccatt  1680
ggccacatgg cccctggcgc tctgagtctt tgaggagtaa tcgcaagcct cgttcagctg  1740
cagcagaagg aagggcttag ccagggtggg cgctggcgtc tgtgttgaag ggaaaccaag  1800
cagaagccac tgtaatgata tgtcacaata aacccatga atgaaaaaaa aaaaaaaaa   1860
aaaaaaaaaa aa                                                    1872
```

Figure 30

SEQ ID NO: 19      full-length Mouse OP-1 amino acid sequence

```
Met His Val Arg Ser Leu Arg Ala Ala Pro His Ser Phe Val Ala Leu Trp Ala Pro
 1           5               10              15                  20

Leu Phe Leu Leu Arg Ser Ala Leu Ala Asp Phe Ser Leu Asp Asn Glu Val His Ser Ser
                25              30              35                  40

Phe Ile His Arg Arg Leu Arg Ser Gln Glu Arg Arg Glu Met Gln Arg Glu Ile Leu Ser
                45              50              55                  60

Ile Leu Gly Leu Pro His Arg Pro Arg Pro His Leu Gln Gly Lys His Asn Ser Ala Pro
                65              70              75                  80

Met Phe Met Leu Asp Leu Tyr Asn Ala Met Ala Val Glu Glu Ser Gly Pro Asp Gly Gln
                85              90              95                  100

Gly Phe Ser Tyr Pro Tyr Lys Ala Val Phe Ser Thr Gln Gly Pro Pro Leu Ala Ser Leu
                105             110             115                 120

Gln Asp Ser His Phe Leu Thr Asp Ala Asp Met Val Met Ser Phe Val Asn Leu Val Glu
                125             130             135                 140

His Asp Lys Glu Phe Phe His Pro Arg Tyr His His Arg Glu Phe Arg Phe Asp Leu Ser
                145             150             155                 160

Lys Ile Pro Glu Gly Glu Arg Val Thr Ala Ala Glu Phe Arg Ile Tyr Lys Asp Tyr Ile
                165             170             175                 180

Arg Glu Arg Phe Asp Asn Glu Thr Phe Gln Ile Thr Val Tyr Gln Val Leu Gln Glu His
                185             190             195                 200

Ser Gly Arg Glu Ser Asp Leu Phe Leu Leu Asp Ser Arg Thr Ile Trp Ala Ser Glu Glu
                205             210             215                 220

Gly Trp Leu Val Phe Asp Ile Thr Ala Thr Ser Asn His Trp Val Val Asn Pro Arg His
                225             230             235                 240

Asn Leu Gly Leu Gln Leu Ser Val Glu Thr Leu Asp Gly Gln Ser Ile Asn Pro Lys Leu
                245             250             255                 260

Ala Gly Leu Ile Gly Arg His Gly Pro Gln Asn Lys Gln Pro Phe Met Val Ala Phe Phe
                265             270             275                 280

Lys Ala Thr Glu Val His Leu Arg Ser Ile Arg Ser Thr Gly Gly Lys Gln Arg Ser Gln
                285             290             295                 300

Asn Arg Ser Lys Thr Pro Lys Asn Gln Glu Ala Leu Arg Met Ala Ser Val Ala Glu Asn
                305             310             315                 320

Ser Ser Ser Asp Gln Arg Gln Ala Cys Lys Lys His Glu Leu Tyr Val Ser Phe Arg Asp
                325             330             335                 340

Leu Gly Trp Gln Asp Trp Ile Ile Ala Pro Glu Gly Tyr Ala Ala Tyr Tyr Cys Glu Gly
                345             350             355                 360

Glu Cys Ala Phe Pro Leu Asn Ser Tyr Met Asn Ala Thr Asn His Ala Ile Val Gln Thr
                365             370             375                 380

Leu Val His Phe Ile Asn Pro Asp Thr Val Pro Lys Pro Cys Cys Ala Pro Thr Gln Leu
                385             390             395                 400

Asn Ala Ile Ser Val Leu Tyr Phe Asp Asp Ser Ser Asn Val Ile Leu Lys Lys Tyr Arg
                405             410             415                 420

Asn Met Val Val Arg Ala Cys Gly Cys His
                425             430
```

Figure 31

SEQ ID NO: 20    full-length Human OP-2 cDNA sequence

```
ccacagtggc gccggcagag caggagtggc tggaggagct gtggttggag caggaggtgg      60
cacggcaggg ctggagggct ccctatgagt ggcggagacg cccaggagg cgctggagca     120
acagctccca caccgcacca agcggtggct gcaggagctc gcccatcgcc ctgcgctgc     180
tcggaccgcg gccacagccg gactggcggg tacgcggcg acagacggat tggccgagag     240
tcccagtccg cagagtagcc ccggcctcga ggcggtggcg tcccggtcct ctccgtccag     300
gagccaggac aggtgtcgcg cggcggggct ccagggaccg cgcctgaggc cggctgcccg     360
cccgtcccgc cccgccccgc cgcccgccgc ccgccgagcc cagcctcctt gccgtcgggg     420
cgtcccagg ccctgggtcg gccgcggagc cgatgcgcgc ccgctgagcg ccccagctga     480
gcgccccgg cctgccatga ccgcgctccc cggcccgctc tggctcctgg gcctggcgct     540
atgcgcgctg gcgggggcg gccccggcct gcgaccccg cccggctgtc cccagcgacg     600
tctgggcgcg cgcgagcgcc gggacgtgca gcgcgagatc ctggcggtgc tcgggctgcc     660
tgggcggccc cggccccgcg cgccacccgc cgcctcccgg ctgccgcgt ccgcgccgct     720
cttcatgctg gacctgtacc acgccatggc cggcgacgac gacgaggacg cgcgcccgc     780
ggagcggcgc ctgggccgcg ccgacctggt catgagcttc gttaacatgg tggagcgaga     840
ccgtgccctg ggccaccagg agccccattg aaggagttc cgctttgacc tgacccagat     900
cccggctggg gaggcggtca cagctgcgga gttccggatt tacaaggtgc ccagcatcca     960
cctgctcaac aggaccctcc acgtcagcat gttccaggtg gtccaggagc agtccaacag    1020
ggagtctgac ttgttctttt tggatcttca gacgctccga gctggagacg agggctggct    1080
ggtgctggat gtcacagcag ccagtgactg ctggttgctg aagcgtcaca aggacctggg    1140
actccgcctc tatgtggaga ctgaggacgg gcacagcgtg atcctggcc tggccggcct    1200
gctgggtcaa cgggccccac gctcccaaca gcctttcgtg gtcactttct tcagggccag    1260
tccgagtccc atccgcaccc tcgggcagt gaggccactg aggaggaggc agccgaagaa    1320
aagcaacgag ctgccgcagg ccaaccgact cccagggatc tttgatgacg tccacggctc    1380
ccacggccgg caggtctgcc gtcggcacga gctctacgtc agcttccagg acctcggctg    1440
gctggactgg gtcatcgctc ccaaggcta ctcggcctat tactgtgagg gggagtgctc    1500
cttccactg gactcctgca tgaatgccac caaccacgcc atcctgcagt ccctggtgca    1560
cctgatgaag ccaaacgcag tccccaaggc gtgctgtgca cccaccaagc tgagcgccac    1620
ctctgtgctc tactatgaca gcagcaacaa cgtcatcctg cgcaagcacc gcaacatggt    1680
ggtcaaggcc tgcggctgcc actgagtcag cccgcccagc cctactgcag ccacccttct    1740
catctggatc gggccctgca gaggcagaaa acccttaaat gctgtcacag ctcaagcagg    1800
agtgtcaggg gccctcactc tctgtgccta cttcctgtca gg                       1842
```

Figure 32

SEQ ID NO: 21    full-length Human OP-2 amino acid sequence

```
Met Thr Ala Leu Pro Gly Pro Leu Trp Leu Leu Gly Leu Ala Leu Cys Ala Leu Gly Gly
 1               5                  10                 15                  20
Gly Gly Pro Gly Leu Arg Pro Pro Pro Gly Cys Pro Gln Arg Arg Leu Gly Ala Arg Glu
                25                  30                 35                  40
Arg Arg Asp Val Gln Arg Glu Ile Leu Ala Val Leu Gly Leu Pro Gly Arg Pro Arg Pro
                45                  50                 55                  60
Arg Ala Pro Pro Ala Ala Ser Arg Leu Pro Ala Ser Ala Pro Leu Phe Met Leu Asp Leu
                65                  70                 75                  80
Tyr His Ala Met Ala Gly Asp Asp Asp Glu Asp Gly Ala Pro Ala Glu Arg Arg Leu Gly
                85                  90                 95                 100
Arg Ala Asp Leu Val Met Ser Phe Val Asn Met Val Glu Arg Asp Arg Ala Leu Gly His
               105                 110                115                 120
Gln Glu Pro His Trp Lys Glu Phe Arg Phe Asp Leu Thr Gln Ile Pro Ala Gly Glu Ala
               125                 130                135                 140
Val Thr Ala Ala Glu Phe Arg Ile Tyr Lys Val Pro Ser Ile His Leu Leu Asn Arg Thr
               145                 150                155                 160
Leu His Val Ser Met Phe Gln Val Val Gln Glu Gln Ser Asn Arg Glu Ser Asp Leu Phe
               165                 170                175                 180
Phe Leu Asp Leu Gln Thr Leu Arg Ala Gly Asp Glu Gly Trp Leu Val Leu Asp Val Thr
               185                 190                195                 200
Ala Ala Ser Asp Cys Trp Leu Leu Lys Arg His Lys Asp Leu Gly Leu Arg Leu Tyr Val
               205                 210                215                 220
Glu Thr Glu Asp Gly His Ser Val Asp Pro Gly Leu Ala Gly Leu Leu Gly Gln Arg Ala
               225                 230                235                 240
Pro Arg Ser Gln Gln Pro Phe Val Val Thr Phe Phe Arg Ala Ser Pro Ser Pro Ile Arg
               245                 250                255                 260
Thr Pro Arg Ala Val Arg Pro Leu Arg Arg Arg Gln Pro Lys Lys Ser Asn Glu Leu Pro
               265                 270                275                 280
Gln Ala Asn Arg Leu Pro Gly Ile Phe Asp Asp Val His Gly Ser His Gly Arg Gln Val
               285                 290                295                 300
Cys Arg Arg His Glu Leu Tyr Val Ser Phe Gln Asp Leu Gly Trp Leu Asp Trp Val Ile
               305                 310                315                 320
Ala Pro Gln Gly Tyr Ser Ala Tyr Tyr Cys Glu Gly Glu Cys Ser Phe Pro Leu Asp Ser
               325                 330                335                 340
Cys Met Asn Ala Thr Asn His Ala Ile Leu Gln Ser Leu Val His Leu Met Lys Pro Asn
               345                 350                355                 360
Ala Val Pro Lys Ala Cys Cys Ala Pro Thr Lys Leu Ser Ala Thr Ser Val Leu Tyr Tyr
               365                 370                375                 380
Asp Ser Ser Asn Asn Val Ile Leu Arg Lys His Arg Asn Met Val Val Lys Ala Cys Gly
               385                 390                395                 400
Cys His
```

Figure 33

SEQ ID NO: 22    full-length Mouse OP-2 cDNA sequence

```
gccaggcaca ggtgcgccgt ctggtcctcc ccgtctggcg tcagccgagc ccgaccagct      60
accagtggat gcgcgccggc tgaaagtccg agatggctat gcgtcccggg ccactctggc     120
tattgggcct tgctctgtgc gcgctgggag gcggccacgg tccgcgtccc cgcacacct      180
gtccccagcg tcgcctggga gcgcgcgagc gccgcgacat gcagcgtgaa atcctggcgg     240
tgctcgggct accgggacgg ccccgacccc gtgcacaacc cgccgctgcc cggcagccag     300
cgtccgcgcc cctcttcatg ttggacctat accacgccat gaccgatgac gacgacggcg     360
ggccaccaca ggctcactta ggccgtgccg acctggtcat gagcttcgtc aacatggtgg     420
aacgcgaccg taccctgggc taccaggagc cacactggaa ggaattccac tttgacctaa     480
cccagatccc tgctggggag ctgtcacag ctgctgagtt ccggatctac aagaaccca      540
gcacccaccc gctcaacaca accctccaca tcagcatgtt cgaagtggtc caagagcact     600
ccaacaggga gtctgacttg ttcttttttgg atcttcagac gctccgatct ggggacgagg     660
gctggctggt gctggacatc acagcagcca gtgaccgatg gctgctgaac atcacaagg      720
acctgggact ccgcctctat gtggaaaccg cggatgggca cagcatggat cctggcctgg     780
ctggtctgct tggacgacaa gcaccacgct ccagacagcc tttcatggta accttcttca     840
gggccagcca gagtcctgtg cgggcccctc gggcagcgag accactgaag aggaggcagc     900
caaagaaaac gaacgagctt ccgcacccca acaaactccc agggatcttt gatgatggcc     960
acggttcccg cggcagagag gtttgccgca ggcatgagct ctacgtcagc ttccgtgacc    1020
ttggctggct ggactgggtc atcgccccccc agggctactc tgcctattac tgtgagggg     1080
agtgtgcttt cccactggac tcctgtatga acgccaccaa ccatgccatc ttgcagtctc    1140
tggtgcacct gatgaagcca gatgttgtcc ccaaggcatg ctgtgcaccc accaaactga    1200
gtgccacctc tgtgctgtac tatgacagca gcaacaatgt catcctgcgt aaacaccgta    1260
acatggtggt caaggcctgt ggctgccact gaggccccgc ccagcatcct gcttctacta    1320
ccttaccatc tggccgggcc cctctccaga ggcagaaacc cttctatgtt atcatagctc    1380
agacagggc aatgggaggc ccttcacttc ccctggccac ttcctgctaa aattctggtc    1440
tttcccagtt cctctgtcct tcatggggtt tcgggctat caccccgccc tctccatcct     1500
cctaccccaa gcatagactg aatgcacaca gcatcccaga gctatgctaa ctgagaggtc    1560
tggggtcagc actgaaggcc cacatgagga agactgatcc ttggccatcc tcagcccaca    1620
atggcaaatt ctggatggtc taagaagccc tggaattcta aactagatga tctgggctct    1680
ctgcaccatt cattgtggca gttgggacat ttttaggtat aacagacaca tacacttaga    1740
tcaatgcatc gctgtactcc ttgaaatcag agctagcttg ttagaaaaag aatcagagcc    1800
aggtatagcg gtgcatgtca ttaatcccag cgctaaagag acagagacag gagaatctct    1860
gtgagttcaa ggccacatag aaagagcctg tctcgggagc aggaaaaaaa aaaaaaa      1917
```

Figure 34

SEQ ID NO: 23    full-length Mouse OP-2 amino acid sequence

```
Met Ala Met Arg Pro Gly Pro Leu Trp Leu Leu Gly Leu Ala Leu Cys Ala Leu Gly Gly
 1               5                  10                 15                  20
Gly His Gly Pro Arg Pro Pro His Thr Cys Pro Gln Arg Arg Leu Gly Ala Arg Glu Arg
                25                  30                 35                  40
Arg Asp Met Gln Arg Glu Ile Leu Ala Val Leu Gly Leu Pro Gly Arg Pro Arg Pro Arg
                45                  50                 55                  60
Ala Gln Pro Ala Ala Ala Arg Gln Pro Ala Ser Ala Pro Leu Phe Met Leu Asp Leu Tyr
                65                  70                 75                  80
His Ala Met Thr Asp Asp Asp Gly Gly Pro Pro Gln Ala His Leu Gly Arg Ala Asp
                85                  90                 95                 100
Leu Val Met Ser Phe Val Asn Met Val Glu Arg Asp Arg Thr Leu Gly Tyr Gln Glu Pro
               105                 110                115                 120
His Trp Lys Glu Phe His Phe Asp Leu Thr Gln Ile Pro Ala Gly Glu Ala Val Thr Ala
               125                 130                135                 140
Ala Glu Phe Arg Ile Tyr Lys Glu Pro Ser Thr His Pro Leu Asn Thr Thr Leu His Ile
               145                 150                155                 160
Ser Met Phe Glu Val Val Gln Glu His Ser Asn Arg Glu Ser Asp Leu Phe Phe Leu Asp
               165                 170                175                 180
Leu Gln Thr Leu Arg Ser Gly Asp Glu Gly Trp Leu Val Leu Asp Ile Thr Ala Ala Ser
               185                 190                195                 200
Asp Arg Trp Leu Leu Asn His His Lys Asp Leu Gly Leu Arg Leu Tyr Val Glu Thr Ala
               205                 210                215                 220
Asp Gly His Ser Met Asp Pro Gly Leu Ala Gly Leu Leu Gly Arg Gln Ala Pro Arg Ser
               225                 230                235                 240
Arg Gln Pro Phe Met Val Thr Phe Phe Arg Ala Ser Gln Ser Pro Val Arg Ala Pro Arg
               245                 250                255                 260
Ala Ala Arg Pro Leu Lys Arg Arg Gln Pro Lys Lys Thr Asn Glu Leu Pro His Pro Asn
               265                 270                275                 280
Lys Leu Pro Gly Ile Phe Asp Asp Gly His Gly Ser Arg Gly Arg Glu Val Cys Arg Arg
               285                 290                295                 300
His Glu Leu Tyr Val Ser Phe Arg Asp Leu Gly Trp Leu Asp Trp Val Ile Ala Pro Gln
               305                 310                315                 320
Gly Tyr Ser Ala Tyr Tyr Cys Glu Gly Glu Cys Ala Phe Pro Leu Asp Ser Cys Met Asn
               325                 330                335                 340
Ala Thr Asn His Ala Ile Leu Gln Ser Leu Val His Leu Met Lys Pro Asp Val Val Pro
               345                 350                355                 360
Lys Ala Cys Cys Ala Pro Thr Lys Leu Ser Ala Thr Ser Val Leu Tyr Tyr Asp Ser Ser
               365                 370                375                 380
Asn Asn Val Ile Leu Arg Lys His Arg Asn Met Val Val Lys Ala Cys Gly Cys His
               385                 390                395
```

Figure 35

SEQ ID NO: 24    Generic sequence No. 1

|     |     |     | Leu 1 | Tyr | Val | Ser | Phe 5 | Xaa | Asp |
| --- | --- | --- | --- | --- | --- | --- | --- | --- | --- |
| Xaa | Gly | Trp 10 | Gln | Asp | Trp | Ile | Ile 15 | Ala | Pro |
| Xaa | Gly | Tyr 20 | Ala | Ala | Xaa | Tyr | Cys 25 | Xaa | Gly |
| Glu | Cys | Xaa 30 | Phe | Pro | Leu | Asn | Xaa 35 | Xaa | Met |
| Asn | Ala | Thr 40 | Asn | His | Ala | Ile | Val 45 | Gln | Thr |
| Leu | Val | His 50 | Xaa | Xaa | Xaa | Pro | Xaa 55 | Xaa | Val |
| Pro | Lys | Pro 60 | Cys | Cys | Ala | Pro | Thr 65 | Xaa | Xaa |
| Asn | Ala | Ile 70 | Ser | Val | Leu | Tyr | Phe 75 | Asp | Asp |
| Xaa | Ser | Asn 80 | Val | Ile | Leu | Lys | Lys 85 | Tyr | Arg |
| Xaa | Met | Val | Val | Arg | Xaa | Cys | Gly | Cys | His |

Figure 36

BMP-7 FOR USE IN TREATING NEOINTIMAL HYPERPLASIA

This application is a national stage filing under 35 U.S.C. §371 of International Application PCT/US2009/034069, filed Feb. 13, 2009, which claims the benefit of U.S. Provisional Application 61/028,499, filed Feb. 13, 2008. The entire disclosure of each of these referenced applications is incorporated herein by reference.

GOVERNMENT FUNDING

This work was supported by NIH grants DK059602, DK070790 and AR41677, with Keith A. Hruska as the principal investigator.

The Sequence Listing associated with this application is provided in text format in lieu of a paper copy, and is hereby incorporated by reference into the specification. The name of the text file containing the Sequence Listing is Sequence_listing.txt. The text file is 106,231 bytes in size, was created on Jan. 18, 2011 and is submitted electronically via EFS-Web.

FIELD OF THE INVENTION

The present invention relates to prevention and treatment of vascular sclerosis, neointimal hyperplasia and vascular calcification (VC).

BACKGROUND OF THE INVENTION

Chronic kidney disease (CKD) is a fatal illness, and cardiovascular complications (including arteriovenous (AV) access failure due to venous neointimal hyperplasia (NH) lesions) are the major causes of morbidity and mortality. (Go, A. S. et al., *New Engl. J. Med.* 351:1296-1305, 2004; Berl, T. and Henrich, W., *Clin. J. Am. Soc. Nephrol.* 1:8-18, 2006)[1;2] The causes of the excess cardiovascular mortality associated with CKD are unknown, since the role of the standard risk factors associated with cardiovascular mortality do not account for the increased risk in CKD (Berl, ibid.).

While AV fistulae constructed with native vessels are the best vascular access available, owing to a lower incidence of stenosis, thrombosis and infection compared with vascular grafts or central venous catheters, even after maturation, the failure rate of 66% at 2 years still remains unacceptable (Shenoy S, et al., *J Vasc Surg.* 2003; 38(2):229-235.)[54] and hemodialysis access related hospitalizations continue to cost well over 1 billion dollars per annum in the United States (Lee H, et al., *Am J Kidney Dis.* 2002; 40(3):611-622).[55]

The cause of AV access failure is predominantly secondary to the occlusive neointimal hyperplastic lesion formation at the anastomosis and/or the outflow veins followed by in situ thrombosis (Mattana J, et al., *Kidney Int.* 1997; 52(6):1478-1485; Ezzahiri R, et al., *Nephrol Dial Transplant.* 1999; 14(9):2110-2115; Cinat M E, et al., *Ann Vasc Surg.* 1999; 13(2):191-198; Tordoir J H, et al., *Eur J Vasc Endovasc Surg.* 1995; 9(3):305-309).[56-59] Unlike restenosis seen with preocclusive atherosclerotic arteries after angioplasty and stenting, neointimal (new intimal) hyperplasia (NH) is seen at the anastomosis involving an artery or a synthetic graft (e.g., ePTFE, Dacron) and a vein in the extremities. Although these blood vessels are usually free of atherosclerotic plaque, they are predisposed to calcification, pre-existing NH and needle stick injuries. Therefore, directional migration of smooth muscle cells (SMCs) into the venous luminal surface is critical to peri-anastomotic NH lesion formation (Roy-Chaudhury P, et al., *J Am Soc Nephrol.* 2006; 17(4):1112-1127; Nikkari S T, et al., *Ann Med.* 1994; 26(2):95-100).[60,61]

CKD has been implicated in the development of atherosclerosis along with a host of other deranged factors such as hemodynamic forces, inflammatory mediators, platelet activation, coagulation cascade and metabolic factors. Further, there is strong epidemiologic evidence that serum phosphorus is an independent risk factor for cardiovascular events and mortality in CKD (Kestenbaum, B. et al., *J. Am. Soc. Nephrol.* 16:520-528, 2005; Slinin, Y. et al., *J. Am. Soc. Nephrol.* 16:1788-1793, 2005).[3;4] Serum phosphorus has been linked to another cardiovascular risk factor, vascular calcification (VC) (Kestenbaum et al. 2005; London, G. M. et al., *Nephrol. Dial. Transplant.* 18:1731-1740, 2003; Raggi, P. et al., *J. Am. Coll. Cardiol.* 39:695-701, 2002)[3;5;6], an important cause of vascular stiffness in CKD. Vascular stiffness from various causes including CKD, atherosclerosis, metabolic diseases, and diabetes, is a major cardiovascular risk factor, leading to increased pulse wave velocity, increased cardiac work, left ventricular hypertrophy, and decreased coronary artery blood flow. (Raggi 2002; Zile, M. R. et al., *New Engl. J. Med.* 350:1953-1959, 2004; Ohtake, T. et al., *J. Am. Soc. Nephrol.* 16:1141-1148, 2005).[6-8] Phosphorus has been further implicated as a cause of VC through studies in vitro which have demonstrated that it induces phenotypic changes in vascular smooth muscle cells by increasing gene transcription of proteins involved in osteoblast function-bone formation (Tyson, K. L. et al., *Arterioscler. Thromb. Vasc. Biol.* 23:489-494, 2003)[9] and stimulating matrix mineralization (Steitz, S. A. et al., *Circ. Res.* 89:1147-1154, 2001; Jono, S. et al., *Cir. Res.* 87:e10-e17, 2000; Reynolds, J. L. et al., *J. Am. Soc. Nephrol.* 15:2857-2867, 2004)[10-12]. In the uremic calcifying environment, expression of the contractile proteins of vascular smooth muscle cells, such as α-smooth muscle actin, SM22, and heavy chain myosin, are suppressed (Trion, A. and van der Laarse, A., *Am. Heart J.* 147:808-814, 2004),[13] while osteoblastic lineage markers such as osteocalcin, osteopontin, and the bone morphogenetic proteins 2 and 4 are increased (Tyson 2003; Moe, S. M. et al., *Kidney Int'l* 61:638-647, 2002; Boström, K. et al., *J Clin. Invest.* 91:1800-1809, 1993; Dhore, C. R. et al., *Arterioscler. Thromb. Vasc. Biol.* 21:1998-2003, 2001).[9;14-16] Furthermore, the osteoblast specific transcription factor RUNX2, which directs skeletal bone formation (Ducy, P. et al., *Cell* 89:747-754, 1997),[17] is expressed in the vasculature of subjects with end stage CKD (ESKD) (Tyson 2003; Moe, S. M. et al., *Kidney Int'l* 63:1003-1011, 2003).[9;18]

An animal model of CKD-stimulated VC in the atherosclerotic low density lipoprotein receptor-deficient mouse fed high dietary fat has recently been identified (Davies, M. R. et al., *J. Am. Soc. Nephrol.* 14:1559-1567, 2003).[19] The CKD in this model is associated with hyperphosphatemia. It has been demonstrated that the hyperphosphatemia is a direct cause of VC in CKD (Davies, M. R. et al., *J. Am. Soc. Neph.* 16:917-928, 2005).[20] This was the first demonstration in vivo that hyperphosphatemia is causative of a cardiovascular complication of the disease. Furthermore, it has been demonstrated that the skeleton in CKD is a significant contributor of phosphorus to hyperphosphatemia, (Davies 2005; Lund, R, J, et al., *J. Am. Soc. Nephrol.* 15:359-369, 2004)[20;21] along with intestinal absorption of ingested phosphorus and diminished renal excretion. This establishes a direct link between skeletal remodeling and VC in CKD through the serum phosphorus. The mechanism of phosphorus action at the level of the vasculature remains to be demonstrated despite recent progress suggesting direct actions of the ion (Jono 2000; Li, X. et al., *Circ. Res.* 98:905-912, 2006).[11,22]

SUMMARY OF THE INVENTION

The instant invention relates to compositions and methods for treating or preventing vascular sclerosis. In one aspect of the invention the vascular sclerosis accompanies or is induced by CKD. The instant invention also relates to compositions and methods for inducing differentiation of vascular smooth muscle cells.

One aspect of the invention is to treat or prevent vascular sclerosis. In some embodiments, the invention provides a method of treating or preventing vascular sclerosis in a subject comprising the step of administering to said subject a morphogen selected from BMP-7, BMP-5, BMP-6, OP-2 (BMP-8) and variants thereof. In a preferred embodiment, the morphogen is BMP-7. In other embodiments, the invention provides a method of treating or preventing vascular sclerosis in a subject comprising the step of administering to said subject an antagonist of a mineralizing BMP. In certain embodiments, the mineralizing BMP is BMP-2 or BMP-4, or an analog thereof. In some embodiments, the vascular sclerosis is induced by chronic kidney disease.

Another aspect of the invention is to treat, prevent or reduce neointimal hyperplasia. In some embodiments, the invention provides a method of treating, preventing or reducing neointimal hyperplasia in a subject comprising the step of administering to said subject a morphogen selected from BMP-7, BMP-5, BMP-6, OP-2 (BMP-8) and variants thereof. In a preferred embodiment, the morphogen is BMP-7. In other embodiments, the invention provides a method of treating, preventing or reducing neointimal hyperplasia in a subject comprising the step of administering to said subject an antagonist of a mineralizing BMP. In certain embodiments, the mineralizing BMP is BMP-2 or BMP-4, or an analog thereof. In some embodiments, the neointimal hyperplasia is associated with anastomosis. In some embodiments, the neointimal hyperplasia is induced by chronic kidney disease.

Another aspect of the invention is to induce vascular smooth muscle differentiation. In some embodiments, the invention provides a method of inducing vascular smooth muscle cell differentiation comprising the step of contacting a vascular smooth muscle progenitor cell or an undifferentiated or dedifferentiated vascular smooth muscle cell, with a morphogen selected from BMP-7, BMP-5, BMP-6, OP-2 (BMP-8) and variants thereof. In a preferred embodiment, the morphogen is BMP-7. In other embodiments, the invention provides a method of inducing vascular smooth muscle cell differentiation comprising the step of contacting a vascular smooth muscle progenitor cell or an undifferentiated or dedifferentiated vascular smooth muscle cell with an antagonist of a mineralizing BMP. In certain embodiments, the mineralizing BMP is BMP-2 or BMP-4, or an analog thereof.

The instant invention further relates to preventing and decreasing established vascular sclerosis caused by calcification of blood vessels. The mechanism of a representative method for decreasing calcification is by controlling hyperphosphatemia and related phosphorus metabolism. CKD stimulates VC in part through increasing atherosclerotic calcification. Secondly, atherosclerotic calcification is due to heterotopic expression of osteoblastic differentiation and function in the vasculature. Third, hyperphosphatemia is a cardiovascular risk factor in CKD through stimulation of vascular calcification. The mechanism of phosphorus-mediated induction of vascular calcification is through its stimulation of osterix in the vascular neointima and tunica media in CKD. Phosphorus stimulated activity of osterix permitted a BMP-2/MSX2 directed program to be completed and mineralization to be stimulated.

One aspect of the invention is to prevent mineralization or to stop further mineralization and/or calcification of blood vessels by inhibiting mineralizing bone morphogenetic protein (BMP) activities. One embodiment of the invention is a method of preventing initial or further mineralization/calcification of blood vessels in the presence of phosphorus, by contacting muscle cells with an antagonist of mineralizing BMP, i.e. mineralization-countering BMP, thereby inhibiting mineralizing BMP activities. In a particular embodiment, the muscle cells are vascular smooth muscle cells. In particular embodiments, the mineralizing BMP is BMP-2 or BMP-4, or an analog thereof. In further particular embodiments, the muscle cells are aortic cells. In one embodiment, the antagonist of mineralizing BMP is noggin. In another embodiment, the antagonist of a mineralizing BMP is another BMP, such as BMP-7, or an analog thereof.

Another embodiment of the invention is a method of preventing initial or further calcification of blood vessels in the presence of phosphorus by reducing osterix activities. In certain embodiments, osterix activities are reduced by reducing the expression of osterix. In particular embodiments, the expression of osterix is reduced by reducing osterix mRNA transcription. In other embodiments, the expression of osterix is inhibited by inhibiting osterix protein translation. In other particular embodiments, osterix activities are reduced by inhibiting the activities of osterix protein directly.

Another aspect of the invention is methods of treating calcification of blood vessels by inhibiting mineralizing bone morphogenetic protein (BMP) activities. One embodiment of the invention is a method of treating established vascular mineralization by administering an antagonist of mineralizing BMP, thereby inhibiting mineralizing BMP activities. A preferred embodiment of the invention is such method of treating vascular sclerosis induced by CKD, wherein phosphorus levels in the serum are elevated. In a particular embodiment, an antagonist of mineralizing BMP activities is BMP-7 or an analog thereof.

Another aspect of the invention is a pharmaceutical composition comprising a morphogen selected from BMP-7, BMP-5, BMP-6, OP-2 (BMP-8) and variants thereof for treating or preventing vascular sclerosis in a subject. In a preferred embodiment, the morphogen is BMP-7. Another aspect of the invention is a pharmaceutical composition comprising an antagonist of a mineralizing BMP for treating or preventing vascular sclerosis in a subject. In some embodiments, the mineralizing BMP is BMP-2 or BMP-4. In some embodiments, the vascular sclerosis is induced by chronic kidney disease.

Another aspect of the invention is a pharmaceutical composition comprising a morphogen selected from BMP-7, BMP-5, BMP-6, OP-2 (BMP-8) and variants thereof for treating, preventing or reducing neointimal hyperplasia in a subject. In a preferred embodiment, the morphogen is BMP-7. Another aspect of the invention is a pharmaceutical composition comprising an antagonist of a mineralizing BMP for treating, preventing or reducing neointimal hyperplasia in a subject. In some embodiments, the mineralizing BMP is BMP-2 or BMP-4. In some embodiments, the neointimal hyperplasia is associated with anastomosis. In other embodiments, the neointimal hyperplasia is induced by chronic kidney disease.

Another aspect of the invention is a pharmaceutical composition comprising a morphogen selected from BMP-7, BMP-5, BMP-6, OP-2 (BMP-8) and variants thereof for inducing differentiation of a vascular smooth muscle progenitor cell or an undifferentiated or dedifferentiated vascular smooth muscle cell. In a preferred embodiment, the morphogen is BMP-7. Another aspect of the invention is a pharmaceutical composition comprising an antagonist of a mineralizing BMP for inducing differentiation of a vascular smooth muscle progenitor cell or an undifferentiated or dedifferentiated vascular smooth muscle cell. In some embodiments, the mineralizing BMP is BMP-2 or BMP-4.

Another aspect of the invention is a pharmaceutical composition comprising a phosphorus binding agent for the treatment of hyperphosphatemia, and thus, vascular calcification. Another aspect of the invention is a pharmaceutical composition comprising a BMP inhibitor for the treatment of vascular calcification. Yet another aspect of the invention is a pharmaceutical composition comprising BMP-7 for the treatment of vascular calcification.

In any of the described aspects and embodiments of the present invention, an analog of a named BMP represents any similar BMPs having highly homologous structures, i.e., a six- or seven-cysteine skeleton which, through disulfide bonds form a distinct structure at the C-terminal portion of the polypeptide, wherein the amino acid sequence of such six- or seven-cysteine skeleton shares 70, 80, 90, or 95% similarity or identity while preserving the cysteines and wherein the biological activities may partially or wholly substitute the named BMPs.

BRIEF DESCRIPTION OF THE FIGURES

FIG. 10 shows homologies among various bone morphogenetic proteins.

FIG. 13 shows the amino acid sequence of human OP-1 (SEQ ID NO:1).

FIG. 14 shows the amino acid sequence of the conserved 6 cysteine skeleton of human OP-1 (SEQ ID NO:2).

FIG. 15 shows the amino acid sequence of morphogenically active full-length human OP-1 (SEQ ID NO:3).

FIG. 16 shows the amino acid sequence of mature mouse OP-1 (SEQ ID NO:4).

FIG. 17 shows the amino acid sequence of mature human OP-2 (SEQ ID NO:5).

FIG. 18 shows the amino acid sequence of mature mouse OP-2 (SEQ ID NO:6).

FIG. 19 shows the amino acid sequence of drosophila DPP (SEQ ID NO:7).

FIG. 20 shows the amino acid sequence of Xenopus VG1 (SEQ ID NO:8).

FIG. 21 shows the amino acid sequence of mouse Vgr-1 (SEQ ID NO:9).

FIG. 22 shows the amino acid sequence of human CBMP-2A (SEQ ID NO:10).

FIG. 23 shows the amino acid sequence of human CBMP-2B (SEQ ID NO:11).

FIG. 24 shows the amino acid sequence of human BMP-3 (SEQ ID NO:12).

FIG. 25 shows the amino acid sequence of human GDF-1 (SEQ ID NO:13).

FIG. 26 shows the amino acid sequence of drosophila 60A (SEQ ID NO:14).

FIG. 27 shows the amino acid sequence of human BMP-5 (SEQ ID NO:15).

FIG. 28 shows the amino acid sequence of human BMP-6 (SEQ ID NO:16).

FIG. 29 shows the full-length cDNA sequence of human OP-1 (SEQ ID NO:17).

FIG. 30 shows the full-length cDNA sequence of mouse OP-1 (SEQ ID NO:18).

FIG. 31 shows the amino acid sequence of full-length mouse OP-1 (SEQ ID NO:19).

FIG. 32 shows the full-length cDNA sequence of human OP-2 (SEQ ID NO:20).

FIG. 33 shows the amino acid sequence of full-length human OP-2 (SEQ ID NO:21).

FIG. 34 shows the full-length cDNA sequence of mouse OP-2 (SEQ ID NO:22).

FIG. 35 shows the amino acid sequence of full-length mouse OP-2 (SEQ ID NO:23).

FIG. 36 shows the amino acid sequence of generic sequence No. 1 (SEQ ID NO:24).

DETAILED DESCRIPTION OF THE INVENTION

Figure 1:
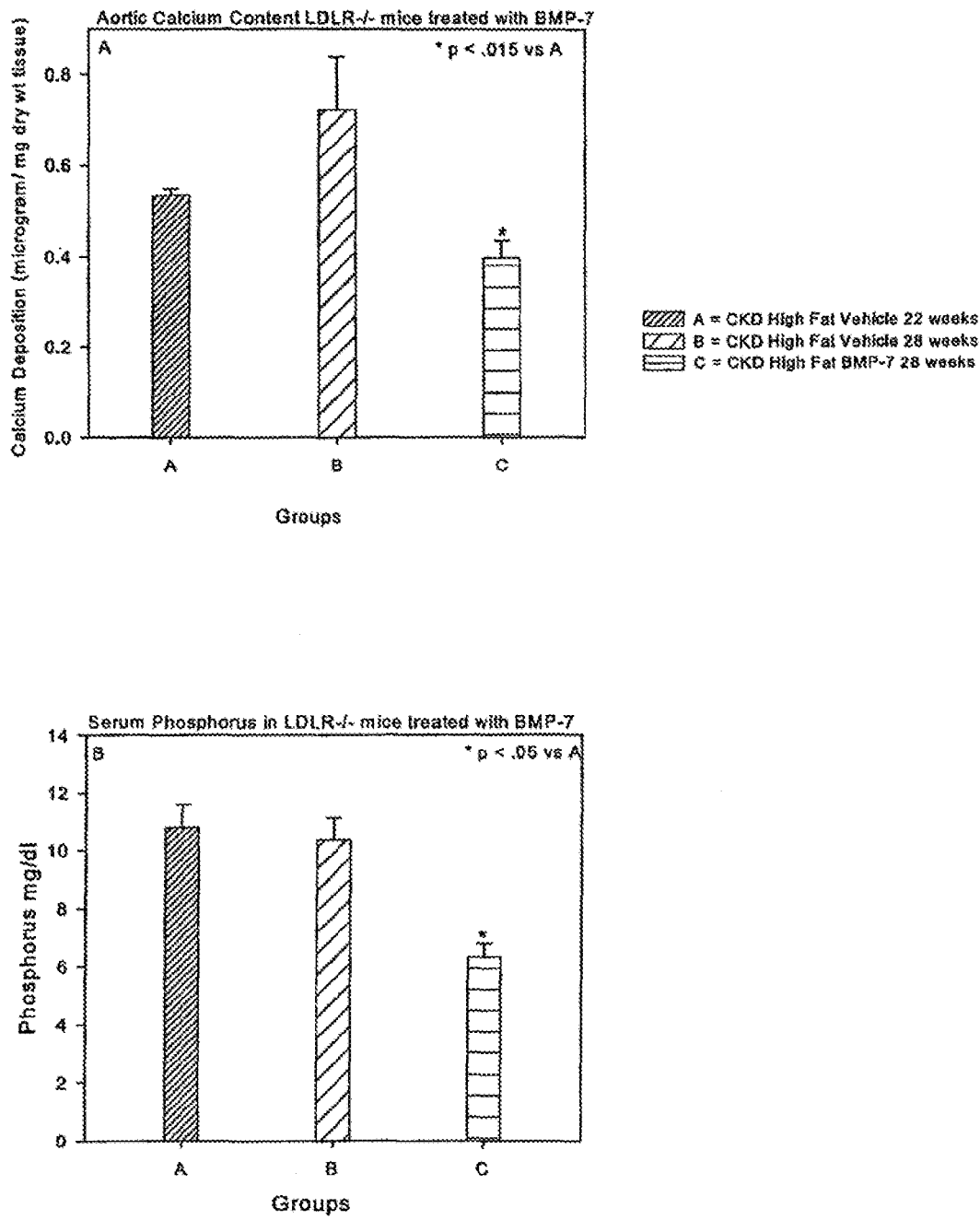
FIG. 1 shows the effects of BMP-7 on vascular calcification in CKD.

In order that the invention herein described may be fully understood, the following detailed description is set forth.

I. Definitions

Unless defined otherwise, all technical and scientific terms used herein have the same meaning as those commonly understood by one of ordinary skill in the art to which this invention belongs. Although methods and materials similar or equivalent to those described herein can be used in the practice or testing of the present invention, suitable methods and materials are described below. The materials, methods and examples are illustrative only, and are not intended to be limiting. All publications, patents and other documents mentioned herein are incorporated by reference in their entirety.

Throughout this specification, the word "comprise" or variations such as "comprises" or "comprising" will be understood to imply the inclusion of a stated integer or groups of integers but not the exclusion of any other integer or group of integers.

OP/BMP morphogen. As used herein, the terms "OP/BMP morphogen," "BMP," "OP," "morphogen," "bone morphogenic protein," and "bone morphogenetic protein" are used interchangeably and mean a polypeptide, or a functional variant of a polypeptide, comprising at least the C-terminal six- or seven-cysteine domain of a mammalian protein selected from the group consisting of BMP-7 (OP-1), OP-2 (BMP-8), OP-3, BMP2, BMP3, BMP4, BMP5, BMP6, BMP9, and "morphogen analogs." "Morphogen analogs" are defined herein as proteins which comprises the C-terminal six- or seven-cysteine skeleton (with the cysteines forming a scaffold that preserves the spatial relationships to and among each other and with other amino acid residues) and exhibit, among the amino acids in this skeleton that are not cysteines, at least 65% or, more preferably, 70%, 75% 80%, 85%, 90%, or 95% amino acid sequence homology, or at least 50%, more preferably 55%, 60%, 70%, 80%, 90%, 99% or more identity, with the amino acid sequence of the seven-cysteine domain of a morphogen of which it is an analog. A morphogen analog may be truncated at the N-terminus compared to a full-length morphogen, or may be a corresponding protein from a different species. A morphogen analog may be artificially prepared. A morphogen analog may have post-translational modification or may have been incorporated non-amino acids, or may comprise unnatural amino acids, such as D-amino acids or polysaccharides that have substantially similar conformation as the amino acid residues that they replaced. A morphogen analog may have similar biological activities as the protein of which it is an analog. Such activities are: (a) capable of inducing chondrogenesis in the Reddi-Sampath ectopic bone assay (Sampath and Reddi 1981, *Proc. Natl. Acad. Sci. (USA)* 78: 7599-7603) or a substantially equivalent assay, (b) capable of significantly preventing, inhibiting, delaying or alleviating the progressive loss of renal function in a standard animal model of chronic renal failure, or (c) capable of causing a clinically significant improvement in a standard marker of renal function when administered to a mammal in, or at risk of, chronic renal failure.

As used herein, "mineralizing bone morphogenetic protein" or "mineralizing BMP" refers to a subset of OP/BMP morphogen (as defined above) that promotes osteoblast differentiation and calcification of tissues. Examples of mineralizing BMP are BMP-2 and BMP-4, and analogs of BMP-2 and BMP-4.

As used herein, "mineralization-countering BMP" means certain BMPs, such as BMP-7, that counter the activity of mineralizing BMP and therefore hampers mineralization of tissues.

As used herein, "amino acid sequence homology" or a percentage "homology" between two amino acid sequences is understood herein to include both amino acid sequence identity and conserved substitution. Thus, as used herein, a percentage "homology" between two amino acid sequences indicates the percentage of amino acid residues which are identical or are conserved substitution between the sequences. "Conservative substitutions" of amino acids fulfill the criteria defined for an "accepted point mutation" in Dayhoff et al. (1978), Atlas of Protein Sequence and Structure Vol. 5 (Suppl. 3), pp. 354-352, Natl. Biomed. Res. Found., Washington, D.C. Thus, "conservative substitutions" are residues that are physically or functionally similar to the corresponding reference residues, having similar size, shape, electric charge, and/or chemical properties such as the ability to form covalent or hydrogen bonds, or the like. Examples of preferred conservative substitutions include the substitution of one amino acid for another with similar characteristics, e.g., substitutions within the following groups: (a) Ser, Thr, Pro, Ala, Gly; (b) Asn, Asp, Glu, Gln; (c) His, Arg, Lys; (d) Met, Ile, Leu, Val; (e) Phe, Tyr, Trp. In a most preferred embodiment, conservative substitutions include the substitution of one amino acid for another within the following groups: (a) glycine, alanine; (b) valine, isoleucine, leucine; (c) aspartic acid, glutamic acid; (d) asparagine, glutamine; (e) serine, threonine; (f) lysine, arginine, histidine; and (g) phenylalanine, tyrosine. See FIG. 84 of Dayhoff et al. (1978), Atlas of Protein Sequence and Structure Vol. 5 (Suppl. 3), pp. 354-352, Natl. Biomed. Res. Found., Washington, D.C. The term "conservative substitution" or "conservative variation" also includes the use of a substituted amino acid in place of an unsubstituted parent amino acid in a given polypeptide chain, provided that the resulting substituted polypeptide chain also has therapeutic efficacy in the present invention.

As used herein, a therapeutic agent (morphogen) of the invention is said to have "therapeutic efficacy," and an amount of the agent is said to be "therapeutically effective," if administration of that amount of the agent is sufficient to cause a clinically significant improvement in a standard marker of cardiovascular health when administered to a mammalian subject (e.g., a human patient) in, or at risk of, vascular sclerosis. Such markers of vascular sclerosis are well known in the medical literature and include, without being limited to, heart rate, heart rhythm and the results of tests such as angiography, stress testing, electrocardiogram, echocardiogram, computed tomography, heartscoring, cardiac calcification scoring, calcium scoring and heart scanning.

The phrase 'therapeutically effective amount' as used herein means that amount of a compound, material, or composition comprising a compound of the present invention which is effective for producing some desired therapeutic effect in at least a sub-population of cells in an animal and thereby blocking the biological consequences of that pathway in the treated cells, at a reasonable benefit/risk ratio applicable to any medical treatment.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" as used herein means a pharmaceutically acceptable material, composition or vehicle, such as a liquid or solid filler, diluent, excipient, solvent or encapsulating material, involved in carrying or transporting the subject compounds from one organ, or portion of the body, to another organ, or portion of the body. Each carrier must be "acceptable" in the sense of being compatible with the other ingredients of the formulation and not injurious to the patient. Some examples of materials which can serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

As used herein, "treat" or "treating" means refers to alleviating or lessening the severity of one or more symptoms associated with the recited condition, disease or disorder in a subject. The term treat or treating does not, however, mean, or otherwise necessitate, a process of complete healing or a treatment, which is 100% effective at restoring the health the subject to its pre-condition state.

As used herein, "prevent" or "prevention" means reducing the probability/risk of developing a condition in a subject (cell, tissue, organ, or organism, etc.), or delaying the onset of a condition in the subject, or to lessening the severity of one or more symptoms of a condition that may develop in the subject, or any combination thereof.

As used herein, "subject" refers to an animal. In some embodiments, the animal is a mammal, including but not limited to a human, bovine and rodent. In a preferred embodiment, the mammal is a human.

As used herein with respect to kidney disease in general and more specifically to clinical indications such as urinary casts, measured GFR, or other markers of renal function, each of which is described hereinbelow, "chronic" means persisting for a period of at least three, and more preferably, at least six months. Thus, for example, a subject with a measured GFR chronically below 50% of $GFR_{exp}$ is a subject in which the GFR has been measured and found to be below 50% of $GFR_{exp}$ in at least two measurements separated by at least three, and more preferably, by at least six months, and for which there is no medically sound reason to believe that GFR was substantially (e.g., 10%) higher during the intervening period.

As used herein, a subject is said to have vascular sclerosis if diagnostic tests indicate the presence of vascular calcification above the accepted healthy level in the view of the treating physician. A subject is said to be "at risk, of developing vascular sclerosis" if the subject is reasonably expected to develop vascular sclerosis due to the presence of one or more risk factors for vascular calcification, including renal disease, obesity, metabolic syndrome, type II diabetes, hyperlipidemia, and osteoporosis. The presence or risk of vascular sclerosis is a determination which may routinely be made by one of ordinary skill in the relevant medical or veterinary art.

A subject may be regarded as afflicted with renal disease if he or she presents with chronic renal failure, end-stage renal disease, chronic diabetic nephropathy, hypertensive nephrosclerosis, chronic glomerulonephritis, hereditary nephritis, and/or renal dysplasia; subjects having a biopsy indicating glomerular hypertrophy, tubular hypertrophy, chronic glomerulosclerosis, and/or chronic tubulointerstitial sclerosis; subjects having an ultrasound, NMR, CAT scan, or other non-invasive examination indicating renal fibrosis; subjects having an unusual number of broad casts present in urinary sediment; subjects having agar which is chronically less than about 50%, and more particularly less than about 40%, 30% or 20%, of the expected GFR for the subject; human male subjects weighing at least about 50 kg and having a GFR which is chronically less than about 50 ml/min, and more particularly less than about 40 ml/min, 30 ml/min or 20 ml/min; human female subjects weighing at least about 40 kg and having a GFR which is chronically less than about 40 ml/min, and more particularly less than about 30 ml/min, 20 ml/min or 10 ml/min; subjects possessing a number of functional nephron units which is less than about 50%, and more particularly less than about 40%, 30% or 20%, of the number of functional nephron units possessed by a healthy but otherwise similar subject; subjects which have a single kidney; and subjects which are kidney transplant recipients.

II. Overveiw

Vascular sclerosis, or hardening of blood vessels, leads to multiple related cardiovascular injuries and failures. Vascular sclerosis may manifest itself in many diseases, including renal disease, such as chronic kidney disease (CKD), atherosclerosis, metabolic disease, metabolic syndrome, obesity, osteoporosis, hypertension, type-II diabetes, etc. CDK is a complex multiorgan system failure. It is associated with high mortality rates due to cardiovascular events.

Hyperphosphatemia and vascular calcification (VC), or vascular mineralization, (these two terms are used interchangeably herein) are cardiovascular risk factors in CKD. In an animal model of atherosclerosis and type 2 diabetes, CKD has been demonstrated to stimulate hyperphosphatemia and VC. Further, disclosed herein is that hyperphosphatemia is directly linked to VC as demonstrated using this model, and that BMP-7 or intestinal phosphorus binding corrected hyperphosphatemia and decreased established VC in this model.

The present invention relates to compositions and methods for treating or preventing vascular sclerosis. In one aspect, the invention relates to prophylactic and therapeutic treatment of vascular sclerosis accompanying or induced by CKD in a subject. In another aspect, the present invention relates to reducing or controlling vascular sclerosis in a subject accompanying or induced by CKD. In some embodiments, the invention provides a method of treating vascular sclerosis in a subject comprising the step of administering to said subject a morphogen selected from BMP-7, BMP-5, BMP-6, OP-2 (BMP-8) and variants thereof. In some embodiments, the invention provides a method of treating vascular sclerosis in a subject comprising the step of contacting vascular smooth muscle cells with BMP-7, BMP-5, BMP-6 or OP-2 (BMP-8). In some a preferred embodiment, the morphogen is BMP-7.

In some embodiments, the invention provides a method of treating vascular sclerosis in a subject comprising the step of administering to said subject an antagonist of a mineralizing BMP. In other embodiments, the invention provides a method of treating vascular sclerosis comprising the step of contacting vascular smooth muscle cells with an antagonist of a mineralizing BMP. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP.

In some embodiments, the invention provides a method of preventing vascular sclerosis in a subject comprising the step of administering to said subject a morphogen selected from the group consisting of BMP-7, BMP-5, BMP-6, OP-2 (BMP-8) and variants thereof. In some embodiments, the invention provides a method of preventing vascular sclerosis in a subject comprising the step of contacting vascular smooth muscle cells with BMP-7, BMP-5, BMP-6 or OP-2 (BMP-8). In a preferred embodiment, the morphogen is BMP-7. In other embodiments, the invention provides a method of preventing vascular sclerosis in a subject comprising the step of contacting vascular smooth muscle cells with an antagonist of a mineralizing BMP. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP.

In some embodiments, the invention provides a method of reducing or controlling vascular sclerosis in a subject comprising the step of administering to said subject a morphogen selected from the group consisting of BMP-7, BMP-5, BMP-6, OP-2 (BMP-8) and variants thereof. In some embodiments, the invention provides a method of reducing or controlling vascular sclerosis in a subject comprising the step of contacting vascular smooth muscle cells with BMP-7, BMP-5, BMP-6 or OP-2 (BMP-8). In a preferred embodiment, the morphogen is BMP-7. In other embodiments, the invention provides a method of treating vascular sclerosis in a subject comprising the step of contacting vascular smooth muscle cells with an antagonist of a mineralizing BMP. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In other embodiments, the vascular sclerosis accompanies or is induced by CKD.

Another aspect of the invention is to treat, prevent or reduce neointimal hyperplasia in a subject. In some embodiments, the invention provides a method of treating neointimal hyperplasia in a subject comprising the step of administering to said subject a morphogen selected from BMP-7, BMP-5, BMP-6, OP-2 (BMP-8) and variants thereof. In some embodiments, the invention provides a method of treating neointimal hyperplasia in a subject comprising the step of contacting vascular smooth muscle cells with a morphogen selected from BMP-7, BMP-5, BMP-6 and OP-2 (BMP-8). In a preferred embodiment, the morphogen is BMP-7. In other embodiments, the invention provides a method of treating neointimal hyperplasia in a subject comprising the step of contacting vascular smooth muscle cells with an antagonist of a mineralizing BMP. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In some embodiments, the neointimal hyperplasia is associated with anastomosis. In some embodiments, the neointimal hyperplasia accompanies or is induced by CKD.

In some embodiments, the invention provides a method of preventing neointimal hyperplasia in a subject comprising the step of administering to said subject a morphogen selected from BMP-7, BMP-5, BMP-6, OP-2 (BMP-8) and variants thereof. In some embodiments, the invention provides a method of preventing neointimal hyperplasia in a subject comprising the step of contacting vascular smooth muscle cells with a morphogen selected from BMP-7, BMP-5, BMP-6 and OP-2 (BMP-8). In a preferred embodiment, the morphogen is BMP-7. In other embodiments, the invention provides a method of preventing neointimal hyperplasia in a subject comprising the step of contacting vascular smooth muscle cells with an antagonist of a mineralizing BMP. In certain embodiments, the mineralizing BMP is BMP-2 or BMP-4, or an analog thereof. In some embodiments, the mineralizing BMP antagonist is noggin. In some embodiments, the neointimal hyperplasia is associated with anastomosis. In some embodiments, the neointimal hyperplasia accompanies or is induced by CKD.

In some embodiments, the invention provides a method of reducing neointimal hyperplasia in a subject comprising the step of administering to said subject a morphogen selected from BMP-7, BMP-5, BMP-6, OP-2 (BMP-8) and variants thereof. In some embodiments, the invention provides a method of reducing neointimal hyperplasia in a subject comprising the step of contacting vascular smooth muscle cells with a morphogen selected from BMP-7, BMP-5, BMP-6 and OP-2 (BMP-8). In a preferred embodiment, the morphogen is BMP-7. In other embodiments, the invention provides a method of reducing neointimal hyperplasia in a subject comprising the step of contacting vascular smooth muscle cells with an antagonist of a mineralizing BMP. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In some embodiments, the neointimal hyperplasia is associated with anastomosis. In some embodiments, the neointimal hyperplasia is induced by chronic kidney disease.

The present invention also relates to compositions and methods for inducing differentiation of vascular smooth muscle cells. In some embodiments, the invention provides a method of inducing vascular smooth muscle cell differentiation comprising the step of contacting a vascular smooth muscle progenitor cell or an undifferentiated or dedifferentiated vascular smooth muscle cell with a morphogen selected from the group consisting of BMP-7, BMP-5, BMP-6 and OP-2 (BMP-8). In a preferred embodiment, the morphogen is BMP-7. In some embodiments, the invention provides a method of inducing vascular smooth muscle cell differentiation comprising the step of contacting a vascular smooth muscle progenitor cell or an undifferentiated or dedifferentiated vascular smooth muscle cell with an antagonist of a mineralizing BMP. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In some embodiments, the dedifferentiation of the vascular smooth muscle cells accompanies or is induced by CKD.

The present invention also relates to prevention and treatment of vascular calcification (VC). In one aspect, the invention relates to prophylactic and therapeutic treatment of vascular calcification accompanying or induced by CKD. In the animal model of CKD-stimulated VC described above, matrix mineralization was observed when media phosphorus was increased in the presence of a BMP-2 and RUNX2 directed osteoblastic transcription. This phosphorus stimulated mineralization in vitro was silenced by inhibition of osterix, a second critical osteoblast transcription factor, and by inhibition of BMP-2 action by a BMP-2 antagonist, noggin.

Thus, one aspect of the present invention relates to reducing, controlling, and preventing matrix mineralization by inhibiting BMP that promote mineralization. Another aspect of the invention is reducing, controlling, and preventing matrix mineralization by inhibiting osterix. In one embodiment, the present invention relates to reducing, controlling, and preventing matrix mineralization by inhibiting BMP-2 action by a BMP-antagonist, noggin. In another embodiment, BMP-2 action is countered by another BMP, for example BMP-7.

In vivo, CKD produced hyperphosphatemia and stimulated aortic osterix expression. Control of hyperphosphatemia, with phosphate binding agents or BMP-7, decreased osterix expression and aortic mineralization.

Thus, another aspect of the present invention relates to reducing, controlling, and preventing vascular mineralization by controlling hyperphosphatemia. One embodiment of the present invention is a method of reducing, controlling and preventing hyperphosphatemia in a subject in need thereof, comprising the step of administering a phosphate binding agent, thereby reducing the serum phosphorus content. In another embodiment, BMP-7 is administered to reduce, control, or prevent hyperphosphatemia. One embodiment of the invention is a method of reducing, controlling and preventing vascular mineralization by controlling hyperphosphatemia. Another embodiment of the invention is a method of reducing osterix expression comprising the step of administering a phosphate binding agent or BMP-7.

Human aortic smooth muscle cell cultures isolated from atherosclerotic aortas demonstrated a BMP-2 and -4 activated osteoblastic gene transcription program (Lecanda, F. et al., *J. Cell Biochem.* 67:386-398, 1997)[23] Phosphorus stimulated mineralization of the extracellular matrix of these cultures analogous to bone formation in vitro. Mineralization was blocked by a BMP antagonist, noggin, in the presence of high phosphorus. Phosphorus added critical stimulation of the osteoblastic mineralization program through increased expression of the osteoblast specific transcription factor, osterix. (Nakashima, K. et al., *Cell* 108:17-29, 2002; Lee, M.-H., et al., *Biochem. Biophys. Res. Comm.* 309:689-694, 2003)[24;25] Inhibition of mineralization was produced by decreasing osterix expression in the presence of high media phosphate. The data in vitro were perfectly matched in vivo by CKD in part by stimulating the high phosphorus signal. High fat fed atherosclerotic LDLR−/− mice expressed BMP-4 and RUNX2 and had some low level aortic mineralization. CKD stimulated hyperphosphatemia, osterix expression and aortic mineralization. Mineralization was partially reversible by treatment of hyperphosphatemia or with BMP-7 (which also corrected hyperphosphatemia), associated with silencing of osterix expression.

The present invention relates to a pharmaceutical composition comprising a morphogen selected from BMP-7, BMP-5, BMP-6 and OP-2 (BMP-8) for treating or preventing vascular sclerosis in a subject. In a preferred embodiment, the pharmaceutical composition for treating or preventing vascular sclerosis comprises BMP-7. The present invention also relates to a pharmaceutical composition comprising an antagonist of a mineralizing BMP for treating or preventing vascular sclerosis in a subject. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In some embodiments, the vascular sclerosis accompanies or is induced by chronic kidney disease.

The present invention relates to a pharmaceutical composition comprising a morphogen selected from BMP-7, BMP-5, BMP-6 and OP-2 (BMP-8) for treating, preventing or reducing neointimal hyperplasia in a subject. In a preferred embodiment, the pharmaceutical composition for treating, preventing or reducing neointimal hyperplasia comprises BMP-7. The present invention also relates to a pharmaceutical composition comprising an antagonist of a mineralizing BMP for treating, preventing or reducing neointimal hyperplasia. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In some embodiments, the neointimal hyperplasia is associated with anastomosis. In some embodiments, the neointimal hyperplasia accompanies or is induced by chronic kidney disease.

The present invention also relates to a pharmaceutical composition comprising a morphogen selected from BMP-7, BMP-5, BMP-6 and OP-2 (BMP-8) for inducing differentiation of a vascular smooth muscle progenitor cell or an undifferentiated or dedifferentiated vascular smooth muscle cell. In a preferred embodiment, the pharmaceutical composition for inducing differentiation of a vascular smooth muscle progenitor cell or an undifferentiated or dedifferentiated vascular smooth muscle cell comprises BMP-7. The present invention also relates to a pharmaceutical composition comprising an antagonist of a mineralizing BMP for inducing differentiation of a vascular smooth muscle progenitor cell or an undifferentiated or dedifferentiated vascular smooth muscle cell. In certain embodiments, the mineralizing BMP is BMP-2 or BMP-4, or an analog thereof. In some embodiments, the mineralizing BMP antagonist is noggin. In other embodiments, the mineralizing BMP antagonist is a mineralization countering BMP. In certain embodiments, the dedifferentiation of the vascular smooth muscle cells accompanies or is induced by CKD.

The present invention relates to a pharmaceutical composition comprising a phosphorus binding agent for the treatment of hyperphosphatemia, and thus, vascular calcification. The present invention further relates to a pharmaceutical composition comprising a BMP inhibitor for the treatment of vascular calcification. The invention also relates to a pharmaceutical composition comprising BMP-7 for the treatment of vascular calcification.

III. Basic Kidney Functions And Their Indicators

BUN and Creatinine. The concentration in the blood (blood level) of blood urea nitrogen (BUN), known as urea, and creatinine (Cr) can be measured by routine laboratory tests. BUN and creatinine levels indicate the general function of the kidneys. BUN is a metabolic by-product of protein-rich food such as meat, poultry, and certain vegetables. BUN is filtered out of the blood by the kidneys and excreted in the urine. Creatinine is continuously generated by normal cell metabolism within the muscles. Creatinine is also filtered out of the blood by the kidneys and excreted in the urine.

The amounts of BUN and creatinine in the blood are equal to the amount excreted by the kidneys. The blood levels of BUN and Cr remain unchanged unless there is sudden deterioration of renal (i.e., kidney) function. If the kidneys are suddenly unable to function, BUN and Cr increase daily. This condition is known as acute renal failure. Chronic renal failure is a condition distinguished by a gradual increase in BUN and Cr over a long period of time.

Measurement of Kidney Function. When renal function decreases, blood levels of Cr and BUN increase because the kidneys are unable to clean the blood effectively. Factors not related to the kidneys also impact BUN and Cr levels. Creatinine, in particular, is affected by age, sex, weight, and muscle mass.

Renal function is measured to evaluate the rate at which both kidneys are able to clean the blood. To measure renal function, a 24-hour urine sample must be collected. It is of importance that the 24-hour sample is complete (i.e., no urine is missing), so that true renal function will not be underestimated.

The amount of Cr in the urine sample is compared to the blood level of Cr. This figure is known as creatinine clearance (CrCl), the rate at which both kidneys clean the blood. The normal CrCl is about 90 to 130 milliliters per minute (mL/min). Many people gradually lose renal function as they age. Alternative renal function measurements rely on tables or formulas that take into consideration age, body weight, sex, and blood creatinine.

Some health care facilities in the United States offer the Glofil-125 assay to evaluate renal function. Sodium iothalamate 1-125 (a radiopharmaceutical) is injected into the skin, and blood and urine samples are obtained to determine renal function. The test is easy to perform, is more sensitive than blood creatinine measurements, and provides results within 2 to 3 hours. Measurements of renal function determine the severity of kidney impairment. It is important to monitor renal function over time to document the rate of deterioration or improvement with treatment.

Glomerular Filtration Rate (GFR). The "glomerular filtration rate" or "GFR" is proportional to the rate of clearance into urine of a plasma-borne substance which is not bound by serum proteins, is freely filtered across glomeruli, and is neither secreted nor reabsorbed by the renal tubules. Thus, as used herein, GFR preferably is defined by the following equation.

$$GFR = U_{conc} \times V/P_{conc}$$

where $U_{conc}$ is the urine concentration of the marker, $P_{conc}$ is the plasma concentration of the marker, and V is the urine flow rate in ml/min. Optionally, GFR is corrected for body surface area. Thus, the GFR values used herein may be regarded as being in units of ml/min/1.73 m².

The preferred measure of GFR is the clearance of inulin but, because of the difficulty of measuring the concentrations of this substance, the clearance of creatinine is typically used in clinical settings. For example, for an average size, healthy human male (70 kg, 20-40 yrs), a typical GFR measured by creatinine clearance is expected to be approximately 125 ml/min with plasma concentrations of creatinine of 0.7-1.5 mg/dL. For a comparable, average size woman, a typical GFR measured by creatinine clearance is expected to be approximately 115 ml/min with creatinine levels of 0.5-1.3 mg/dL. During times of good health, human GFR values are relatively stable until about age 40, when GFR typically begins to decrease with age. For subjects surviving to age 85-90, GFR may be reduced to 50% of the comparable values at 40.

Expected Glomerular Filtration Rate ($GFR_{exp}$). An estimate of the "expected GFR" or "$GFR_{exp}$" may be provided based upon considerations of a subject's age, weight, sex, body surface area, and degree of musculature, and the plasma concentration of some marker compound (e.g., creatinine) as determined by a blood test. Thus, as an example, an expected GFR or $GFR_{exp}$ maybe estimated as:

$$GFR_{exp} = (140 - age) \times weight\ (kg) / [72 \times P_{conc}\ (mg/dl)]$$

This estimate does not take into consideration such factors as surface area, degree of musculature, or percentage body fat. Nonetheless, using plasma creatinine levels as the marker, this formula has been employed for human males as an inexpensive means of estimating GFR. Because creatinine is produced by striated muscle, the expected GFR or $GFR_{exp}$ of human female subjects is estimated by the same equation multiplied by 0.85 to account for expected differences in muscle mass. (See Lemann, et al. (1990) Am. J. Kidney Dis. 16(3): 236).

Broad Cast. Microscopic examination of urinary sediment for the presence of formed elements is a standard procedure in urinalysis. Amongst the formed elements which may be present in urine are cylindrical masses of agglutinated materials that typically represent a mold or "cast" of the lumen of a distal convoluted tubule or collecting tubule. In healthy human subjects, such casts typically have a diameter of 15-25 μm. In subjects with chronic renal failure, however, hypertrophy of the tubules may result in the presence of "broad casts" or "renal failure casts" which are 2-6 times the diameter of normal casts and often have a homogeneous waxy appearance. Thus, as used herein, a "broad cast" means a urinary sediment cast having a diameter of 2-6 times normal, or about 30-150 μm for human casts.

IV. Vascular Sclerosis And Calcification

Vascular calcification (VC) in the LDLR−/− mouse fed high fat diets has been shown to be a clinically relevant model of VC in type 2 diabetes, metabolic syndromes, obesity, and atheroma (Towler, D. A. et al., *J. Biol. Chem.* 273:30427-30434, 1998; Shao, J. S. et al. *J. Clin. Invest.* 115:1210-1220, 2005)[26;27] and it is a model of stimulation of vascular calcification by CKD (Davies 2003).[19] Previous studies have demonstrated that BMP-7 prevented the development of aortic calcification in LDLR−/− mice with CKD fed high fat diets in part through stimulation of bone formation leading to control of hyperphosphatemia by increased skeletal deposition (Davies 2003; Davies 2005).[19;20] In order to examine the actions of BMP-7 and hyperphosphatemia control on treating established VC, the inventors of the instant invention undertook a "treatment study" experimental design, wherein therapy was begun at the time previous prevention studies ended and continued it for a period of six weeks.

A. Therapeutic Agents

The morphogens of the present invention are naturally occurring proteins, or functional variants and analogs of naturally occurring proteins, in the osteogenic protein/bone morphogenetic protein (OP/BMP) family within the TGF-β superfamily of proteins.

(i) OP/BMP Family of Morphogens

The "OP/BMP family" of proteins forms a distinct subgroup within the loose evolutionary grouping of sequence-related proteins known as the TGF-β superfamily. Members of this protein family comprise secreted polypeptides that share common structural features, and that are similarly processed from a pro-protein to yield a carboxy-terminal mature protein. This family of proteins is also referred to as morphogens. As noted above, a protein is morphogenic as defined herein if it induces the developmental cascade of cellular and molecular events that culminate in the formation of new, organ-specific tissue.

For this invention, the "OP/BMP family" can further be classified into at least two groups, one of which is a "mineralizing BMP" family and another is a "mineralization-countering BMP" family, as described above in the Definition section.

In a preferred embodiment of the present invention, a morphogen useful for the practice of the invention is a dimeric protein, each polypeptide component of which has a sequence that corresponds to, or is functionally equivalent to, at least the conserved C-terminal six or seven cysteine skeleton of human BMP proteins. For the mineralization-countering BMP, a preferred embodiment uses BMP-7 (OP-1), included in SEQ ID NO: 2, and/or its analog, which shares 70% amino acid sequence homology or 50% identity with BMP-7 (OP-1) in this region. For identifying mineralizing BMP, a preferred embodiment is BMP-2 or BMP-4, or an analog thereof. The morphogens are generally competent to induce a cascade of events including the following, in a morphogenically permissive environment: stimulating proliferation of progenitor cells; stimulating the differentiation of progenitor cells; stimulating the proliferation of differentiated cells; and supporting the growth and maintenance of differentiated cells. Under appropriate conditions, morphogens are also competent to induce redifferentiation of cells that have undergone abnormal differentiation. Details of how the morphogens useful in this invention were identified, as well as a description on how to make, use and test them for morphogenic activity are disclosed in numerous publications, including U.S. Pat. Nos. 5,011,691 and 5,266,683, and the international patent application publications WO 92/15323; WO 93/04692; and WO 94/03200, each of which are incorporated by reference herein. As disclosed therein, the morphogens can be purified from naturally sourced material or recombinantly produced from prokaryotic or eukaryotic host cells, using the genetic sequences disclosed therein. Alternatively, novel morphogenic sequences can be identified following the procedures disclosed therein.

The naturally occurring morphogens share substantial amino acid sequence homology in their C-terminal sequences (a region dubbed as "six- or "seven-cysteine skeleton" sequence for the conserved cysteines in this region). Typically, a naturally occurring morphogen is translated as a precursor, having an N-terminal signal peptide sequence, typically less than about 35 residues in length, followed by a "pro" domain that is cleaved to yield the mature polypeptide, which includes the biologically active C-terminal skeleton sequence. The signal peptide is cleaved rapidly upon translation, at a cleavage site that can be predicted in a given sequence using the method of Von Heijne, *Nucleic Acids Research* 14: 4683-4691 (1986). The "pro" domain is variable both in sequence and in length, ranging from approximately 200 to over 400 residues. The pro domain is cleaved to yield the "mature" C-terminal domain of approximately 115-180 residues, which includes the conserved six- or seven-cysteine C-terminal domain of 97-106 residues. The pro polypeptide typically is about three times larger than the fully processed, mature C-terminal polypeptide. Under native conditions, the protein is secreted as a mature dimer and the cleaved pro polypeptide is thought to remain associated therewith to form a protein complex, presumably to improve the solubility of the mature dimeric protein. The complexed form of a morphogen is generally observed to be more soluble than the mature form under physiological conditions.

As used herein, the "pro form" of an OP/BMP family member refers to a protein comprising a folded pair of polypeptides, each comprising a pro domain in either covalent or noncovalent association with the mature domains of the OP/BMP polypeptide. The pro form appears to be the primary form secreted from cultured mammalian cells. The "mature form" of the protein refers to mature C-terminal domain which is not associated, either covalently or noncovalently, with the pro domain. Any preparation of BMP-7 (OP-1) is considered to contain mature form when the amount of pro domain in the preparation is no more than 5% of the amount of "mature" C-terminal domain.

Natural-sourced morphogenic protein in its mature, native form, is typically a glycosylated dimer, having an apparent molecular weight of about 30-36 kDa as determined by SDS-PAGE. When reduced, the 30 kDa protein gives rise to two glycosylated polypeptide subunits having apparent molecular weights in the range of about 16 kDa and about 18 kDa. The unglycosylated dimeric protein, which also has morphogenic activity, typically has an apparent molecular weight in the range of about 27 kDa. When reduced, the 27 kDa protein gives rise to two unglycosylated polypeptides having molecular weights typically in the range of about 14 kDa to about 16 kDa.

OP/BMP family members useful herein include any of the known naturally occurring native proteins including allelic, phylogenetic counterpart and other variants thereof, whether naturally sourced or biosynthetically produced (e.g., including "muteins" or "mutant proteins"), as well as new, active members of the OP/BMP family of proteins. Particularly useful sequences include those comprising the C-terminal seven cysteine domains of mammalian, with all cysteines preserved, preferably human, BMP-7 (OP-1), BMP5, BMP6, and GDF-5. Other proteins useful in the practice of the invention include active forms of Vg1, Vgr-1, 60A, GDF-1, GDF-3, GDF-5,GDF-6, GDF-7, BMP10, BMP11; BMP13, BMP15, UNIVIN, NODAL, SCREW, ADMP or NEURAL from various organisms, and analogs thereof. Any one of these proteins and polypeptides having biological activities of BMP-7 may be used as mineralization-countering BMP.

In one preferred embodiment, the morphogen of the invention is BMP-7 (OP-1). In a particularly preferred embodiment, BMP-7 is in a soluble form. In preferred embodiments, each of the polypeptide subunits of a dimeric morphogenic protein as defined herein comprises an amino acid sequence sharing a defined relationship with an amino acid sequence of a reference morphogen. In one embodiment, preferred morphogenic polypeptide chains share a defined relationship with a sequence present in morphogenically active full-length human BMP-7 (OP-1), SEQ ID NO: 3. However, any one or more of the naturally occurring or biosynthetic morphogenic proteins disclosed herein similarly could be used as a reference sequence. Preferred morphogenic polypeptide chains share a defined relationship with at least the C-terminal six cysteine skeleton of human BMP-7 (OP-1), residues 335-431 of SEQ ID NO: 3 (or residues 43-139 of SEQ ID NO: 1). Preferably, morphogenic proteins share a defined relationship with at least the C-terminal seven cysteine skeleton of human BMP-7 (OP-1), residues 330-431 of SEQ ID NO: 3 (or residues 38-139 of SEQ ID NO: 1).

Functionally equivalent sequences include functionally equivalent arrangements of cysteine residues disposed within the reference sequence, including amino acid insertions or deletions which alter the linear arrangement of these cysteines, but do not materially impair their relationship in the folded structure of the dimeric morphogen protein, including their ability to form such intra- or inter-chain disulfide bonds as may be necessary for morphogenic activity. Functionally equivalent sequences further include those wherein one or more amino acid residues differ from the corresponding residue of a reference sequence, e.g., the C-terminal seven cysteine skeleton of human BMP-7 (OP-1), provided that this difference does not destroy tissue morphogenic activity. Accordingly, conservative substitutions of corresponding amino acids in the reference sequence are preferred.

Table I below summarizes various naturally occurring members of the OP/BMP family identified to date, including their nomenclature as used herein, their Sequence listing references, and publication sources for the amino acid sequences for the full length proteins not included in the Sequence listing. Each of the generic terms set forth in Table I is intended and should be understood to embrace the therapeutic effective proteins expressed from nucleic acids encoding the identified sequence mentioned below and set forth in the Sequence listing, or an active fragment or precursor thereof, or a functional equivalent thereof such as a naturally occurring or biosynthetic variant. Naturally occurring variants include allelic variant forms isolated from other individuals of a single biological species, as well as species variants (homologous) isolated from phylogenetically distinct biological species. These morphogens may be mineralizing BMPs or mineralization-countering BMPs.

TABLE I

Exemplary Morphogens

| | |
|---|---|
| "BMP-7" or "OP-1" | refers generically to the group of morphogenically active proteins expressed from part or all of a DNA sequence encoding OP-I protein, including allelic and species variants thereof, e.g., human BMP-7 (OP-1) ("hBMP-7 (OP-1)", SEQ ID NOs: 1, mature protein amino acid sequence), or mouse BMP-7 (OP-1) ("mBMP-7 (OP-1)", SEQ ID NO: 4, mature protein amino acid sequence.) The conserved seven cysteine skeleton is defined by residues 38 to 139 of SEQ ID NOs: 1 and 4. The cDNA sequences and the amino acids encoding the full length proteins are provided in SEQ ID NOs: 17 and 3 (hBMP-7 (OP-1)) and SEQ ID NOs: 18 and 19 (mBMP-7 (OP-1)). The mature proteins are defined by residues 293-431 (hBMP-7 (OP-1)) and 292-430 (mBMP-7 (OP-1)). The "pro" regions of the proteins, cleaved to yield the mature, morphogenically active proteins are defined essentially by residues 30-292 (hBMP-7 (OP-1)) and residues 30-291 (mBMP-7 (OP-1)). |
| "OP-2 (BMP-8)" | refers generically to the group of active proteins expressed from part or all of a DNA sequence encoding OP-2 (also known as BMP-8) protein, including allelic and species variants thereof, e.g., human OP-2 (BMP-8) ("hOP-2", SEQ ID No: 5, mature protein amino acid sequence) or mouse OP-2 ("mOP-2", SEQ ID No: 6, mature protein amino acid sequence). The conserved seven cysteine skeleton is defined by residues 38 to 139 of SEQ ID NOs: 5 and 6. The cDNA sequences and the amino acids encoding the full length proteins are provided in SEQ ID NOs: 20 and 21 (hOP-2) and SEQ ID NOs: 22 and 23 (mOP-2). The mature proteins are defined essentially by residues 264-402 (hOP-2) and 261-399 (mOP-2). The "pro" regions of the proteins, cleaved to yield the mature, morphogenically active proteins likely are defined essentially by residues 18-263 (hOP-2) and residues 18-260 (mOP-2). Another cleavage site also occurs 21 residues upstream for both OP-2 proteins. |
| "CBMP2" | refers generically to the morphogenically active proteins expressed from a DNA sequence encoding the CBMP2 proteins, including allelic and species variants thereof, e.g., human CBMP2A ("CBMP2A(fx)"), SEQ ID NO: 10) or human CBMP2B DNA ("CBMP2B(fx)"), SEQ ID NO: 11). The amino acid sequence for the full length proteins, referred to in the literature as BMP2A and BMP2B, or BMP2 and BMP4, appear in Wozney, et al. (1988) Science 242: 1528-1534, the content of which is incorporated by reference herein. The pro-domain for BMP2 (BMP2A) likely includes residues 25-248 or 25-282; the mature protein, residues 249-396 or 283-396. The pro-domain for BMP4 (BMP2B) likely includes residues 25-256 or 25-292; the mature protein, residues 257-408 or 293-408. |
| "DPP(fx)" | refers to protein sequences encoded by the *Drosophila* DPP gene (DPP protein, see SEQ ID NO: 7) and defining the conserved seven cysteine skeleton. The amino acid sequence for the full length protein appears in Padgett, et al (1987) Nature 325: 81-84, the content of which is incorporated by reference herein. The pro-domain likely extends from the signal peptide cleavage site to residue 456; mature protein likely is defined by residues 457-588. The sequence of DPP(fx) is shown in Table II. |
| "Vgl(fx)" | refers to protein sequences encoded by the *Xenopus* Vgl gene (Vgl protein, see SEQ ID NO: 8) and defining the conserved seven cysteine skeleton. The amino acid sequence for the full length protein appears in Weeks (1987) Cell 51: 861-867, the content of which is incorporated by reference herein. The pro-domain likely extends from the signal peptide cleavage site to residue 246; the mature protein likely is defined by residues 247-360. The sequence of Vgl(fx) is shown in Table II. |
| "Vgr-1(fx)" | refers to protein sequences encoded by the murine vgr-1 gene (Vgr-1 protein, see SEQ ID NO: 9) and defining the conserved seven cysteine skeleton. The amino acid sequence for the full length protein appears in Lyons, et al., (1989) PNAS 86: 4554-4558, the content of which is incorporated by reference herein. The pro-domain likely extends from the signal peptide cleavage site to residue 299; the mature protein likely is defined by residues 300-438. The sequence of Vgr-1(fx) is shown in Table II. |

TABLE I-continued

Exemplary Morphogens

"GDF-1(fx)" — refers to protein sequences encoded by the human GDF-1 gene (GDF-1 protein, see SEQ ID NO: 13) and defining the conserved seven cysteine skeleton. The amino acid sequence for the full length protein is provided in SEQ ID NO: 13. The pro-domain likely extends from the signal peptide cleavage site to residue 214; the mature protein likely is defined by residues 215-372. The sequence of GDF-1(fx) is shown in Table II.

"60A" — refers generically to the morphogenically active proteins expressed from part or all of a DNA sequence (from the *Drosophila* 60A gene) encoding the 60A proteins (see SEQ ID NO: 14). "60A(fx)" refers to the protein sequences defining the conserved seven cysteine skeleton (residues 354 to 455 of SEQ ID NO: 14). The pro-domain likely extends from the signal peptide cleavage site to residue 324; the mature protein likely is defined by residues 325-455. The sequence of 60A(fx) is shown in Table II.

"BMP3(fx)" — refers to protein sequences encoded by the human BMP3 gene (BMP3 protein, see SEQ ID NO: 12) and defining the conserved seven cysteine skeleton. The amino acid sequence for the full length protein appears in Wozney et al. (1988) Science 242: 1528-1534, the content of which is incorporated by reference herein. The pro-domain likely extends from the signal peptide cleavage site to residue 290; the mature protein likely. is defined by residues 291-472. The sequence of BMP3(fx) is shown in Table II.

"BMP5(fx)" — refers to protein sequences encoded by the human BMP5 gene (BMP5 protein, see SEQ ID NO: 15) and defining the conserved seven cysteine skeleton. The amino acid sequence for the full length protein appears in Celeste, et al. (1991) PNAS 87: 9843-9847, the content of which is incorporated by reference herein. The pro-domain likely extends from the signal peptide cleavage site to residue 316; the mature protein likely is defined by residues 317-454. The sequence of BMP5(fx) is shown in Table II.

"BMP6(fx)" — refers to protein sequences encoded by the human BMP6 gene (BMP6 protein, see SEQ ID NO: 16) and defining the conserved seven cysteine skeleton. The amino acid sequence for the full length protein appears in Celeste, et al. (1990) PNAS 87: 9843-9847, the content of which is incorporated by reference herein. The pro-domain likely includes extends from the signal peptide cleavage site to residue 374; the mature sequence likely includes residues 375-513. The sequence of BMP6(fx) is shown in Table II.

The OP-2 (BMP-8) proteins have an "additional" cysteine residue in this region (e.g., see residue 41 of SEQ ID NOs: 21 and 23), in addition to the conserved cysteine skeleton in common with the other proteins in this family. The GDF-1 protein has a four amino acid insert within the conserved skeleton (compare SEQ ID NO: 19 with SEQ ID NO: 13) but this insert likely does not interfere with the relationship of the cysteines in the folded structure. In addition, the CBMP2 proteins are missing one amino acid residue within the cysteine skeleton.

The morphogens are inactive when reduced, but are active as oxidized homodimers and when oxidized in combination with other morphogens of this invention (e.g., as heterodimers). Thus, as defined herein, a morphogen is a dimeric protein comprising a pair of polypeptide chains, wherein each polypeptide chain comprises at least the C-terminal six cysteine skeleton defined by residues 43-139 of SEQ ID NO: 1, including functionally equivalent arrangements of these cysteines (e.g., amino acid insertions or deletions which alter the linear arrangement of the cysteines in the sequence but not their relationship in the folded structure), such that, when the polypeptide chains are folded, the dimeric protein species comprising the pair of polypeptide chains has the appropriate three-dimensional structure, including the appropriate intra- or inter-chain disulfide bonds such that the protein is capable of acting as a morphogen as defined herein. Specifically, the morphogens generally are capable of all of the following biological functions in a morphogenically permissive environment: stimulating proliferation of progenitor cells; stimulating the differentiation of progenitor cells; stimulating the proliferation of differentiated cells; and supporting the growth and maintenance of differentiated cells, including the "redifferentiation" of transformed cells. In addition, it is also anticipated that these morphogens are capable of inducing redifferentiation of committed cells under appropriate environmental conditions.

The following publications disclose published morphogen polypeptide sequences, as well as relevant chemical and physical properties, of naturally occurring and/or synthetic morphogens: BMP-7 (OP-1) and OP-2 (BMP-8): U.S. Pat. Nos. 5,011,691, 5,266,683, Ozkaynak, et al., *EMBO J.* 9: 2085-2093 (1990); OP-3: WO 94/10203 (PCT US93/10520); BMP-2, BMP-3, and BMP-4: WO 88/00205, Wozney, et al., *Science* 242: 1528-1534 (1988); BMP-5 and BMP-6: Celeste, et al., *PNAS* 87: 9843-9847 (1991); Vgr1: Lyons, et al., *PNAS* 86: 4554-4558 (1989); DPP: Padgett, et al., *Nature* 325: 81-84 (1987); Vg-1: Weeks *Cell* 51: 861-867 (1987); BMP-9: WO 95/33830 (PCT/US95/07084); BMP-10: WO 94/26893 (PCT/US94/05290); BMP-11: WO 94/26892 (PCT/US94/05288); BMP-12: WO 95/16035 (PCT/US94/14030); BMP-13: WO 95/16035 (PCT/US94/14030); GDF-1: WO 92/00382 (PCT/US91/04096) and Lee, et al., *PNAS* 88:4250-

4254 (1991); GDF-8: WO 94/21681 (PCT/US94/03019); GDF-9: WO 94/15966 (PCT/US94/00685); GDF-10: WO 95/10539 (PCT/US94/11440); GDF-11: WO 96/01845 (PCT/US95/08543); BMP-15: WO 96/36710 (PCT/US96/06540); MP121: WO 96/01316 (PCT/EP95/02552); GDF-5 (CDMP-1, MP52): WO 94/15949 (PCT/US94/00657) and WO 96/14335 (PCT/US94/12814) and WO 93/16099 (PCT/EP93/00350); GDF-6 (CDMP-2, BMP-13): WO 95/01801 (PCT/US94/07762) and WO 96/14335 and WO 95/10635 (PCT/US94/14030); GDF-7 (CDMP-3, BMP-12): WO 95/10802 (PCT/US94/07799) and WO 95/10635 (PCT/US94/14030). In another embodiment, useful proteins include biologically active biosynthetic constructs, including novel biosynthetic morphogenic proteins and chimeric proteins designed using sequences from two or more known morphogens. See also the biosynthetic constructs disclosed in U.S. Pat. No. 5,011,691 (e.g., CBMP-7 (OP-1), COP-3, COP-4, COP-5, COP-7, and CBMP-7 (OP-1)6).The disclosure of all cited references describing morphogens and other related proteins are incorporated herein by reference.

In certain preferred embodiments, useful morphogenic proteins include those in which the amino acid sequences comprise a sequence sharing at least 70% amino acid sequence homology (identity or conserved substitution), and preferably 80%, 85%, 90%, 95% or 99% homology, with a reference morphogenic protein selected from the exemplary naturally occurring morphogenic proteins listed herein. Preferably, the reference protein for mineralization-countering BMP is human BMP-7 (OP-1), and the reference sequence thereof is the C-terminal seven cysteine skeleton present in osteogenically active forms of human BMP-7 (OP-1), residues 330-431 of SEQ ID NO: 3 (or residues 38-139 of SEQ ID NO: 1). Useful morphogenic proteins accordingly include allelic, phylogenetic counterpart and other variants of the preferred reference sequence, whether naturally occurring or biosynthetically produced (e.g., including "muteins" or "mutant proteins"), as well as novel members of the general morphogenic family of proteins including those set forth and identified above. Certain particularly preferred morphogenic polypeptides share at least 50% amino acid identity with the preferred reference sequence of human BMP-7 (OP-1), or any of the other morphogens described above, still more preferably at least 55%, 60%, 65%, 70%, 80%, 85%, 90%, 95%, 99% or more amino acid identity therewith.

FIG. 10 recites the percent amino acid sequence homology and percent identity within the C-terminal seven cysteine skeletons of various representative members of the TGF-β superfamily, using BMP-7 (OP-1) as the reference sequence. The percent homologies recited in the figure are determined by aligning the sequences using the MegaAlign Program (DNAstar, Inc.). Insertions and deletions from the reference morphogen sequence (the C-terminal, biologically active seven-cysteine skeleton of hBMP-7 (OP-1)) are ignored for purposes of calculation (details see below).

In other preferred embodiments, the family of morphogenic polypeptides useful in the present invention, and members thereof, are defined by a generic amino acid sequence.

Particularly useful sequences for use as morphogens in this invention for counteracting mineralization include the C-terminal domains, e.g., the C-terminal 96-102 amino acid residues of Vgl, Vgr-1, BMP-7 (OP-1), OP-2 (BMP-8), GDF-1, GDF-5 (see Table II, below, and SEQ ID NOs: 1-13), as well as proteins comprising the C-terminal domains of 60A, BMP5 and BMP6 (see SEQ ID NOs: 12, 14-16), all of which include at least the conserved six or seven cysteine skeleton. In addition, biosynthetic constructs designed from the generic sequences, such as CBMP-7 (OP-1), 3-5, 7, 16, disclosed in U.S. Pat. No. 5,011,691, also are useful. Other sequences include the inhibins/activin proteins (see, for example, U.S. Pat. Nos. 4,968,590 and 5,011,691). Accordingly, other useful sequences are those sharing at least 70% amino acid sequence homology or 50% identity, and preferably 80% homology or 70% identity with any of the sequences above. These are anticipated to include allelic and species variants and mutants, and biosynthetic muteins, as well as novel members of this morphogenic family of proteins. Particularly envisioned in the family of related proteins are those proteins exhibiting morphogenic activity and wherein the amino acid changes from the preferred sequences include conservative changes. Information regarding conserved amino acid changes are well-known in the art. For example, Dayhoff et al. described in *Atlas of Protein Sequence and Structure*; vol. 5, Suppl. 3, pp. 345-362, (M. O. Dayhoff, ed., Nat'l BioMed. Research Fdn., Washington, D.C. 1978) that certain amino acids substitutions among evolutionary conserved proteins occur at higher than expected frequency than random chance would allow. Thus, conserved amino acid substitutions can be determined according to FIG. 84 (supra). As used herein, potentially useful sequences are aligned with a known morphogen sequence using the method of Needleman et al. ((1970) *J. Mol. Biol.* 48:443-453) and identities calculated by the MegaAlign program (DNAstar, Inc.).

Table II, set forth below, compares the amino acid sequences of the active regions of native proteins that have been identified as morphogens, including human BMP-7 (OP-1) (hBMP-7 (OP-1), SEQ ID NOs: 1-3), mouse BMP-7 (OP-1) (mBMP-7 (OP-1), SEQ ID NOs: 4 and 19), human and mouse OP-2 (BMP-8) (SEQ ID NOs: 5, 6, 21, and 23), CBMP2A (SEQ ID NO: 10), CBMP2B (SEQ ID NO: 11), BMP3 (SEQ ID NO: 12), DPP (from *Drosophila*, SEQ ID NO: 7), Vgl (from *Xenopus*, SEQ ID NO: 8), Vgr-1 (from mouse, SEQ ID NO: 9), GDF-1 (from mouse, SEQ ID NOs: 13), 60A protein (from *Drosophila*, SEQ ID NOs: 14), BMP5 (SEQ ID NO: 15) and BMP6 (SEQ ID NO: 16). The sequences are aligned essentially following the method of Needleman et al. (1970) *J. Mol. Biol.*, 48: 443-453, calculated using the Align Program (DNAstar, Inc.) In the table, three dots indicates that the amino acid in that position is the same as the amino acid in hBMP-7 (OP-1). Three dashes indicates that no amino acid is present in that position, and are included for purposes of illustrating homologies. For example, amino acid residue 60 of CBMP-2A and CBMP-2B is "missing".

TABLE II

| SEQ ID NO | | | | |
|---|---|---|---|---|
| 54 | hBMP-7 (OP-1) | Cys Lys Lys | His Glu Leu Tyr Val |
| 55 | mBMP-7 (OP-1) | . . . . . . . . . | . . . . . . . . . . . . . . . |
| 56 | BMP5 | . . . . . . . . . | . . . . . . . . . . . . . . . |
| 57 | BMP6 | . . . Arg . . . | . . . . . . . . . . . . . . . |
| 58 | Vgr-1 | . . . . . . . . . | . . . Gly . . . . . . . . . |
| 59 | hOP-2 | . . . Arg Arg | . . . . . . . . . . . . . . . |
| 60 | mOP-2 | . . . Arg Arg | . . . . . . . . . . . . . . . |
| 61 | DPP | . . . Arg Arg | . . . Ser . . . . . . . . . |
| 62 | CBMP-2A | . . . . . . Arg | . . . Pro . . . . . . . . . |
| 63 | CBMP-2B | . . . Arg Arg | . . . Ser . . . . . . . . . |
| 64 | BMP3 | . . . Ala Arg | Arg Tyr . . . Lys . . . |
| 65 | Vgl | . . . . . . Lys | Arg His . . . . . . . . . |
| 66 | GDF-1 | . . . Arg Ala | Arg Arg . . . . . . . . . |
| 67 | 60A | . . . Gln Met | Glu Thr . . . . . . . . . |
| | | 1 | 5 |
| 54 | hBMP-7 (OP-1) | Ser Phe Arg | Asp Leu Gly Trp Gln Asp |
| 55 | mBMP-7 (OP-1) | . . . . . . . . . | . . . . . . . . . . . . . . . |
| 56 | BMP5 | . . . . . . . . . | . . . . . . . . . . . . . . . |
| 57 | BMP6 | . . . . . . Gln | . . . . . . . . . . . . . . . . . . |
| 58 | Vgr-1 | . . . . . . Gln | . . . Val . . . . . . . . . . . . |
| 59 | hOP-2 | . . . . . . Gln | . . . . . . . . . . . . Leu . . . |

TABLE II-continued

| SEQ ID NO | | | | | | |
|---|---|---|---|---|---|---|
| 60 | mOP-2 | ......... | ......... | ...Leu | ... | |
| 61 | DPP | Asp...Ser | ...Val... | ...Asp | ... | |
| 62 | CBMP-2A | Asp...Ser | ...Val... | ...Asn | ... | |
| 63 | CBMP-2B | Asp...Ser | ...Val... | ...Asn | ... | |
| 64 | BMP3 | Asp...Ala | ...Ile... | ...Ser | Glu | |
| 65 | Vgl | Glu...Lys | ...Val... | ... | Asn | |
| 66 | GDF-1 | ......... | GluVal... | ...His | Arg | |
| 67 | 60A | Asp...Lys | ......... | ...His | ... | |
| | | 10 | | 15 | | |
| 54 | hBMP-7 (OP-1) | Trp Ile Ile | Ala Pro Glu | Gly Tyr | Ala | |
| 55 | mBMP-7 (OP-1) | ......... | ......... | ... | ... | |
| 56 | BMP5 | ......... | ......... | ... | ... | |
| 57 | BMP6 | ......... | ...Lys... | ... | ... | |
| 58 | Vgr-1 | ......... | ...Lys... | ... | ... | |
| 59 | hOP-2 | ...Val... | ...Gln... | ... | Ser | |
| 60 | mOP-2 | ...Val... | ...Gln... | ... | Ser | |
| 61 | DPP | ......Val | ...Leu... | ... | Asp | |
| 62 | CBMP-2A | ......Val | ...Pro... | ... | His | |
| 63 | CBMP-2B | ......Val | ...Pro... | ... | Gln | |
| 64 | BMP3 | ......... | Ser...Lys | Ser Phe | Asp | |
| 65 | Vgl | ...Val... | ...Gln... | ... | Met | |
| 66 | GDF-1 | ...Val... | ...Arg... | ...Phe | Leu | |
| 67 | 60A | ......... | ......... | ... | Gly | |
| | | 20 | | 25 | | |
| 54 | hBMP-7 (OP-1) | Ala Tyr Tyr | Cys Glu Gly | Glu Cys | Ala | |
| 55 | mBMP-7 (OP-1) | ......... | ......... | ... | ... | |
| 56 | BMP5 | ...Phe... | ...Asp... | ... | Ser | |
| 57 | BMP6 | ...Asn... | ...Asp... | ... | Ser | |
| 58 | Vgr-1 | ...Asn... | ...Asp... | ... | Ser | |
| 59 | hOP-2 | ......... | ......... | ... | Ser | |
| 60 | mOP-2 | ......... | ......... | ... | ... | |
| 61 | DPP | ......... | ...His...Lys... | Pro | | |
| 62 | CBMP-2A | ...Phe... | ...His...Glu... | Pro | | |
| 63 | CBMP-2B | ...Phe... | ...His...Asp... | Pro | | |
| 64 | BMP3 | ......... | ...Ser...Ala... | Gln | | |
| 65 | Vgl | ...Asn... | ...Tyr... | ... | Pro | |
| 66 | GDF-1 | ...Asn... | ...Gln...Gln... | ... | | |
| 67 | 60A | ...Phe... | ...Ser... | ... | Asn | |
| | | 30 | | 35 | | |
| 54 | hBMP-7 (OP-1) | Phe Pro Leu | Asn Ser Tyr | Met Asn | Ala | |
| 55 | mBMP-7 (OP-1) | ......... | ......... | ... | ... | |
| 56 | BMP5 | ......... | ...Ala His Met | ... | ... | |
| 57 | BMP6 | ......... | ...Ala His Met | ... | ... | |
| 58 | Vgr-1 | ......... | ...Ala His... | ... | ... | |
| 59 | hOP-2 | ......... | Asp...Cys... | ... | ... | |
| 60 | mOP-2 | ......... | Asp...Cys... | ... | ... | |
| 61 | DPP | ......... | Ala Asp His Phe | ... | Ser | |
| 62 | CBMP-2A | ......... | Ala Asp His Leu | ... | Ser | |
| 63 | CBMP-2B | ......... | Ala Asp His Leu | ... | Ser | |
| 64 | BMP3 | Leu...Val | Ala Leu Ser Gly Ser† | ... | | |
| 65 | Vgl | Tyr...... | Thr Glu Ile Leu | ... | Gly | |
| 66 | GDF-1 | ......Met | Pro Lys Ser Leu Lys | Pro | | |
| 67 | 60A | ......... | ...Ala His... | ... | | |
| | | 40 | | | | |
| 54 | hBMP-7 (OP-1) | Thr Asn His | Ala Ile Val Gln Thr | Leu | | |
| 55 | mBMP-7 (OP-1) | ......... | ......... | ... | | |
| 56 | BMP5 | ......... | ......... | ... | | |
| 57 | BMP6 | ......... | ......... | ... | | |
| 58 | Vgr-1 | ......... | ......... | ... | | |
| 59 | hOP-2 | ......... | ......Leu...Ser | ... | | |
| 60 | mOP-2 | ......... | ......Leu...Ser | ... | | |
| 61 | DPP | ......... | ......Val... | ... | | |
| 62 | CBMP-2A | ......... | ......... | ... | | |
| 63 | CBMP-2B | ......... | ......... | ... | | |
| 64 | BMP3 | Ser...... | ...Thr Ile...Ser | Ile | | |
| 65 | Vgl | Ser...... | ......Leu... | ... | | |
| 66 | GDF-1 | Leu...... | ...Val Leu Arg Ala | ... | | |
| | | 45 | | 50 | | |
| 54 | hBMP-7 (OP-1) | Val His Phe | Ile Asn Pro Glu Thr | Val | | |
| 55 | mBMP-7 (OP-1) | ......... | ......Asp... | ... | | |
| 56 | BMP5 | ......Leu | Met Phe...Asp His | ... | | |
| 57 | BMP6 | ......Leu | Met...... | ...Tyr | ... | |
| 58 | Vgr-1 | ......Val | Met...... | ...Tyr | ... | |
| 59 | hOP-2 | ...His Leu | Met Lys...Asn Ala | ... | | |
| 60 | mOP-2 | ...His Leu | Met Lys...Asp Val | ... | | |
| 61 | DPP | ...Asn Asn | Asn......Gly Lys | ... | | |
| 62 | CBMP-2A | ...Asn Ser | Val...Ser --- Lys | Ile | | |
| 63 | CBMP-2B | ...Asn Ser | Val...Ser --- Ser | Ile | | |
| 64 | BMP3 | ...Arg Ala† | Gly Val Val Pro Gly | Ile | | |
| 65 | Vgl | ......Ser | ...Glu......Asp | Ile | | |
| 66 | GDF-1 | Met...Ala | Ala Ala...Gly Ala | Ala | | |
| 67 | 60A | ......Leu | Leu Glu...Lys Lys | ... | | |
| | | 55 | | 60 | | |
| 54 | hBMP-7 (OP-1) | Pro Lys Pro | Cys Cys Ala Pro Thr | Gln | | |
| 55 | mBMP-7 (OP-1) | ......... | ......... | ... | | |
| 56 | BMP5 | ......... | ......... | Lys | | |
| 57 | BMP6 | ......... | ......... | Lys | | |
| 58 | Bgr-1 | ......... | ......... | Lys | | |
| 59 | hOP-2 | ......... | ...Ala... | Lys | | |
| 60 | mOP-2 | ......... | ...Ala... | Lys | | |
| 61 | DPP | ......... | ...Ala...Val... | ... | | |
| 62 | CBMP-2A | ......... | ...Ala...Val... | Glu | | |
| 63 | CBMP-2B | ......... | ...Ala...Val... | Glu | | |
| 64 | BMP3 | ...Glu... | ......Val...Glu | Lys | | |
| 65 | Vgl | ...Leu... | ......Val... | Lys | | |
| 66 | GDF-1 | Asp Leu... | ......Val...Ala | Arg | | |
| 67 | 60A | ......... | ......... | Arg | | |
| | | 65 | | 70 | | |
| 54 | hBMP-7 (OP-1) | Leu Asn Ala | Ile Ser Val Leu Tyr | Phe | | |
| 55 | mBMP-7 (OP-1) | ......... | ......... | ... | | |
| 56 | BMP5 | ......... | ......... | ... | | |
| 57 | BMP6 | ......... | ......... | ... | | |
| 58 | Vgr-1 | Val...... | ......... | ... | | |
| 59 | hOP-2 | ...Ser... | Thr...... | ...Tyr | | |
| 60 | mOP-2 | ...Ser... | Thr...... | ...Tyr | | |
| 61 | DPP | ...Asn Ser | Val Ala Met... | ...Leu | | |
| 62 | CBMP-2A | ...Ser... | ...Met... | ...Leu | | |
| 63 | CBMP-2B | ...Ser... | ...Met... | ...Leu | | |
| 64 | BMP3 | Met Ser Ser | Leu...Ile...Phe | Tyr | | |
| 65 | Vgl | Met Ser Pro | ......Met...Phe | Tyr | | |
| 66 | GDF-1 | ...Ser Pro | ......Phe... | ... | | |
| 67 | 60A | ...Gly... | Leu Pro...... | His | | |
| | | 75 | | 80 | | |
| 54 | hBMP-7 (OP-1) | Asp Asp Ser | Ser Asn Val Ile Leu | Lys | | |
| 55 | mBMP-7 (OP-1) | ......... | ......... | ... | | |
| 56 | BMP5 | ......... | ......... | ... | | |
| 57 | BMP6 | ......Asn | ......... | ... | | |
| 58 | Vgr-1 | ......Asn | ......... | ... | | |
| 59 | hOP-2 | ...Ser... | Asn...... | Arg | | |
| 60 | mOP-2 | ...Ser... | Asn...... | Arg | | |
| 61 | DPP | Asn...Gln | ...Thr...Val | ... | | |
| 62 | CBMP-2A | ...Glu Asn | Glu Lys...Val... | ... | | |
| 63 | CBMP-2B | ...Glu Tyr | Asp Lys...Val... | ... | | |
| 64 | BMP3 | ...Glu Asn | Lys......Val... | ... | | |
| 65 | Vgl | ...Asn Asn | Asp......Val... | Arg | | |
| 66 | GDF-1 | ...Asn... | Asp......Val... | Arg | | |
| 67 | 60A | Leu Asn Asp | Glu......Asn... | ... | | |
| | | 85 | | | | |
| 54 | hBMP-7 (OP-1) | Lys Tyr Arg | Asn Met Val Val Arg | | | |
| 55 | mBMP-7 (OP-1) | ......... | ......... | | | |
| 56 | BMP5 | ......... | ......... | | | |
| 57 | BMP6 | ......... | Tyr...... | | | |
| 58 | Vgr-1 | ......... | ......... | | | |
| 59 | hOP-2 | ...His... | ......Lys | | | |
| 60 | mOP-2 | ...His... | ......Lys | | | |
| 61 | DPP | Asn...Gln | Glu...Thr...Val | | | |
| 62 | CBMP-2A | Asn...Gln | Asp......Glu | | | |
| 63 | CBMP-2B | Asn...Gln | Glu......Glu | | | |
| 64 | BMP3 | Val...Pro | ......Thr...Glu | | | |
| 65 | Vgl | His...Glu | ......Ala...Asp | | | |

TABLE II-continued

| SEQ ID NO | | | | | |
|---|---|---|---|---|---|
| 66 | GDF-1 | Gln...Glu | Asp......... | ...Asp | |
| 67 | 60A | ......... | ......Ile | ...Lys | |
|    |     |    90     |             |   95   | |
| 54 | hBMP-7 (OP-1) | Ala Cys Gly | Cys His | | |
| 55 | mBMP-7 (OP-1) | ......... | ...... | | |
| 56 | BMP5 | Ser...... | ...... | | |
| 57 | BMP6 | ......... | ...... | | |
| 58 | Vgr-1 | ......... | ...... | | |
| 59 | hOP-2 | ......... | ...... | | |
| 60 | mOP-2 | ......... | ...... | | |
| 61 | DPP | Gly...... | ...Arg | | |
| 62 | CBMP-2A | Gly...... | ...Arg | | |
| 63 | CBMP-2B | Gly...... | ...Arg | | |
| 64 | BMP3 | Ser...Ala | ...Arg | | |
| 65 | Vgl | Glu...... | ...Arg | | |
| 66 | GDF-1 | Glu...... | ...Arg | | |
| 67 | 60A | Ser...... | ...... | | |
|    |     |           |  100   | | |

†Between residues 56 and 57 of BMP3 is a Val residue; between residues 43
and 44 of GDF-1 lies the amino acid sequence Gly-Gly-Pro-Pro
(SEQ ID NO: 68).

As is apparent from the foregoing amino acid sequence comparisons, some amino acid changes can be made within the generic sequences while retaining the morphogenic activity. The observation of the sequences easily reveals that there are subfamilies within this family: human and mouse BMP-7 are closely related, and with BMP-5, BMP-6, and Vgr-1, form one subfamily. CBMP-2A and CBMP-2B, along with DPP, form another subfamily. The changed amino acid residues are not crucial to the biological activities and the amino acid residues are expected to be interchangeable. As such, a generic sequence having a sequence encompassing all members of the subfamily can be easily understood for each subfamily, and any sequence within the generic sequence is expected to have same or similar activities.

For example, Generic Sequence No. 1 (SEQ ID NO: 24) encompassing the mineralization-countering BMPs (mouse and human BMP-7) and related sequences (BMP-5, BMP-6, and VGR-1, can be described as the following:

```
Generic Sequence 1
                                          (SEQ ID NO: 24)
Leu Tyr Val Ser Phe Xaa Asp Xaa Gly Trp Gln Asp
1               5                   10

Trp Ile Ile Ala Pro Xaa Gly Tyr Ala Ala Xaa Tyr
          15                  20

Cys Xaa Gly Glu Cys Xaa Phe Pro Leu Asn Xaa Xaa
25                  30                      35

Met Asn Ala Thr Asn His Ala Ile Val Gln Thr Leu
              40                  45

Val His Xaa Xaa Xaa Pro Xaa Xaa Val Pro Lys Pro
          50              55                60

Cys Cys Ala Pro Thr Xaa Xaa Asn Ala Ile Ser Val
                  65                  70

Leu Tyr Phe Asp Asp Xaa Ser Asn Val Ile Leu Lys
              75              80

Lys Tyr Arg Xaa Met Val Val Arg Xaa Cys Gly Cys
85                  90                      95
His
``` wherein each Xaa independently is selected from a group of one or more specified amino acids defined as follows:

"Res." means "residue" and; Xaa at res. 6=(Arg or Gln); Xaa at res. 8=(Leu or Val); Xaa at res. 18=(Glu or Lys); Xaa at res. 23=(Tyr, Asn or Phe); Xaa at res. 26=(Glu or Asp); Xaa at res. 30=(Ala or Ser); Xaa at res. 31=(Phe, Leu or Tyr); Xaa at res. 33=(Leu, Val or Met); Xaa at res. 34=(Asn, Asp, Ala, Thr or Pro); Xaa at res. 35=(Ser or Ala); Xaa at res. 36=(Tyr or His); Xaa at res. 51=(Phe, Leu, or Val); Xaa at res. 52=(Ile or Met); Xaa at res. 53=(Asn or Phe); Xaa at res. 55=(Glu or Asp); Xaa at res. 66=(Gln or Lys); Xaa at res. 67=(Leu, or Val); Xaa at res. 88=(Asn or Trp); Xaa at res. 90=(Val, Thr, Ala or Ile); Xaa at res. 92=(Arg, Lys, Val, Asp, Gln or Glu); and Xaa at res. 93=(Ala or Ser). Such Generic Sequence depicts all expected morphogen that preserves the activities of BMP-7. Other generic sequences can be constructed using the subfamily sequences and allowing for interchangeable amino acid residues.

As noted above, certain preferred morphogenic polypeptide sequences useful in this invention have greater than 50% identity, preferably greater than 55%, 60%, 65%, 70%, 80%, 85%, 90%, 95% or even 99% identity, with the amino acid sequence defining the preferred reference sequence of hBMP-7 (OP-1) (especially the conserved six-seven cysteine skeleton of hBMP-7 (OP-1), e.g., residues 38-139 of SEQ ID No: 1), or equivalent regions from other morphogens described in the application. These particularly preferred sequences include allelic and phylogenetic counterpart variants of the BMP-7 (OP-1) and OP-2 proteins, including the *Drosophila* 60A protein, as well as the closely related proteins BMP5, BMP6 and Vgr-1. Accordingly, in certain particularly preferred embodiments, useful morphogenic proteins include active proteins comprising pairs of polypeptide chains within the generic amino acid sequence herein referred to as "OPX" (SEQ ID NO: 25), which defines the seven cysteine skeleton and accommodates the homologies between several identified variants of BMP-7 (OP-1) and OP-2 (BMP-8). Accordingly, each "Xaa" at a given position in OPX independently is selected from the residues occurring at the corresponding position in the C-terminal sequence of mouse or human BMP-7 (OP-1) or —OP-2 (BMP-8). Specifically, 'each "Xaa" is independently selected from a group of one or more specified amino acids as defined below (SEQ ID NO: 25):

```
Cys Xaa Xaa His Glu Leu Tyr Val Ser Phe Xaa Asp
1               5                   10

Leu Gly Trp Xaa Asp Trp Xaa Ile Ala Pro Xaa Gly
              15                  20

Tyr Xaa Ala Tyr Tyr Cys Glu Gly Glu Cys Xaa Phe
25                  30                      35

Pro Leu Xaa Ser Xaa Met Asn Ala Thr Asn His Ala
              40                  45

Ile Xaa Gln Xaa Leu Val His Xaa Xaa Xaa Pro Xaa
      50              55                  60

Xaa Val Pro Lys Xaa Cys Cys Ala Pro Thr Xaa Leu
                  65                  70

Xaa Ala Xaa Ser Val Leu Tyr Xaa Asp Xaa Ser Xaa
              75              80

Asn Val Ile Leu Xaa Lys Xaa Arg Asn Met Val Xaa
85                  90                      95

Ala Cys Gly Cys His
                 100
``` wherein Xaa at res. 2=(Lys or Arg); Xaa at res. 3=(Lys or Arg); Xaa at res. 11=(Arg or Gln); Xaa at res. 16=(Gln or Leu); Xaa. at res. 19=(Ile or Val); Xaa at res. 23=(Glu or Gln); Xaa at res. 26=(Ala or Ser); Xaa at res. 35=(Ala or Ser); Xaa at res. 39=(Asn or Asp); Xaa at res. 41=(Tyr or Cys); Xaa at res. 50=(Val or Leu); Xaa at res. 52=(Ser or Thr); Xaa at res. 56=(Phe or Leu); Xaa at res. 57=(Ile or Met); Xaa at res. 58=(Asn or Lys); Xaa at res. 60=(Glu, Asp or Asn); Xaa at res. 61=(Thr, Ala or Val); Xaa at res. 65=(Pro or Ala); Xaa at res. 71=(Gln or Lys); Xaa at res. 73=(Asn or Ser); Xaa at res. 75=(Ile or Thr); Xaa at res. 80=(Phe or Tyr); Xaa at res. 82=(Asp or Ser); Xaa at res. 84=(Ser or Asn); Xaa at res. 89=(Lys or Arg); Xaa at res. 91=(Tyr or His); and Xaa at res. 96=(Arg or Lys).

The following patents or publications or patent applications disclose morphogens or formula of useful/active morphogens, the entire contents of which are hereby incorporated by reference herein: EP 601106, and U.S. Ser. No. 08/937,755 (filed on Sep. 25, 1997).

The morphogens useful in the methods, composition and devices of this invention include proteins comprising any of the polypeptide chains described above which is in the appropriate subfamily, whether isolated from naturally occurring sources, or produced by recombinant DNA or other synthetic techniques, and includes allelic and species variants of these proteins, naturally occurring or biosynthetic mutants thereof, as well as various truncated and fusion constructs. Deletion or addition mutants also are envisioned to be active, including those which may alter the conserved C-terminal cysteine skeleton, provided that the alteration does not functionally disrupt the relationship of these cysteines in the folded structure. Accordingly, such active forms are considered the equivalent of the specifically described constructs disclosed herein.

The proteins may include forms having varying glycosylation patterns, varying N-termini, a family of related proteins having regions of amino acid sequence homology, and active truncated or mutated forms of native or biosynthetic proteins, produced by expression of recombinant DNA in host cells.

The morphogens contemplated herein can be expressed from intact or truncated genomic or cDNA or from synthetic DNAs in prokaryotic or eukaryotic host cells, and purified, cleaved, refolded, and dimerized to form morphogenically active compositions. The dimeric proteins can be isolated from the culture media and/or refolded and dimerized in vitro to form biologically active compositions, Heterodimers can be formed in vitro by combining separate, distinct polypeptide chains. Alternatively, heterodimers can be formed in a single cell by co-expressing nucleic acids encoding separate, distinct polypeptide chains. See, for example, WO93/09229, or U.S. Pat. No. 5,411,941, for several exemplary recombinant heterodimer protein production protocols. Currently preferred host cells include, without limitation, prokaryotes including *E. coli*, or eukaryotes including yeast (such as *S. cerevisiae*), insect cells, or any suitable mammalian host cells, such as CHO, COS or BSC cells. One of ordinary skill will appreciate that other host cells can be used to advantage. A detailed description of the morphogens useful in the methods, compositions and devices of this invention, including how to make, use and test them for chondrogenic activity, are disclosed in numerous publications, including U.S. Pat. Nos. 5,266,683 and 5,011,691, the specifications of which are incorporated herein by reference.

In still another preferred embodiment, useful morphogenically active proteins have polypeptide chains with amino acid sequences comprising a sequence encoded by a nucleic acid that hybridizes with DNA or RNA encoding reference morphogen sequences, e.g., C-terminal sequences defining the conserved seven cysteine skeletons of BMP-7 (OP-1), OP-2 (BMP-8), BMP5, BMP6, Vgr-1, 60A, GDF-3, GDF-5, GDF-6, GDF-7 and the like. As used herein, high stringency hybridization conditions are defined as hybridization according to known techniques in 40% formamide, 5×SSPE, 5×Denhardt's Solution, and 0.1% SDS at 37° C. overnight, and washing in 0.1×SSPE, 0.1% SDS at 50° C. Standard stringency conditions are well characterized in standard molecular biology cloning texts. See, for example, MOLECULAR CLONING—A LABORATORY MANUAL, 2nd Ed., ed. by Sambrook, Fritsch and Maniatis (Cold Spring Harbor Laboratory Press: 1989); DNA CLONING, Volumes I and II (D. N. Glover ed., 1985); OLIGONUCLEOTIDE SYNTHESIS (M. J. Gait ed., 1984); NUCLEIC ACID HYBRIDIZATION (B. D. Hames & S. J. Higgins eds. 1984); and B. Perbal, A PRACTICAL GUIDE TO MOLECULAR CLONING (1984).

In other embodiments, as an alternative to the administration of a morphogenic protein, an effective amount of an agent competent to stimulate or induce increased endogenous morphogen expression in a mammal may be administered by any of the routes described herein. Such a morphogen inducer may be provided to a mammal, e.g., by systemic administration to the mammal or by direct administration to the blood vessels. A method for identifying and testing inducers (stimulating agents) competent to modulate the levels of endogenous morphogens in a given tissue is described in published applications WO 93/05172 and WO 93/05751, each of which is incorporated by reference herein. Briefly, candidate compounds are identified and tested by incubation in vitro with test tissue or cells, or a cultured cell line derived therefrom, for a time sufficient to allow the compound to affect the production, i.e., cause the expression and/or secretion, of a morphogen produced by the cells of that tissue. Suitable tissues, or cultured cells of a suitable tissue, are preferably selected from renal epithelium, ovarian tissue, fibroblasts, and osteoblaFsts.

In yet other embodiments, an agent which acts as an agonist of a morphogen receptor may be administered instead of the morphogen itself. Such an agent may also be referred to as a morphogen "mimic," "mimetic," or "analog." Thus, for example, a small peptide or other molecule which can mimic the activity of a morphogen in binding to and activating the morphogen's receptor—may be employed as an equivalent of the morphogen. Preferably the agonist is a full agonist, but partial morphogen receptor agonists may also be advantageously employed. Methods of identifying such agonists are known in the art and include assays for compounds which induce morphogen-mediated responses (e.g., induction of differentiation of metanephric mesenchyme, induction of endochondral bone formation). For example, methods of identifying morphogen inducers or agonists of morphogen receptors may be found in U.S. Ser. No. 08/478,097 filed Jun. 7, 1995; U.S. Ser. No. 09/791,946, filed Feb. 22, 2001; U.S. Pat. Nos. 5,834,188; 6,273,598; WO 97/26277; EP 0876401; U.S. Provisional Application No. 60/080,032, filed on Mar. 30, 1998; U.S. Provisional Application No. 60/296,291, filed on Jun. 10, 2001; U.S. Provisional Application No. 60/354,820, filed on Feb. 5, 2002; and U.S. Provisional Application filed on Apr. 10, 2002 (first named inventor Peter Keck, title: "MORPHOGEN ANALOGS AND METHODS FOR PRODUCING THEM"), the disclosures of which are incorporated herein by reference.

The OP/BMP family of morphogens of the invention is also characterized by biological activities which may be readily ascertained by those of ordinary skill in the art. Specifically, a morphogen of the present invention is (a) capable of inducing chondrogenesis in the Reddi-Sampath ectopic bone assay (Sampath and Reddi (1981), Proc. Natl. Acad. Sci. USA 78:7599-7603) or a substantially equivalent assay, (b) capable of significantly preventing, inhibiting, delaying or alleviating the progressive loss of renal function in a standard animal model of chronic renal failure, or (c) capable of causing a clinically significant improvement in a standard marker of renal function when administered to a mammal in, or at risk of, chronic renal failure.

The Reddi-Sampath ectopic bone assay is well known in the art as an assay of chondrogenic activity. The assay, which can be easily performed, is described and discussed in, for example, Sampath and Reddi (1981) and function which characterizes chronic renal failure.

Finally, the morphogens of the present invention may be evaluated for their therapeutic efficacy in causing a clinically significant improvement in a standard marker of renal function when administered to a mammalian subject (e.g., a human patient) in, or at risk of, chronic renal failure. Such markers of renal function are well known in the medical literature and include, without being limited to, rates of increase in BUN levels, rates of increase in serum creatinine, static measurements of BUN, static measurements of serum creatinine, glomerular filtration rates (GFR), ratios of BUN/creatinine, serum concentrations of sodium ($Na^+$), urine/plasma ratios for creatinine, urine/plasma ratios for urea, urine osmolality, daily urine output, and the like (see, for example, Brenner and Lazarus (1994), in Harrison's Principles of Internal Medicine, 13th edition, Isselbacher et al., eds., McGraw Hill Text, New York; Luke and Strom (1994), in Internal Medicine, 4th Edition, J. H. Stein, ed., Mosby-Year Book, Inc. St. Louis).

Pharmaceutical Compositions

The pharmaceutical compositions useful in this invention may be in a variety of forms. These include, for example, liquid, solid or semi-solid dosage forms such as liquid solutions, infusible solutions, emulsions, gels, suspensions, tablets, and pills. The preferred form depends on the intended mode of administration and the therapeutic application and may be selected by one skilled in the art. Modes of administration may include intravenous, oral, parenteral, intramuscular, intraperitoneal, subcutaneous, intralesional, surgical implantation or topical administration. The compositions may be formulated in dosage forms appropriate for each route of administration. In some embodiments, the pharmaceutical compositions of this invention will be administered into the vascular tissue. In other embodiments, the pharmaceutical compositions of this invention will be administered in the vicinity of the target vascular tissue. In yet other embodiments, the pharmaceutical is administered at a site distal to the target tissue. For example, in some embodiments, the pharmaceutical compositions of this invention may be administered systemically.

The compositions also will preferably include conventional pharmaceutically acceptable carriers well known in the art (see, e.g., Remington's Pharmaceutical Sciences, 16th Ed., Mac Publishing Company (1980)). Such pharmaceutically acceptable carriers may include other medicinal agents, carriers, genetic carriers, adjuvants, excipients, etc., such as human serum albumin or plasma preparations. Preferably, the carrier is isotonic. Examples of such carrier vehicles include water, saline, Ringer's solution, buffered aqueous solutions, hyaluronan, hyaluronic acid and dextrose solution. Non-aqueous vehicles such as fixed oils and ethyl oleate are also useful herein.

In some embodiments, the compositions of this invention are sustained release formulations, slow delivery formulations, or formulations whereby the clearance of the morphogen is delayed. There are numerous delivery materials available for preparing these compositions, including but not limited to microspheres (e.g., polylactic/polyglycolic acid polymers), liposomes, polyethylene glycol (PEG), gelatin, and other microparticulate delivery systems or sustained release formulations. In some embodiments, the morphogen is covalently linked to the delivery material.

Various growth factors, cytokines, hormones, trophic agents and therapeutic agents including antibiotics and chemotherapeutic agents, enzymes, enzyme inhibitors and other bioactive agents may also be included in the pharmaceutical compositions.

Dosage levels of between about 1 µg and about 1000 µg per day, preferably between 3 µg and 50 µg per day of morphogen are useful. As the skilled artisan will appreciate, lower or higher doses than those recited may be required. The compositions are preferably in the form of a unit dose and will usually be administered as a dose regimen that depends on the particular tissue treatment. The composition may be administered once or multiple times, with an administration frequency, as is known in the art, that optimizes tissue healing or repair. The composition can, for example, be administered daily, weekly, monthly, semimonthly, bimonthly, quarterly, biyearly or yearly. Specific dosage and treatment regimens for any particular patient will depend upon a variety of factors, including the activity of morphogen employed, the age, body weight, general health status, sex, diet, time of administration, rate of excretion, drug combination, the severity of the tissue damage and the judgment of the treating physician.

As a general matter, the morphogens of the present invention may be used in the preparation of medicaments for the treatment of any mammalian subject at risk of or afflicted with CKD, vascular sclerosis, neointimal hyperplasia and/or vascular calcification in a subject. Further, methods of the present invention may be applied to the treatment of any mammalian subject at risk of or afflicted with CKD, vascular sclerosis, neointimal hyperplasia and/or vascular calcification. The invention is suitable for the treatment of any primate, preferably a higher primate such as a human. In addition, however, the invention may be employed in the treatment of domesticated mammals which are maintained as human companions (e.g., dogs, cats, horses), which have significant commercial value (e.g., goats, pigs, sheep, cattle, sporting or draft animals), which have significant scientific value (e.g., captive or free specimens of endangered species, or inbred or engineered animal strains), or which otherwise have value.

EXAMPLES

Example 1

Animals and diets: LDL receptor null ($LDLR^-/\_$) mice on a C57Bl/6J background were purchased from Jackson Laboratory (Bar Harbor, Me.) and bred in a pathogen-free environment. Animals were weaned at three weeks to a chow diet [1:1 mixture of Pico Lab rodent chow 20 and mouse chow 20, 6.75% calories as fat]. At 10 weeks, animals were either continued on this chow diet or initiated on a high cholesterol (0.15%) diet containing 42% calories as fat [Harlan Teklad, Madison Wis., Product No. TD88137]. For some animals, the diet was supplemented with 1% or 3% $CaCO_3$. Animal diets supplemented with $CaCO_3$ were previously reported.[20] Animals were given access to water ad libitum. BMP-7 was provided by Johnson and Johnson (Raritan, N.J.). The Washington University Animal Care committee approved the study protocol. Animal experiments were performed according to the NIH Guide for the Care and Use of Laboratory Animals and approved by the Washington University Animal Studies Committee.

Example 2

Induction of CKD: A two-step procedure was utilized to create uremia as previously described. (Davies 2003; Lund, 2004)[19;21] Saphenous vein blood samples were taken 1 week following the second surgery to assess baseline post-surgical renal function. Animals were sacrificed under anesthesia 28 weeks post natal. At the time of sacrifice, blood was taken by intracardiac stab, and the heart and aorta dissected en bloc. The BMP-7 treated group received intraperitoneal injection of BMP-7 10 µg/kg dry weight once weekly in 100 µl vehicle [mannitol (5% w/v), NaAcetate buffer (20 mM, pH 4.0-4.5), sterile water]. This is the same dose used in our previous studies. (Davies 2003; Davies 2005)[19;20]

Animals were allocated to one of seven CKD high fat fed groups after the second surgery: Other control Groups included LDLR−/− sham operated mice on chow diet, and LDLR−/− mice with CKD on chow diet. C57B16 WT mice fed chow served as the normal benchmark source. Data from these control groups are not presented. Group 1 were LDLR−/− mice on the high fat diet sacrificed at 22 weeks. Group 2 were LDLR−/− mice with CKD fed the high fat diet and treated weekly from 22 to 28 weeks with vehicle IP. This group was expected to develop high serum phosphorus and VC. Group 3 was the first treatment group. These were LDLR−/− mice with CKD on high fat diet that received BMP-7 treatment (10 µg/kg IP weekly). Group 4 were LDLR−/− mice with CKD on high fat diet treated with sevelamer $CO_3$ 1%. Group 5 were LDLR−/− mice with CKD on high fat diet treated with sevelamer $CO_3$ 3%. Group 6 were LDLR−/− mice with CKD on high fat diet treated with $CaCO_3$ 3%. Group 7 were LDLR−/− mice with CKD on high fat diet treated with $CaCO_3$ 3%. Once the mice were randomized into groups, they were allowed to develop calcification from weeks 14 through weeks 22 post natal. Therapy was initiated at 23 weeks postnatal and continued until week 28 postnatal at which time the mice were examined.

Example 3

Blood tests: Serum was analyzed on the day of blood draw for blood urea nitrogen [BUN], cholesterol, calcium and phosphate by standard laboratory methods. Before initiation of therapy, blood was obtained through saphenous vein. At the time of sacrifice, blood was obtained through intracardiac stab.

Example 4

Tissue Preparation: Resected specimens were flash frozen in liquid nitrogen, then divided as follows: the heart, ascending aorta and aortic arch were separated from the descending aorta, and bisected sagittally through the aortic outflow tract. The descending aorta was bisected coronally, approximately halfway along its length. In order to visualize calcification in the tissue sections, Slices (5 µm thick) were cut and stained with von Kossa and Trap staining.

Example 5

Chemical Calcification Quantitation: similar to our previous experimental plans (Davies 2003; Davies 2005).[19;20] Aorta and hearts were dissected at sacrifice, and all extraneous tissue removed by blunt dissection under a dissecting microscope. Tissues were desiccated for 20-24 hours at 60° C., weighed and crushed to a powder with a pestle and mortar. Calcium was eluted in 1N HCL for 24 hours at 4° C. Calcium content of eluate was assayed using a cresolphthalein complexone method (Sigma, St Louis), according to manufacturers instructions, and results were corrected for dry tissue weight for Heart and Aorta.

Example 6

Cell Culture: Human adult aorta were obtained from seven cadaveric organ donors rejected because of atherosclerosis by Mid-America Transplant Services (St. Louis, Mo.) and enzymatically digested to obtain Human Smooth Muscle Cells (HSMC). Medial tissue was separated from the adventia and intima and digested with collagenase type I (Worthington, Lakewood, N.J.) 2 mg/ml for 1 hr, and washed with Hank's balanced salt solution (HBSS). Further digestion followed with collagenase type II 1 mg/ml (Worthington, Lakewood, N.J.) and elastase 0.25 mg/ml (Worthington, Lakewood, N.J.) for 4 hrs. Cell suspensions were washed twice with HBSS and cultured in T-75 flasks for three weeks in a 95%/5% air/$CO_2$ humidified environment at 37° C. The growth medium used was DMEM containing 4.5% glucose (high glucose), 10% fetal bovine serum (FBS, Atlas, Fort Collins, Colo.), 1 mM sodium pyruvate, 100 units/ml Penicillin and 100 mg/ml Streptomycin (Sigma, St Louis, Mo.). Cell purity was assessed by positive immunostaining for α-smooth muscle actin and calponin and for the absence of von Willebrand factor. In all experimental protocols, cells were seeded at $1 \times 10^5$ cells/well in six-well plates. Medium was changed on the first day and every third day thereafter. In all cases, cells used were between passages two and five (Table 3).

TABLE 3

Characterization of hVSMC culture matrix Ca content isolated from atherosclerotic aortas

| Donor # | Passage # studied | Basal condition | Effects of 2 mM $PO_4$ Matrix Ca content | Effects of 10 ng/ml BMP-7 |
|---|---|---|---|---|
| 1 | 2 | 4.3 | 29.9 | 20.3 |
| 2 | 3 | 6.5 | 31.1 | 20.6 |
| 3 | 3 | 5.3 | 28.7 | 18 |
| 4 | 2 | 5.6 | 28.6 | 17.9 |
| 5 | 3 | 5.7 | 35.6 | 25.8 |
| 6 | 3 | 4.9 | 31.4 | 19.8 |
| 7 | 2 | 5.5 | 33.5 | 22.1 |

Example 7

Induction of Calcification: At the time of confluence, cells were switched to mineralization medium consisting of DMEM supplemented with 1 or 2 mM $P_i$. For cells exposed to BMP-7 treatment, fresh mineralization medium containing either vehicle (mannitol, acetic acid, acetate) or BMP-7 in vehicle was added at 0.1, 1.0, 10, or 100 ng/ml. The medium was changed every two or three days. Noggin, (Pepro Tech., Rocky Hill, N.J.), was added to the mineralization medium at a final concentration of 100 ng/ml. Calcium content was quantified and normalized to cellular protein as described. (Jono 2000; Moe S. M. et al., *Kidney Int* 67:2295-2304, 2005)[11;52]

Example 8

RT-PCR: RNA was extracted from cell cultures using RNeasy Mini Kits (Qiagen, Valencia, Calif.). Semi-quantitative RT-PCR was conducted using Roche 1$^{st}$ Strand cDNA Synthesis Kit (Indianapolis, Ind.) and PCR kit from Invitrogen (Grand Island, N.Y.) according to manufacturer's instructions using a two-step method. 1 µg of total RNA was reverse transcribed and random primers were added for 60 min at 42° C., prior to PCR. Forward and Reverse primers (Table 4) were added and the reactions subjected to PCR for 20-35 cycles. The number of cycles necessary to amplify cDNA but remain within the exponential amplification range was determined for each primer set. GAPDH was used as internal standard to assess loading. Genomic contamination was assessed by heat inactivation of the reverse transcriptase prior to RT-PCR. Primers were designed using Vector NTI soft ware (Invitrogen, Grand Island, N.Y.) and optimal conditions for each prime pairs were determined (Table 4). A Perkin-Elmer DNA Thermal Cycler was used to perform the reaction. Products were separated on a 2% agarose E-gel (Invitrogen, Grand Island, N.Y.), and visualized with ethidium bromide. The band intensity was analyzed first by scanning the gel on a Typhoon 9410 gel imager (Amersham Biosciences), quantified by using TotalLab software v2003.03 (Nonlinear Dynamics, Durham, N.C.) and normalized for loading by comparison to GAPGH. Negative controls were performed by inactivating the reverse transcriptase by boiling for 5 min prior to RT-PCR to insure that genomic DNA was not amplified.

Example 9

Real Time Quantitative RT-PCR: Following reverse transcription performed as above, real time was performed using the MX 4000 (Strategene, La Jolla, Calif.), SYBR Green from Sigma (St. Louis) and the PCR kit from Invitrogen. Each reaction was performed in triplicate at 95° C., 45 sec, and 60° C., 30 sec, and 60 sec at 72° C. for 40 cycles. This was followed by a melt cycle, which consisted of stepwise increase in temperature from 72° C. to 99° C. A single predominant peak was observed in the dissociation curve of each gene, supporting the specificity of the PCR product. Ct numbers (threshold values) were set within the exponential phase of PCR and were used to calculate the expression levels of the genes of interest. GAPDH was used as an internal standard and used to normalize the values. A standard curve consisting of the $c_T$ versus log cDNA dilutions (corresponding to the log copy numbers) was generated by amplifying serial dilutions of cDNA corresponding to an unknown amount of amplicon.

Example 10

Osterix siRNA Constructs: The human osterix (osx) siRNA target sequences were designed by Enhanced siDirect Primer Sequence

| Gene | Primer Sequence (5'-3') | Product Length (bp) | $T_m$ (°C.) | SEQ ID NO. |
|---|---|---|---|---|
| Myocardin | F GAGAGGTCCATTCCAACTGCTCAGATGAAG | 249 | 26 | 30 |
|  | R GTCTTCACTTCGAGTCTGATCCGGAGAAAG |  |  | 27 |
| Calponin | F AGCATGTCCTCTGCTCACTTCAACC | 154 | 28 | 32 |
|  | R CGTCCATGAAGTTGTTGCCGAT |  | 29 | 33 |
| SM22 alpha | F TGGGTGGTGATCCACTGGATC | 179 | 30 | 34 |
|  | R TTGCCTTGAGTCAGTGCGCC |  | 31 | 35 |
| αSM | F AGCCCAGCCAAGCACTGTCA | 130 | 32 | 36 |
|  | R GAGCATCGTCCCCAGCAAAG |  | 33 | 37 |
| Myocin heavy chain | F GAAGATCGTCGACATGTACAAGGG | 122 | 34 | 38 |
|  | R TGCATAGAATGGACTGGTCCTCC |  |  | 35 |
| Matrix Gla Protein (MGP) | F GCTACACAAGACCCTGAGACTGACC | 192 | 36 | 40 |
|  | R TCTCCATCTCTGCTGAGGGGAT |  | 37 | 41 |
| Cbfa1 | F CACGACAACCGCACCATGGT | 181 | 38 | 42 |
|  | R TGACAGTAACCACAGTCCCATCTG |  |  | 39 |
| MSX2 | F GCTGGTGAAGCCCTTCGAGA | 173 | 40 | 44 |
|  | R ATGTGGTAAAGGGCGTGCG |  | 41 | 45 |
| Osterix | F AGTTCATGGCTCCAGTCCCC | 146 | 42 | 46 |
|  | R TGGAGGCTGAAAGGTCACTGC |  | 43 | 47 |
| BMP2 | F AGCCAACACTGTGCGCAGCT | 140 | 44 | 48 |
|  | R CCTGAAGCTCTGCTGAGGTGATAA |  |  | 45 |
| Osteocalcin | F ATGAGAGCCCTCACACTCCTC | 297 | 46 | 50 |
|  | R GCCGTAGAAGCGCCGATAGGC |  | 47 | 51 |
| GAPDH | F TCCTGTTCGACAGTCAGCCG | 122 | 48 | 52 |
|  | R TGGTGACCAGGCGCCCAATA |  | 49 | 53 |
| Mouse Osterix | F TCCCTTCTCAAGCACCAATGGACT | 230 | 50 | 54 |
|  | R AGCTGTGAATGGGCTTCTTCCTCA |  |  | 51 |
| Mouse GAPDH | F TGTTCCAGTATGACTCCACTCACG | 170 | 52 | 56 |
|  | R GAAGACACCAGTAGACTCCACGACA |  |  | 53 |

(RNAi Co., Ltd.) (Table 4). The 63-mer sense and antisense strands of DNA oligonucleotides were synthesized by Integrated DNA Technologies. Construction of a retroviral vector for delivery of siRNA was performed using the pSilencer 5.1-H retroviral system (Ambion) according to the manufacturer's instructions. Scrambled siRNA negative control retroviral vector was purchased from Ambion.

Example 11

Establishment of stably infected cells: Subconfluent Phoenix-A, which was a gift from Dr. Garry Nolan (Stanford University School of Medicine, Stanford, Calif.) packaging cells were transfected with siRNA retroviral vectors (8 μg DNA/100 mm dish) using FuGene 6 (Roche). After 48 h, the supernatant was collected, filtered through a 0.45 μm syringe filter, and used to transduct target cells. Each supernatant (5 ml) was mixed with 8 μg/ml polybren (Sigma). This infection cocktail (10 ml) was used to infect into SaOs cells ($2\times10^5$ cells/100 mm dish) for 6 h. Infected cells were selected in the presence of 4 μg/ml puromycin (Sigma) for three days, and infected cells were assayed.

Example 12

Immunoblotting: To evaluate the effect of knock down by siRNA, nuclear lysate of cells was assayed by immunoblotting using specific antibodies for osterix (Santa Cruz Biotechnology, Inc.) and histone H3 (Cell Signaling). Histone H3 antibodies were used as a loading control. Immunoblotting methodologies are well known in the art.

Example 13

Mineralization assay: To induce mineralization in vitro, infected cells were cultured in serum free HL-1 media (Lonza) with 50 ug/ml ascorbic acid (Sigma) for 7 days. After 7 days culture, infected cells were stained by von Kossa or alizarin red to detect mineralization (1, 2). For calcium quantification, calcium was dissolved in 0.1 M Tris buffer (pH 7.2) including 0.1 Triton X-100 and 4 N HCL for 16 h after sonication. The content of dissolved calcium was measured by Calcium C-Test (Wako).

Example 14

Statistical Analysis: Data were analyzed for statistical significance ($P<0.05$) using ANOVA. Comparisons were made between animals sacrificed at 22 weeks (control group) and those sacrificed at 28 weeks that were treated with BMP-7 or $CaCO_3$. For the cell culture, system data was analyzed for statistical significance ($P<0.05$) using ANOVA. These analyses were performed with the Systat, Software Inc, (Point Richmond, Calif.).

Example 15

Quantitation of aortic Ca. Quantitation of aortic Ca in fat fed mice with CKD induced at 14 weeks and euthanized at 22 weeks post natal demonstrated CKD stimulated calcification (FIG. 1A). Mice were treated with 10 mcg/kg BMP-7 injected intraperitoneally once weekly. Panel A shows the change in the degree of vascular calcification increased from 22 wks to 28 wks in vehicle treated animals, but aortic calcium decreased in animals treated with BMP-7. Panel B shows the level of phosphorus in the sera of control animals and BMP-7 treated animals. Untreated, it was unchanged between 22 wks and 28 wks, but was reduced to normal levels by treatment with BMP-7. The data are expressed as group mean±SEM, n=4-7. Therapy with the vehicle for six weeks beginning at weeks 22 post natal to week 28 post natal resulted in further accumulation of vascular calcium (FIG. 1A). Therapy with BMP-7, 10 μg/kg IP weekly, the same dose used in prior prevention trials (Davies 2003; Davies 2005),[19;20] for the period 22-28 weeks produced a significant reduction of aortic calcification compared to the 22 week start point (FIG. 1A) and correction of hyperphosphatemia (FIG. 1B).

Example 16

Direct effect of hyperphosphatemia on calcification. Since BMP-7 has actions directly on the vasculature (Dorai H, et al., J. Cellular Physiol. 184:37-45, 2000; Dorai H, and Sampath T K, J. Bone Joint Surg. 83:S70-S78, 2001)[28;29] in addition to decreasing hyperphosphatemia, the inventors of the instant invention analyzed the effects of control of hyperphosphatemia alone. The inventors of the instant invention initially chose sevelamer $CO_3$, a non-absorbable binder of intestinal lumen phosphate and bile salts to correct hyperphosphatemia, but this binder, while effective (Table 5), had pleotropic actions. (Mathew S et al., J. Am. Soc. Nephrol. 18:122-130, 2007)[30]

TABLE 5

Biochemical parameters in the various groups of animals

| Group | Group 1 | Group 2 | Group 3 | Group 4 | Group 5 | Group 6 | Group 7 |
| --- | --- | --- | --- | --- | --- | --- | --- |
| Mouse Strain | LDLR-/- | LDLR-/- | LDLR-/- | LDLR-/- | LDLR-/- | LDLR-/- | LDLR-/- |
| Diet | Fat | Fat | Fat | Fat | Fat | Fat | Fat |
| Surgery | CKD | CKD | CKD | CKD | CKD | CKD | CKD |
| Weeks post natal | 22 | 28 | 28 | 28 | 28 | 28 | 28 |
| Treatment | | | BMP-7 | Sevelamer 1% | Sevelamer 3% | CaCO3 3% | Lanthanum 3% |
| N | 7 | 7 | 4 | 6 | 5 | 5 | 5 |
| Presurgical Weight | 21.74 ± .751 | 17.6 ± .390 | 20.05 ± .674 | 22 | 22 | 19.95 ± .712 | 17.4 ± .702 |
| Weight at Sacrifice | 21.64 ± .954 | 18.3 ± .839 | 21.47 ± .383 | 29 | 28 | 20.5 ± .694 | 19.5 ± .687 |
| Calcium (mg/dl) | 10.55 ± .396 | 7.8 ± .214 | 8.37 ± .229 | 10.4 ± .23 | 13 ± .9 | 6.9 ± .589 | 8.2 ± .3 |

TABLE 5-continued

Biochemical parameters in the various groups of animals

| Phosphorus (mg/dl) | 10.8 ± .802 | 10.94 ± 1.092 | 6.325 ± .471 | 8.4 ± .9 | 6.2 ± .4 | ND | 9.7 ± .4 |
|---|---|---|---|---|---|---|---|
| BUN (mg/dl) | 53.54 ± 3.93 | 62.71 ± 3.74 | 52.50 ± 5.172 | 67 ± 7.5 | 59 ± 7.4 | 58 ± 10.625 | 40 ± 5.3 |
| Glucose (mg/dl) | 288 ± 122.8 | 247 ± 24 | 191 ± 13.8 | 291 ± 21 | 337 ± 68 | 124 ± 13.2 | 201 ± 19 |
| Cholesterol (mg/dl) | 1210 ± 526.2 | 1188 ± 129.6 | 911.6 ± 93.7 | 656 ± 137 | 675 ± 56.8 | ND | 889 ± 80 |

ND—(Not Done, serum used in development of a new assay for fetuin). Effects of $CaCO_3$ on serum Pi, glucose and cholesterol were reported by Davies et al.[20]

Figure 2:
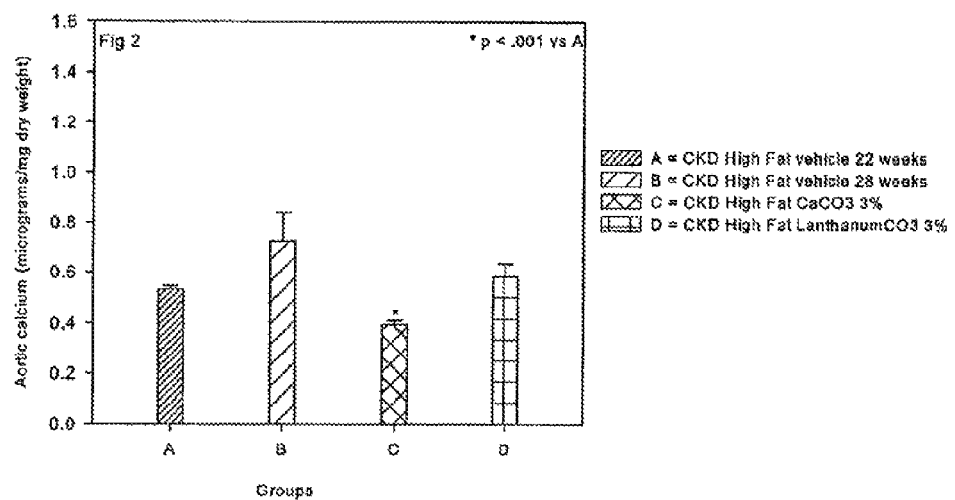
FIG. 2 shows the effects of $CaCO_3$ and $LaCO_3$, both 3% mixed in the diet, on vascular calcification in CKD.

Thus, the inventors of the instant invention chose $CaCO_3$, whose actions may be limited to phosphate binding when well mixed in the food, and if the serum Ca is not affected. $LaCO_3$, another non-calcium containing phosphate binder used clinically, was also studied. While vascular calcification significantly increased from 22 wks to 28 wks in vehicle treated animals, aortic calcium was decreased below levels at 22 wks in animals treated with 3% $CaCO_3$. There was no significant change from 22 wks in the 3% $LaCO_3$ treated animals. The data are expressed as group mean±SEM, n=4-5. $CaCO_3$ added to the diet significantly decreased vascular calcification compared to the 22 weeks start point animals similar to the BMP-7 effects (FIG. 2). The treatment actions of $CaCO_3$ were similar to our published studies demonstrating prevention of VC when hyperphosphatemia was prevented by $CaCO_3$. (Davies 2005)[20] $CaCO_3$ did not affect the serum Ca (Table 5). $LaCO_3$ also prevented the increase in vascular calcification from 22 to 28 weeks similar to $CaCO_3$, but did not reduce vascular calcium levels below those observed at 22 weeks. Sevelamer $CO_3$ therapy reduced the serum cholesterol, but none of the other treatments affected the hypercholesterolemia of the LDLR-/- mice.

Figure 3:
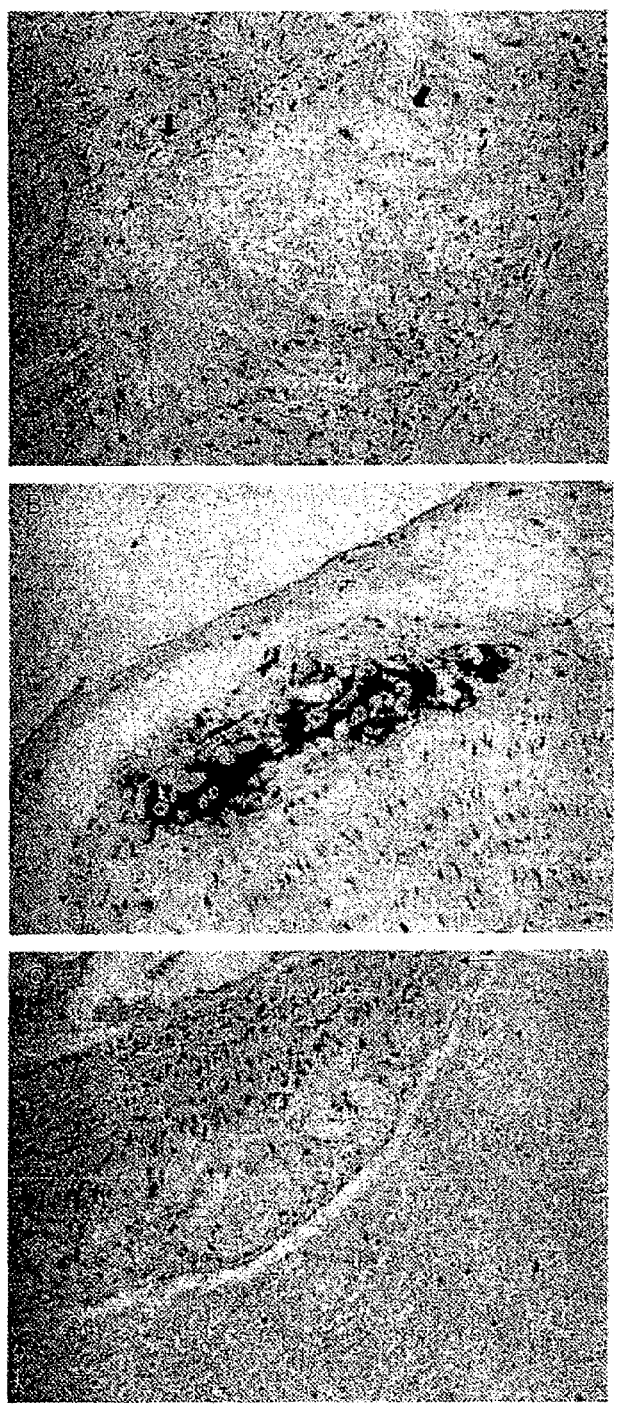
FIG. 3 shows sections of the proximal aorta demonstrating large calcified atherosclerotic plaques in the LDLR–/– high fat fed mice.

Additional mice were enrolled to the study for qualitative analysis of aortas to quantitate the effects of the treatments, because aortas of the experimental animals were destroyed by the technique of quantifying the aortic calcium content. Vascular calcification was largely aortic atherosclerotic plaque associated (FIG. 3), and punctate calcifications in the tunica media were observed. Panel A: Large lipid laden plaque (between arrows) in proximal aorta of a sham-operated high fat fed LDLR-/- mouse. Thick arrows identify focal calcifications in the base of the plaque. Panel B: A large calcified plaque (between arrows) in the proximal aorta of a CKD high fat fed LDLR-/- mouse. Panel C: A large lipid laden plaque (between arrows) in the proximal aorta of a BMP-7 treated CKD high fat fed LDLR-/- mouse. The stain is alizarin red. Magnification is 400× in A-C. Treatment with BMP-7, $CaCO_3$, or $LaCO_3$ diminished plaque associated calcium deposition, but they did not decrease the size of the atherosclerotic lesions (FIG. 3).

Example 17

Figure 4:
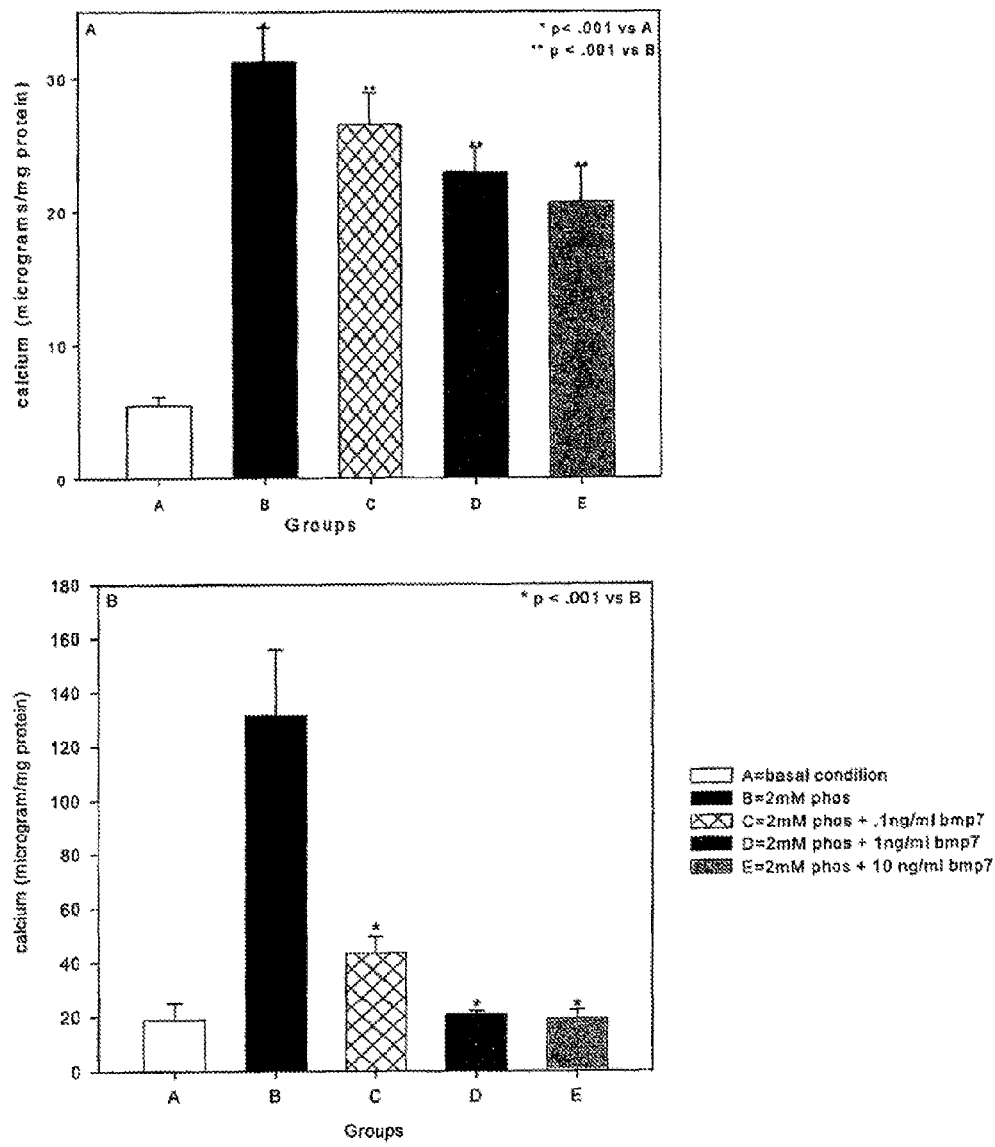
FIG. 4 shows that matrix mineralization is stimulated in cultures of human vascular smooth muscle cells (hVSMC) isolated from atherosclerotic donors.

In vitro matrix mineralization. In order to analyze the mechanism of phosphorus stimulated vascular calcification, the inventors of the instant invention examined matrix mineralization by human vascular smooth muscle cells (hVSMC) isolated from atherosclerotic donors (Table 3) in vitro to mimic this atherosclerotic mouse model. The inventors of the instant invention increased the media phosphorus to mimic the hyperphosphatemia of CKD. The concept of the model follows previously established calcifying vascular smooth muscle cell culture systems[10-12] adapted to human tissues. The hVSMC used herein, did not mineralize the extracellular matrix in basal conditions, but when exposed to an increase in phosphorus of 1 mM over that already present in the culture media (final Pi 2 mM), the hVSMC mineralized their matrix over time (FIG. 4). hVSMC from seven donors were grown in DMEM as described in Example 6 (group A) or DMEM supplemented with 1 mM $NaH_2PO_4/NaHPO_4$, pH 7.4 (group B). In groups C, D, and E, 0.1, 1 and 10 ng/ml of BMP-7, respectively, were added to the $NaH_2PO_4/NaHPO_4$ supplemented media. Cultures were ended at 14 days (A) and 21 days (B). The data are mean±SEM, n=7 donors. BMP-7 exposure for 14 (FIG. 4A) or 21 days (FIG. 4B) in high phosphorus media decreased mineralization of the ECM.

Example 18

Figure 5:
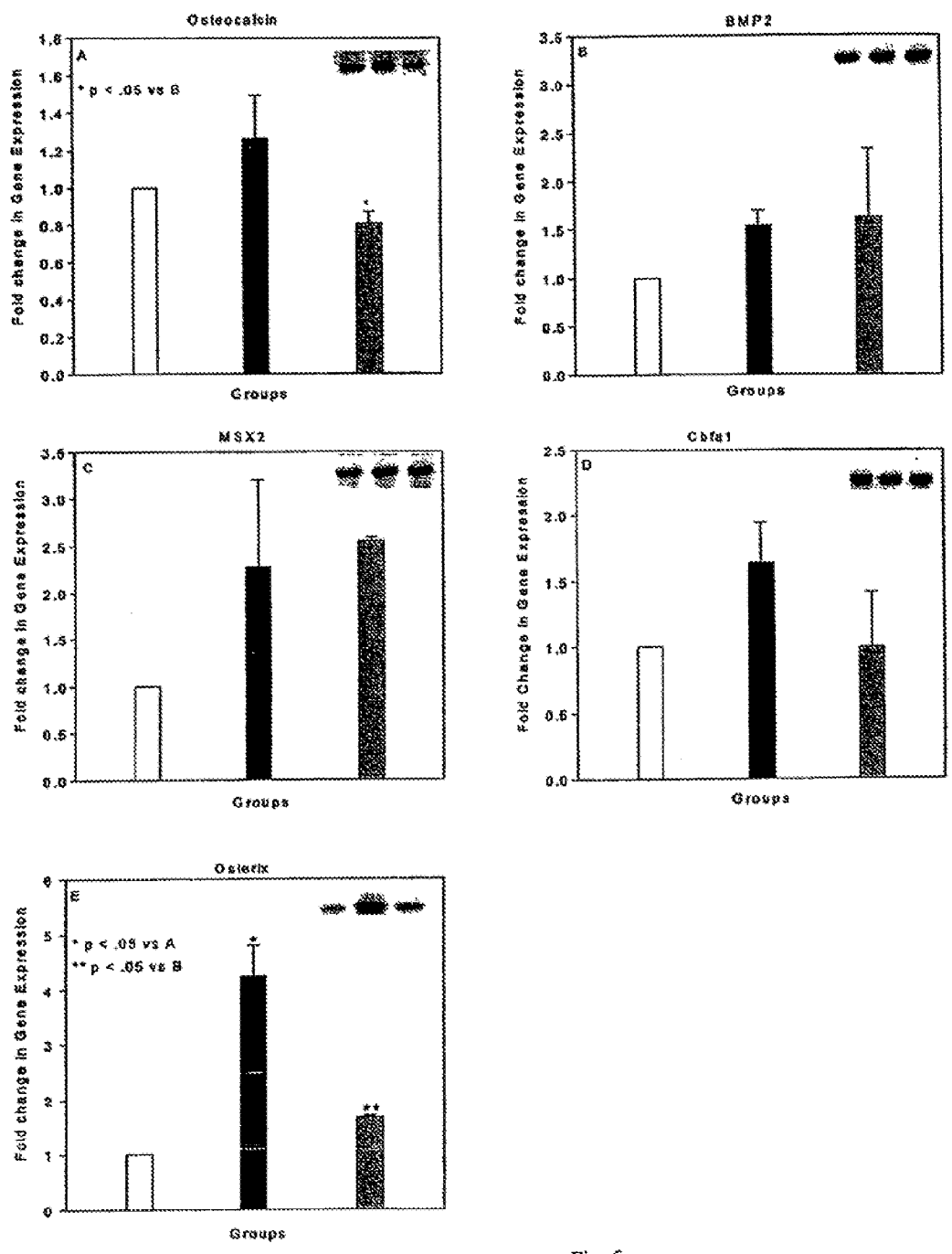
FIG. 5 shows the stimulation of a BMP-2/MSX2 directed osteoblastic differentiation program by $NaH_2PO_4/NaHPO_4$ through induction of osterix.

Stimulation of osteoblastic differentiation through osterix induction. RT-PCR was used to demonstrate the hVSMC primary cultures expressed osteocalcin, the marker of the differentiated osteoblast (Aubin J E, Liu F: The osteoblast lineage. Basal levels of gene expression in hVSMC cultured in DMEM as described in Example 6 and detected by RT-PCR (insets) were set as a reference value of 1 (open bars, group A). Fold induction by high phosphorus (2 mM $NaH_2PO_4/(Na)_2HPO_4$) culture media (black bars, group B) and 2 mM phosphorus plus 10 ng/ml BMP-7 (shaded bars, group C) was determined. An osteoblastic transcriptional program directed by BMP-2/MSX2 was present in hVSMC cultures as demonstrated by the presence of osteocalcin (A), BMP-2 (B), MSX2 (C), and RUNX2 (D), gene transcription. Osterix (E) was only weakly expressed in basal culture conditions. Phosphorus stimulated transcription of osterix (E). BMP-7 inhibited osterix and osteocalcin expression. The data in A-E were normalized to the expression level in basal culture conditions and expressed as fold induction, mean±SEM, n=3. In: *Principles of Bone Biology*, edited by Bilezikian J P et al., New York, Academic Press, 1996, pp 51-67; Hoffmann H M et al., *Proc. Nat. Acad. Sci. USA* 91:12887-12891, 1994)[31,32] (FIG. 5A), in agreement with the previous immunohistologic studies in vivo, (Davies 2003)[19] by the inventors and the colleagues, suggesting that osteoblastic differentiation may be the mechanism of heterotopic mineralization. Transcription of BMP-2, and MSX2, inducers of osteoblastic differentiation, (Cheng S L et al., *J. Biol. Chem.* 278:45969-45977, 2003; Harris S E et al., *Mol Cell Different* 3:137-155, 1995)[33,34] was present in the primary cultures in agreement with this possibility (FIG. 5B,C), but their levels were not induced by high phosphorus conditions. Likewise, RUNX2/Cbfa1, the osteoblast tissue specific transcription factor, (Ducy 1997; Komori T et al., *Cell* 89:755-764, 1997)[17,35] was expressed in the untreated hVSMC cells (FIG. 5D) and not stimulated by media phosphorus. However, the second osteoblast tissue specific transcription factor downstream of BMP-2 and BMP-4, osterix,[24,25] was expressed at low levels until it was induced by high phosphorus culture media (FIG. 5E). RUNX2 and osterix are osteoblastic transcription factors (Nakashima 2002; Lee 2003; Komori 1997)[24,25,35] capable of guiding mesenchymal lineage cells through the osteoblastic program directed by the osteoblastic morphogens BMP-2 and 4. (Harris 1995)[34] BMP-7 failed to affect expression of the BMP-2 pathway upstream of osterix (BMP-2 and RUNX2) (FIG. 5B,C,D), but it strongly inhibited osterix expression (FIG. 5E), and expression of proteins that are markers of the osteoblastic phenotype (FIG. 5A).

Example 19

Figure 6:
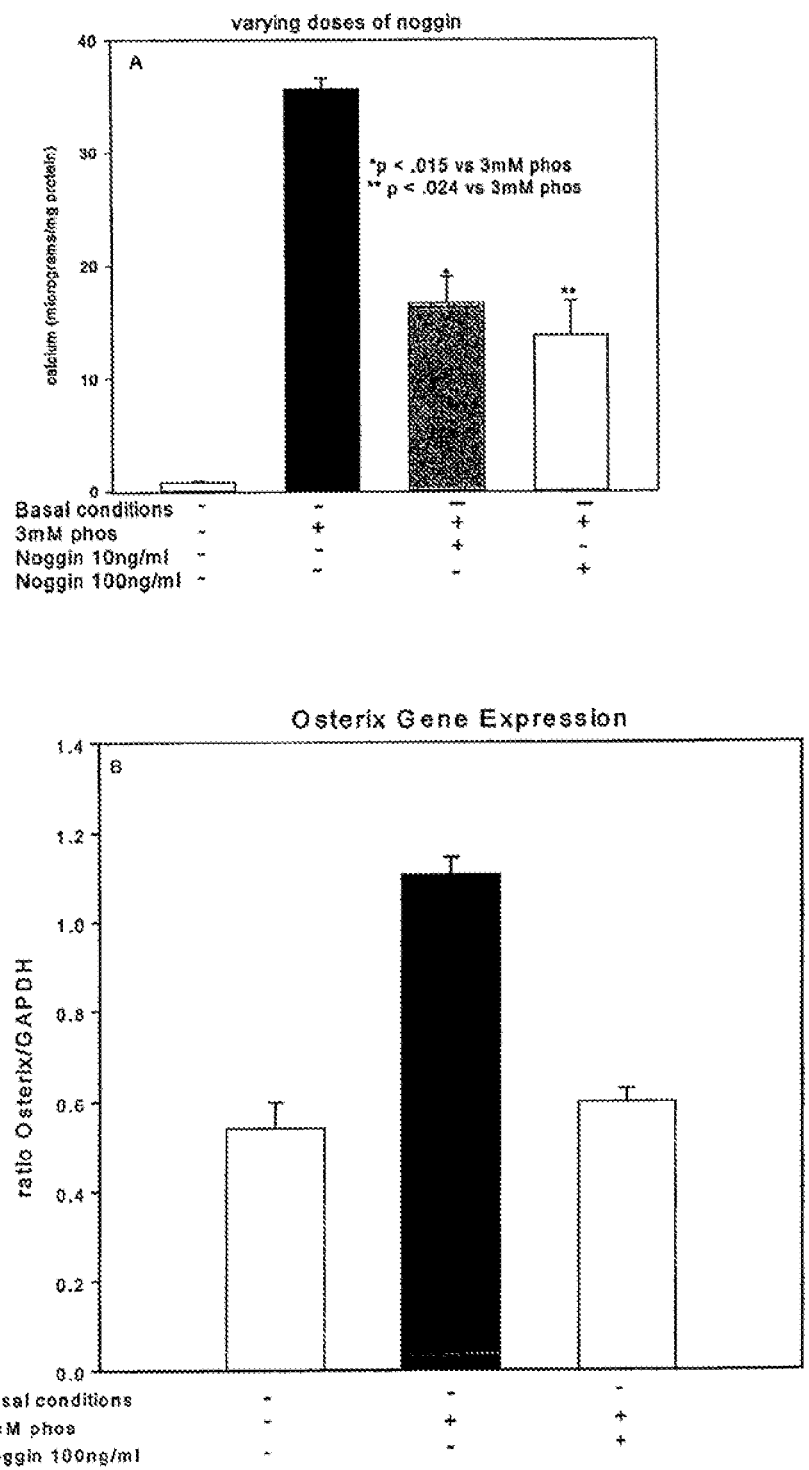
FIG. 6 shows the effects of a bone morphogenetic protein specific inhibitor Noggin, on VSMC mineralization and gene expression.

Inhibition of mineralization by BMP-2 inhibitor. The critical role of BMP-2 in inducing osteoblastic differentiation and mineralization was demonstrated by the elimination of mineralization in high phosphorus media when an inhibitor of BMP-2, noggin, was added (FIG. 6A). Panel A shows the effect of Noggin, (10-100 ng/ml), added to high phosphorus media, shaded bars, inhibited matrix mineralization stimulated by phosphorus. Panel B shows Noggin, 100 ng/ml, blocked phosphorus induced osterix expression. Addition of noggin (FIG. 6B), also inhibited high phosphorus media stimulated osterix expression suggesting that the actions of high phosphorus are cooperative with the BMP-2 and 4 stimulated osteoblastic differentiation. The stimulation of the developmental late-stage second osteoblast specific transcription factor, osterix, by high phosphate was the final step in osteoblastic differentiation that resulted in mineral deposition in the extracellular matrix as shown by reversal of mineralization when osterix was inhibited by BMP-7 treatment (FIG. 6B, FIG. 1).

Example 20

Figure 7:
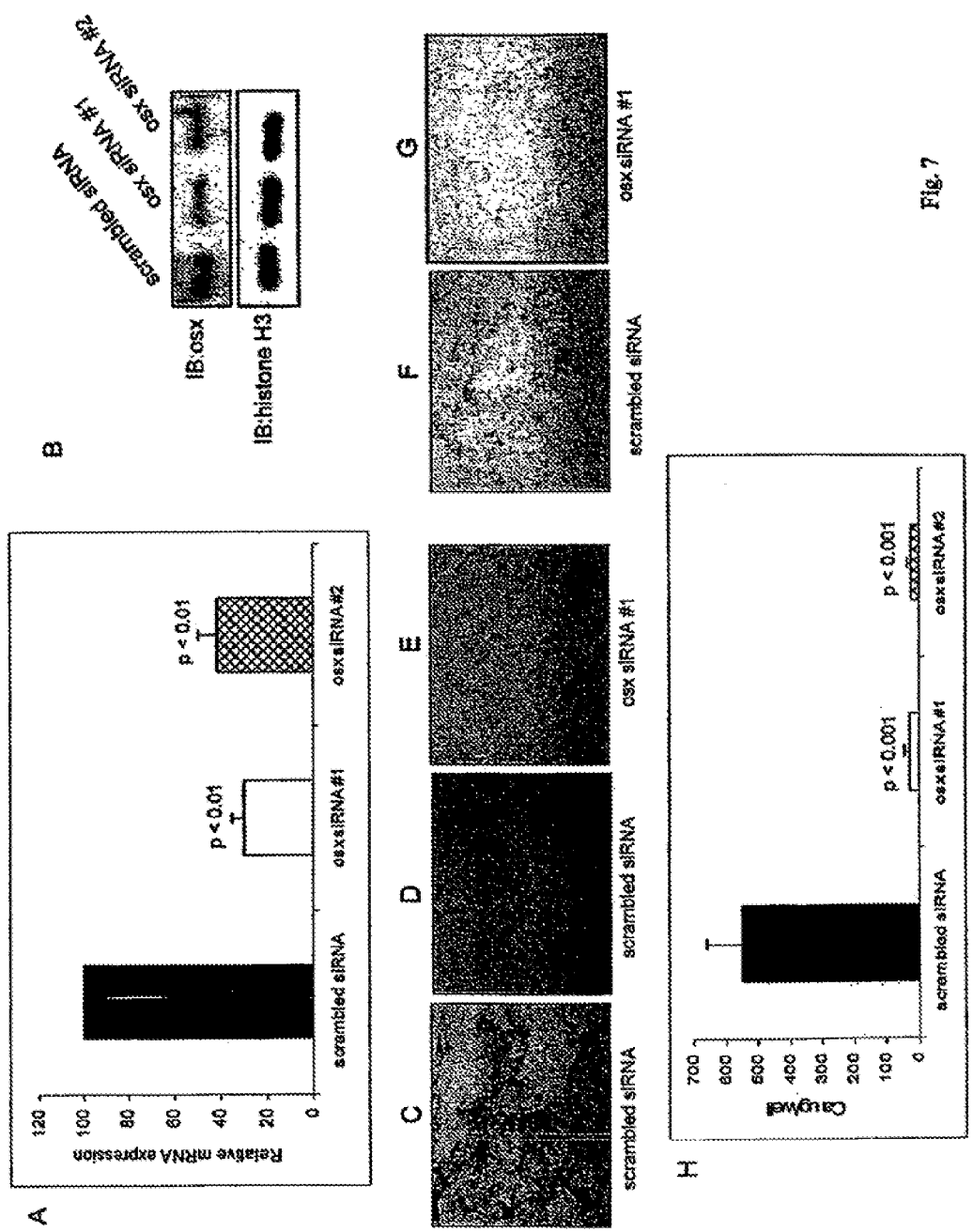
FIG. 7 shows the effects of osterix knockdown on phosphorus stimulated mineralization by osteoblastic-like cells. SAOS cell lines expressing siRNA to osterix were developed as described in the Example 11. Panel A. The levels of mRNA to osterix were decreased by greater than 50% in two separate cell lines (osxsiRNA#1 and osxsiRNA#2). Panel B. Protein levels of osterix were greatly diminished by Western analysis in osxsiRNA #1 and osxsiRNA#2. Histone H3 levels were determined as a loading control on the Western blots. Panels C-G. Von Kossa (Panels C-E) and alizarin red (Panels F, G) stains of cultures stimulated by high phosphorus conditions. Panel C. Mineralized nodules in the periphery of wells containing cells expressing the scrambled siRNA at seven days in the high phosphorus mineralizing conditions. Panel D. Mineralized nodules in the center of wells containing cells expressing the scrambled siRNA at seven days in the high phosphorus mineralizing conditions. Panel E. Absence of mineralization detected by von Kossa staining in periphery of wells expressing osxsiRNA#1 at seven days in the high phosphorus mineralizing conditions. Panel F. Alizarin red stained nodules in the periphery of wells containing cells expressing the scrambled siRNA at seven days in the high phosphorus mineralizing conditions. Panel G. Absence of mineralization detected by alizarin red staining in periphery of wells expressing osxsiRNA#1 at seven days in the high phosphorus mineralizing conditions. The orange is the background stain in alizarin red negative stains. Panel H. Calcium levels in the matrices of cultures of cell lines expressing siRNA to osterix.

Mineralization in osterix knockdown cells. In a phosphate responsive mineralizing cell line, SAOS, retroviral induced expression of osterix siRNA, as described in Example 11, blocked high media phosphate stimulated matrix mineralization as expected while retroviral induced scrambled siRNA from the osterix sequence responded to the high phosphate HL-1 media (FIG. 7).

Example 21

Figure 8:
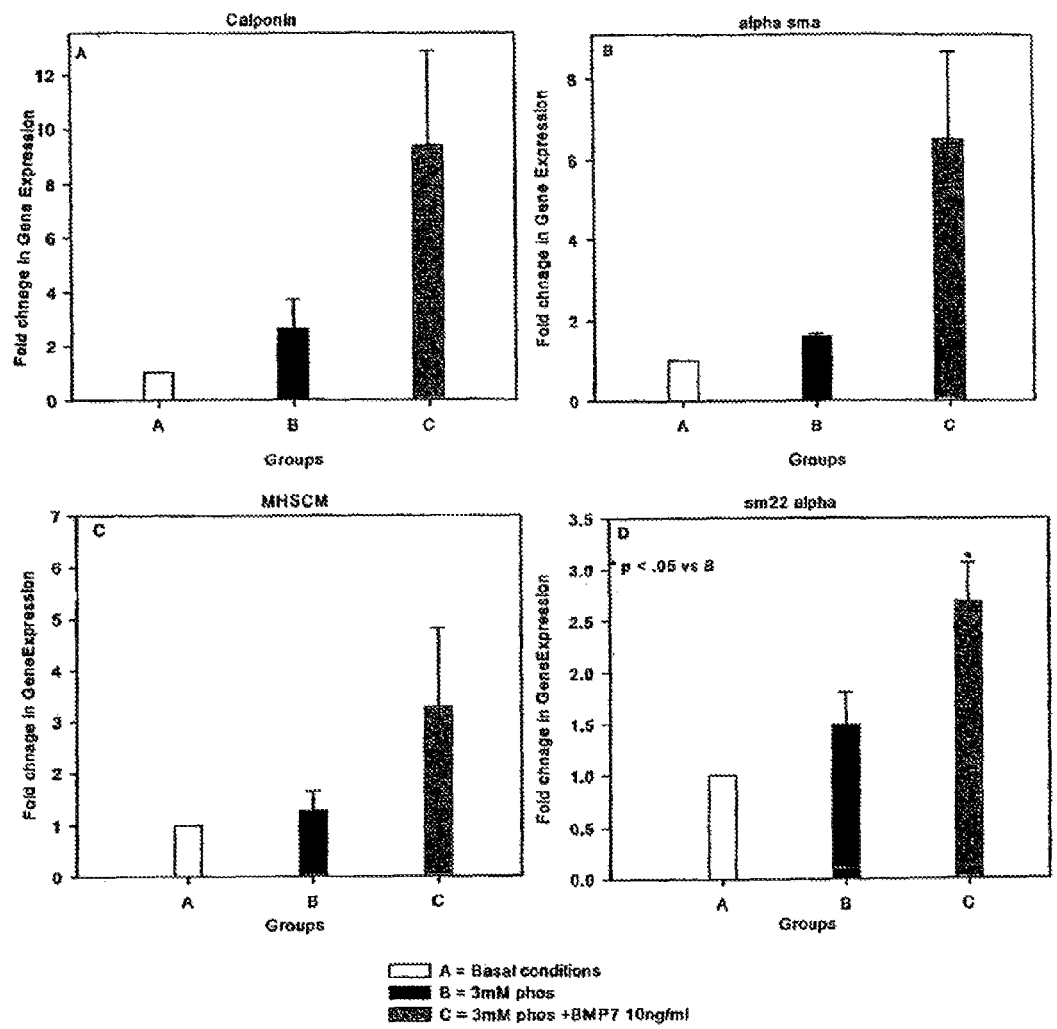
FIG. 8 shows the expression of contractile VSMC markers in hVSMC.

Expression of contractile VSMC markers in human cells. While BMP-7 exhibited actions besides inhibition of osterix, such as stimulating the hVSMC contractile phenotype, phosphorus did not affect transcription of these biomarkers (FIG. 8), so they were not likely to be the mechanism of BMP-7 inhibition of phosphorus action. Expression of VSMC biomarkers as shown in FIG. 8 was reduced in these cultures derived from atherosclerotic aortas, possibly reflecting the abnormal phenotype of VSMC in the neointima associated with atherosclerotic plaques. Calponin (Panel A), alpha smooth muscle actin (alpha SMA) (Panel B), heavy chain myosin (MHSCM) (Panel C), and SM22 alpha (Panel D) message levels detected by RT-PCR were low in hVSMC in basal conditions (open bars, Group A) and in the presence of high phosphorus media (black bars, Group B). BMP-7 (shaded bars, Group C) induced expression of each of the marker proteins. The data in Panels A-D were normalized to the expression level in basal culture conditions and expressed as fold induction, mean±SEM, n=3. The low basal levels may have been the basis for the absence of a high media phosphorus effect to reduce their expression as shown by other investigators (Jono 2000; Li, X et al., 2007, Unpublished Work)[11,36]. SAOS cell lines expressing siRNA to osterix were developed as described in Example 11. Panel A. The levels of mRNA to osterix were decreased by greater than 50% in two separate cell lines (osxsiRNA#1 and osxsiRNA#2). Panel B. Protein levels of osterix were greatly diminished by Western analysis in osxsiRNA #1 and osxsiRNA#2. Histone H3 levels were determined as a loading control on the Western blots. Von Kossa (Panels C-E) and alizarin red (Panels F, G) stains of cultures stimulated by high phosphorus conditions. Panel C. Mineralized nodules in the periphery of wells containing cells expressing the scrambled siRNA at seven days in the high phosphorus mineralizing conditions. Panel D. Mineralized nodules in the center of wells containing cells expressing the scrambled siRNA at seven days in the high phosphorus mineralizing conditions. Panel E. Absence of mineralization detected by von Kossa staining in periphery of wells expressing osxsiRNA#1 at seven days in the high phosphorus mineralizing conditions. Panel F. Alizarin red stained nodules in the periphery of wells containing cells expressing the scrambled siRNA at seven days in the high phosphorus mineralizing conditions. Panel G. Absence of mineralization detected by alizarin red staining in periphery of wells expressing osxsiRNA#1 at seven days in the high phosphorus mineralizing conditions. The orange is the background stain in alizarin red negative stains. Panel H. Calcium levels in the matrices of cultures of cell lines expressing siRNA to osterix.

The BMP-2/4-directed program is antagonized by BMP-7, a closely-related BMP that is generally, but not always, (Asahina I. et al., *Exp Cell Res* 222:38-47, 1996)[37] complementary in osteoblast function. This is consistent with observed phenomena in several biological situations including kidney development where BMP-2 inhibits BMP-7-stimulated branching morphogenesis. (Piscione T. D. et al., *Am J Phys (Renal)* 273:F961-F975, 1997)[38] A consistent phenomenon had been reported, in collecting duct function where BMP-2 inhibited proliferation and induced apoptosis, while low dose BMP-7 stimulated proliferation. (Piscione T. D. et al., *Am J Physiol Renal Physiol* 280:F19-F33, 2001)[39] Without being bound by theory, such distinct activities of related BMPs are possibly due to utilization of different receptors (Macias-Silva M. et al., *J Biol Chem* 273:25628-25636, 1998)[40] and Smad independent signal transduction.

Example 22

Figure 9:
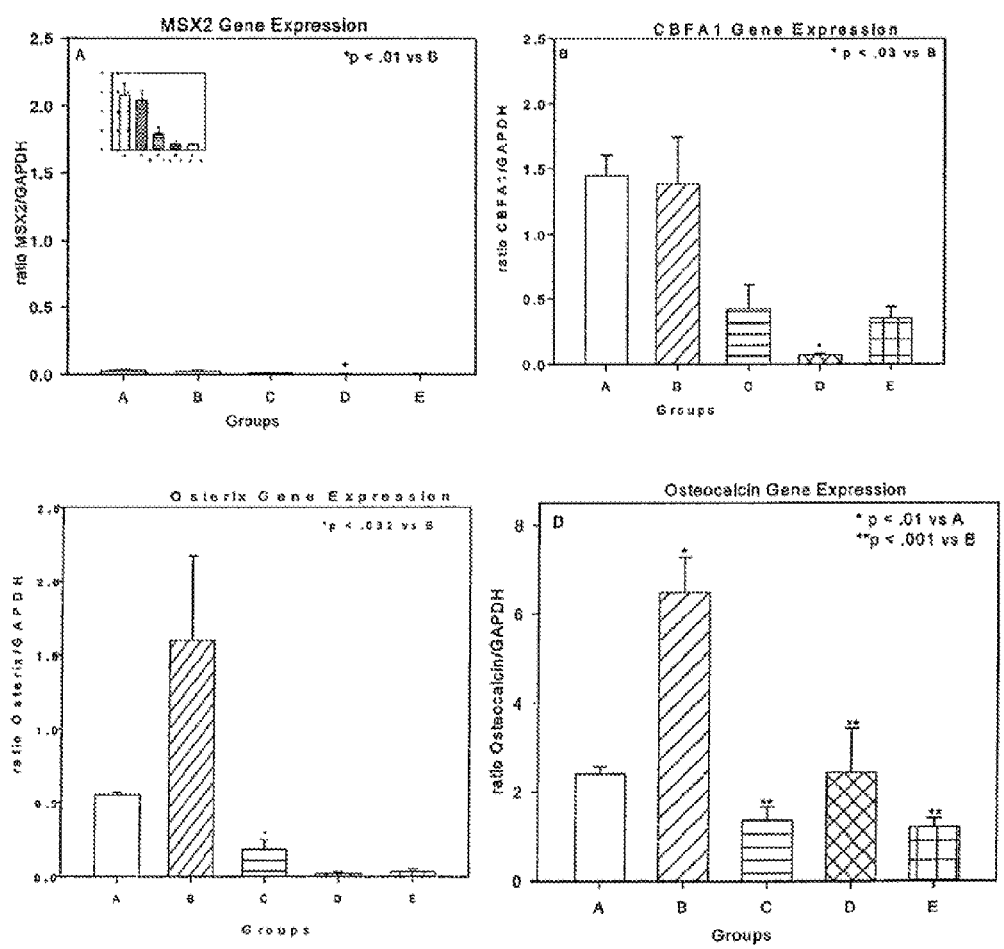
FIG. 9 shows expression of various calcification related genes in aortas of various groups of LDLR–/– high fat fed mice measured by real time RT-PCR.

Expression of calcification related genes. To relate the mechanism of phosphorus action detected in vitro to this model of CKD induced vascular calcification and hyperphosphatemia in vivo, the inventors of the instant invention analyzed aortic expression of the osteoblastic lineage genes including osterix message levels by real time RT-PCR. The various groups of mice were: A, sham operated; B, CKD vehicle treated; C, CKD BMP-7 treated; D, CKD 3% $CaCO_3$ treated; E, CKD 3% $LaCO_3$ treated. MSX2 expression (A) was low, not induced by CKD and suppressed with each of the three treatments. Inset shows data for scale of the ratio between 0.0-0.5. CBFA1 expression (B) was not stimulated by CKD, but it was inhibited by BMP-7, 3% $CaCO_3$, and 3% $LaCO_3$, treatment. Osterix expression (C) was stimulated by CKD and it was inhibited by BMP-7, $CaCO_3$, or $LaCO_3$ treatment. Osteocalcin expression (D) was strongly induced by CKD (note different Y axis scale), and inhibited by BMP-7, $CaCO_3$ or $LaCO_3$. The number of aortas/animals in each group was 4. Data are expressed as the mean of the transcript levels relative to GAPDH expression in each aorta±SEM, N=3. In the high fat fed sham operated mice, the inventors of the instant invention found expression of BMP-2 (not shown), MSX2 (FIG. 9A), and RUNX2 (FIG. 9B) in agreement with recent data from Shao et al. 2005,[27] but osterix was only weakly expressed (FIG. 9C). Osterix was strongly induced by CKD (FIG. 9C), and treatment with BMP-7, or CaCO$_3$, shown above (FIGS. 1 and 2) to partially reverse vascular calcification, reduced osterix and RUNX2 expression (FIGS. 9B & C). Aortic expression of osteocalcin was diminished by BMP-7, CaCO$_3$, or LaCO$_3$ therapy (FIG. 9D) compatible with inhibition of osterix activity and the osteoblastic transcriptional program. (Hoffman 1994;Ducy P. et al., *Mol Cell Biol* 15:1858-1869, 1995)[32;41]

The invention disclosed herein extend previous studies demonstrating that CKD stimulates vascular mineralization. (Davies 2003; Davies 2005; Phan O. et al., *Circulation* 112: 2875-2882, 2005; Tamagaki K. et al., *Nephrol Dial Transplant* 21:651-659, 2006)[19;20;42;43] The described animal model, the low density lipoprotein receptor deficient mouse fed a high fat diet, is an animal model of atherosclerosis due to hyperlipidemia, obesity, insulin resistance, and the metabolic syndrome. In this animal model, VC develops in aortic atherosclerotic neointima (Davies 1003; Shao 2006)[19;26] associated with expression of an osteoblastic differentiation program directed by BMP-2 and MSX2 along with the transcriptional effects of the osteoblast transcription factor RUNX2. (Shao 2005)[27;33] The data obtained demonstrate that MSX2 is expressed in low levels in the fat fed atherosclerotic aorta in agreement with Cheng et al, (2003)[33] who proceeded to overexpress MSX2 to demonstrate its role in osteoblastic vascular calcification. Shao et al, (Shao, J. S. et al. *J. Clin. Invest.* 115:1210-1220, 2005)[27] also demonstrate activation of adventitial Wnt activity in the LDLR−/− fat fed model, but the inventors of the instant invention have shown CKD induced perivascular Wnt inhibitors, (Surendran K. et al., *J. Am. Soc. Neph.* 16:2373-2384, 2005)[44] and the role of Wnt activity in CKD induced VC requires further study. The present studies and the previous studies by the inventors and the colleagues demonstrate major intensification of the neointimal calcification induced by CKD in this model. (Davies 2003; Davies 2005)[19;20] The results are also in agreement with previous study by the inventors and their colleagues in that the induction of CKD was associated with the development of hyperphosphatemia, and that treatment with BMP-7 corrected hyperphosphatemia. (Davies 2005)[20] The effect of BMP-7 to correct hyperphosphatemia has been shown to be due to stimulation of bone formation, (Davies 2005)[20] and correction of hyperphosphatemia has been preventive in the development of CKD stimulated VC. (Davies 2005; Mathew 2007)[20;30]

An unexpected and new invention herein is the demonstration that established vascular mineralization levels can be diminished by BMP-7 and hyperphosphatemia control. Reduction of existing vascular mineral deposits with pharmacologic treatment is a significant step forward in atherosclerosis therapy. It makes a strong case for the mechanism of the atherosclerotic mineralization process to be an active biologic remodeling mechanism. One such mechanism would be akin to skeletal remodeling where mineral deposition (bone formation) is linked to mineral resorption. Resorption of existing deposits at a rate greater than formation adding to or creating new deposits is the most reasonable explanation of these results. Since TRAP positive multinucleated osteoclast-like cells have been demonstrated in the neointima, (Moe 2002; Chen N. X. et al., *Sem. Nephrol.* 24:61-68, 2004; Doherty T. M. et al. *FASEB J.* 16:577-582, 2002)[14;45;46] the inventors of the instant invention interpreted the decrease in the vascular mineralization in CaCO$_3$ and BMP-7 treated animals to be compatible with decreased formation of vascular mineral deposits and continued resorption.

Reduction of CKD induced vascular calcification in the described animal model with control of the hyperphosphatemia is evidence for reversal of a phosphorus stimulated effect. In the studies in vitro, phosphorus stimulated mineralization through activation of a BMP-2 directed vascular osteoblastic program through the actions of osteoblast specific transcription factors. The osteoblastic program was present in these cell cultures demonstrated by the presence of BMP-2 and MSX2 expression, the presence of RUNX2, and the targets of RUNX2 transcriptional activity such as osteocalcin. (Ducy 1997; Ducy 1995)17;41 The finding of BMP-2 and 4 and RUNX2 expression in hVSMC derived from atherosclerotic aortas differs from the results of primary cultures of normal aortas without atherosclerosis. However, mineralization was not present due to insufficient expression of osterix, a critical osteoblastic tissue specific transcription factor, (Nakashima 2002; Koga T. et al., *Nature Medicine* 11:880-885, 2005)[24;47] which was stimulated by the addition of media phosphorus and is downstream of BMP-2 but not necessarily RUNX2. (Lee 2003)[25] That high media phosphorus induced mineralization was indeed due to activity of the osteogenic program was demonstrated by its inhibition with a BMP antagonist, noggin. Interruption of the program through inhibition of the transcription factor, osterix, as with BMP-7 treatment or by siRNA to osterix, was sufficient in the presence of high media phosphorus to eliminate mineralization. Thus, phosphorus was an active signaling molecule leading to increased osterix expression and not just a physical-chemical mineralization force in agreement with other studies in vitro. (Steiz 2001; Jono 2000; Li 2006)[10;11;22] These studies (Jono 2000; Li 2006)[11;22] have established that the action of phosphorus is related to the activity of the Pit1 sodium dependent transporter in VSMC as suggested in osteoblasts. (Beck G. R. et al., *Proc Natl Acad Sci* 97:8352-8357, 2000)[48] Its role as a signal molecule may be through Pit1 induced activation of a membrane associated signaling complex similar to that known to associate with the sodium dependent transport protein of the proximal tubule and osteoclasts, NaPi2a. (Biber J. et al., *Am. J. Physiol. Renal. Physiol.* 287:871-5, 2004)[49]

The described data in vivo were directly related to in vitro models. In agreement with previous studies, (Shao 2005)[27] the BMP-2/MSX2 program was induced in the aorta by high fat feeding analogous to the basal condition hVSMC cultures from atherosclerotic donors. However, CKD was the major stimulus to VC in this model analogous to the effect of phosphorus in vitro. CKD induced expression of osterix in the aorta, similar to the effect of phosphorus in vitro. Control of hyperphosphatemia by two separate therapeutic strategies reversed VC and returned aortic osterix and RUNX2 expression to levels below that in aortas of sham operated high fat fed mice. Thus, the data herein demonstrate activation of an osteoblastic program in the vasculature as the pathogenesis of CKD stimulated atherosclerotic calcification in agreement with data from other investigators. (Reynolds 2004; Moe 2003)[12;18]

Regarding the role of phosphorus, translational data are in agreement with human clinical observations of Chertow et al. (Chertow G. M. et al., *Kidney Int* 62:245-252, 2002)[50] and Block (Block G. A. et al., *Kidney Int* 68:1815-1824, 2005)[51] in vivo, and several labs in vitro. (Tyson 2003; Steitz 2001; Jono 2000)[9-11] This specification describe for the first time to clearly demonstrate that phosphorus causes VC in vivo, and that the mechanism of phosphorus action is through stimulation of a heterotopic osteoblastic differentiation program. These data are in agreement with the human epidemiologic studies relating hyperphosphatemia to cardiovascular mortality in CKD, (Kestenbaum 2006; Slinin 2005)[3;4] and they offer a mechanism of hyperphosphatemia action. The studies reported here provide a mechanism of hyperphosphatemia induced atherosclerotic vascular calcification in CKD. They may not be related to the calcification of the elastic lamina of the arterial media that is also stimulated in CKD. This process is distinct from osteoblastic mineralization where the matrix mineralization substrate is type 1 collagen.

Example 23

Effect of BMP-7 Treatment on the Effect of CKD on Neointimal Hyperplasia

A. Creation of Arteriovenous (AV) Fistulae

Figure 11:
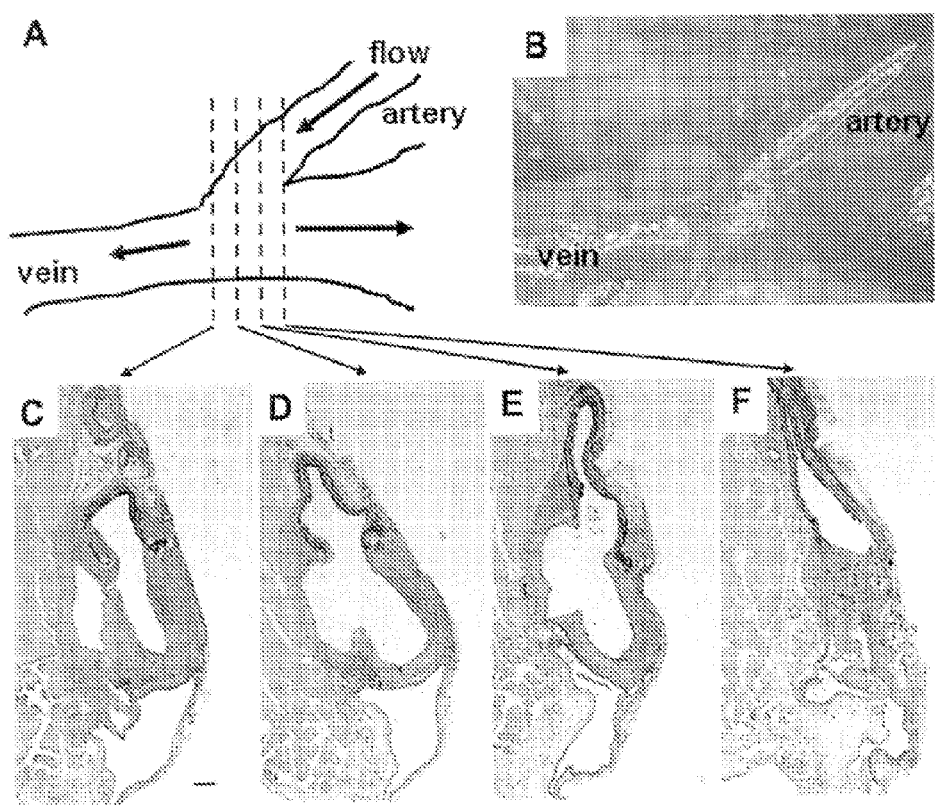
FIG. 11 is a schematic representation of the AV anastomosis. Actual picture (B) and schema (A) of mouse model of AV fistula creation with end-to-side anastomosis of end left common carotid artery to side left external jugular vein. One-hundred micron cross-sections of the venous anastomosis 3 weeks following AV fistula creation (C-F). Bar=100 µm.

Six weeks after creation of CKD and sham mice as described above, animals underwent an AV fistula creation by anastomosing the left common carotid artery to the jugular vein in an end-to-side fashion. Under a sterile condition, a vertical incision was made in the left neck with the left common carotid artery and the adjacent external jugular vein carefully dissected out. The common carotid artery clamp was placed at the proximal portion with an 11-0 nylon suture and the common carotid artery was divided just proximal to the bifurcation. Next, the jugular vein was clamped proximally and distally and punctured in the middle portion with a 27 G syringe. After filling this vein segment with heparinized saline, the venotomy of 0.7 mm in length was performed. The end to side anastomosis (common carotid artery end to jugular vein side) were then created using 11-0 nylon heel to toe continuous suturing. The vessels were unclamped and checked for patency (FIG. 11A, B).

Three weeks after AV fistula creation, animals were euthanized, and the AV anastomoses were perfusion-fixed via the left ventricle at 100 mm Hg pressure as described previously (Leidenfrost J E, et al., *Am J Pathol.* 2003; 163(2):773-778).[53] Before perfusion fixation, blood was drawn from the left ventricle for the biochemical analysis. Blood urea nitrogen (BUN), phosphorus, and calcium were measured by autoanalyzer techniques in the Animal Facility Clinical Laboratory at Washington University in St. Louis, Mo.

B. Effect of BMP Treatment on CKD Induced NH Lesions

Figure 12:
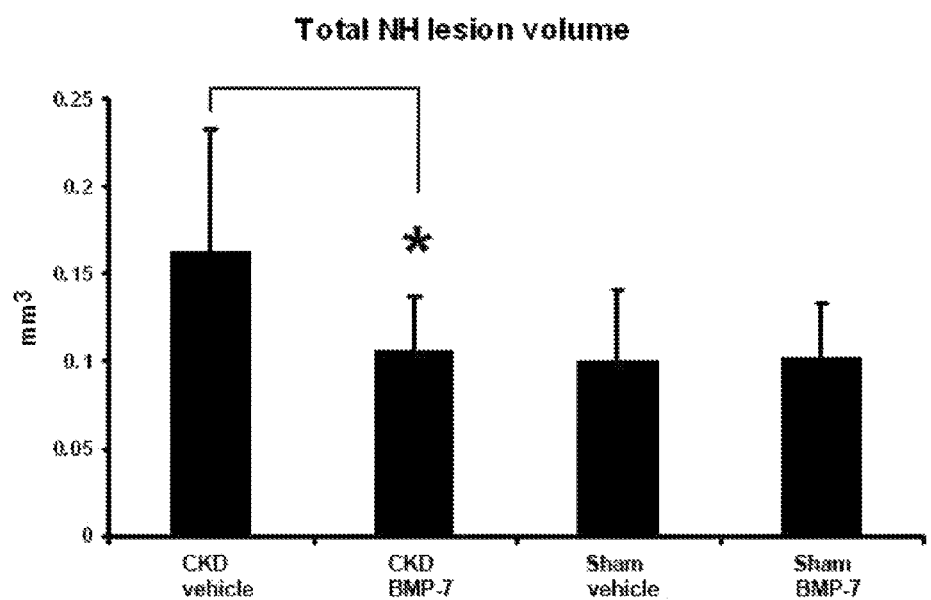
FIG. 12 shows the effect of BMP-7 administration on CKD induction of anastomotic NH lesion formation.

To study the possibility that CKD induced VSMC dedifferentiation allowing higher rates of migration, the effects of a systemically administered VSMC differentiation factor (e.g., BMP-7 which has been previously shown to stimulate expression of markers of the VSCM contractile phenotype in vitro (Mathew, S, et al., *J Am Soc Nephrol.*, 2005 16:52a (Abstract))[62] on neointimal hyperplasia (NH) lesion development was examined. Mice underwent CKD creation and 3 weeks later underwent arteriovenous (AV) fistula creation. One week prior to the AV fistula creation and continuing through to AV anastomosis harvest, BMP-7 (100 µg/kg) or its vehicle (saline) was administered intraperitoneally twice a week. In sham operated animals, there was no effect of BMP-7 on NH lesion development (18 BMP-7 animals vs. 16 vehicle animals). However, BMP-7 administration eliminated the stimulation of NH lesion formation induced by CKD (16 BMP-7 animals vs. 19 vehicle animals). *$P<0.01$. FIG. 12. These results suggest that the CKD stimulated VSMC migration to the NH lesion was allowed through effects of CKD to diminish the VSCM differentiation of the migrating cells.

References

1. Go A S, Chertow G M, Fan D, McCulloch C E, Hsu Cy: Chronic kidney disease and the risks of death, cardiovascular events, and hospitalization. *New Engl J Med* 351:1296-1305, 2004.
2. Berl T, Henrich W: Kidney-heart interactions: epidemiology, pathogenesis, and treatment. *Clin J Am Soc Nephrol* 1:8-18, 2006.
3. Kestenbaum B, Sampson J N, Rudser K D, Patterson D J, Seliger S L, Young B, Sherrard D J, Andress D L: Serum phosphate levels and mortality risk among people with chronic kidney disease. *J Am Soc Nephrol* 16:520-528, 2005.
4. Slinin Y, Foley R N, Collins A J: Calcium, Phosphorus, Parathyroid Hormone, and Cardiovascular Disease in Hemodialysis Patients: The USRDS Waves 1, 3, and 4 Study. *J Am Soc Nephrol* 16:1788-1793, 2005.
5. London G M, Guerin A P, Marchais S J, Metivier F, Pannier B, Adda H: Arterial media calcification in end-stage renal diseases: impact on all-cause and cardiovascular mortality. *Nephrol Dial Transplant* 18:1731-1740, 2003.
6. Raggi P, Boulay A, Chasan-Taber S, Amin N, Dillon M, Burke S K, Chertow G M: Cardiac calcification in adult hemodialysis patients. A link between end-stage renal disease and cardiovascular disease? *J Am Coll Cardiol* 39:695-701, 2002.
7. Zile M R, Baicu C F, Gaasch W H: Diastolic heart failure—abnormalities in active relaxation and passive stiffness of the left ventricle. *N Eng J Med* 350:1953-1959, 2004.
8. Ohtake T, Kobayashi S, Moriya H, Negishi K, Okamoto K, Maesato K, Saito S: High Prevalence of Occult Coronary Artery Stenosis in Patients with Chronic Kidney Disease at the Initiation of Renal Replacement Therapy: An Angiographic Examination. *J Am Soc Nephrol* 16:1141-1148, 2005.
9. Tyson K L, Reynolds J L, McNair R, Zhang Q, Weissberg P L, Shanahan C M: Osteo/chondrocytic transcription factors and their target genes exhibit distinct patterns of expression in human arterial calcification. *Arterioscler Thromb Vasc Biol* 23:489-494, 2003.
10. Steitz S A, Speer M Y, Curinga G, Yang H-Y, Haynes P, Aebersold R., Schinke T, Karsenty G, Giachelli C M: Smooth muscle cell phenotypic transition associated with calcification. *Circ Res* 89:1147-1154, 2001.
11. Jono S, McKee M D, Murry C E, Shioi A, Nishizawa Y, Mori K, Morii H, Giachelli C M: Phosphate regulation of vascular smooth muscle cell calcification. *Circ Res* 87:e10-e17, 2000.
12. Reynolds J L, Joannides A J, Skepper J N, McNair R, Schurgers L J, Proudfoot D, Jahnen-Dechent W, Weissberg P L, Shanahan C M: Human Vascular Smooth Muscle Cells Undergo Vesicle-Mediated Calcification in Response to Changes in Extracellular Calcium and Phosphate Concentrations: A Potential Mechanism for Accelerated Vascular Calcification in ESRD. *J Am Soc Nephrol* 15:2857-2867, 2004.
13. Trion A, van der Laarse A: Vascular smooth muscle cells and calcification in atherosclerosis. *Am Heart J* 147:808-814, 2004.
14. Moe S M, O'Neill K D, Duan D, Ahmed S, Chen N X, Leapman S B, Fineberg N, Kopecky K: Medial artery calcification in ESRD patients is associated with deposition of bone matrix proteins. *Kidney International* 61:638-647, 2002.
15. Boström K, Watson K E, Horn S, Worthman C, Herman I M, Demer L L: Bone morphogenetic protein expression in human atherosclerotic lesions. *J Clin Invest* 91:1800-1809, 1993.
16. Dhore C R, Cleutjens J, Lutgens E, Cleutjens K, Geussens P, Kitslaar P, Tordoir J, Spronk H, Vermeer C, Daemen M: Differential expression of bone matrix regulatory proteins in human atherosclerotic plaques. *Arterioscler Thromb Vasc Biol* 21:1998-2003, 2001.
17. Ducy P, Zhang R, Geoffroy V, Ridall A L, Karsenty G: Osf2/Cbfa1: A transcriptional activator of osteoblast differentiation. *Cell* 89:747-754, 1997.
18. Moe S M, Duan D, Doehle B P, O'Neill K D, Chen N X: Uremia induces the osteoblast differentiation factor Cbfa1 in human blood vessels. *Kidney Int* 63:1003-1011, 2003.
19. Davies M R, Lund R J, Hruska K A: BMP-7 is an efficacious treatment of vascular calcification in a murine model of atherosclerosis and chronic renal failure. *J Am Soc Neph* 14:1559-1567, 2003.
20. Davies M R, Lund R J, Mathew S, Hruska K A: Low turnover osteodystrophy and vascular calcification are amenable to skeletal anabolism in an animal model of chronic kidney disease and the metabolic syndrome. *J Am Soc Neph* 16:917-928, 2005.
21. Lund R J, Davies M R, Brown A J, Hruska K A: Successful treatment of an adynamic bone disorder with bone morphogenetic protein-7 in a renal ablation model. *J Am Soc Neph* 15:359-369, 2004.
22. Li X, Yang H Y, Giachelli C M: Role of the Sodium-Dependent Phosphate Cotransporter, Pit-1, in Vascular Smooth Muscle Cell Calcification. *Circ Res* 98:905-912, 2006.
23. Lecanda F, Avioli L V, Cheng S L: Regulation of bone matrix protein expression and induction of differentiation of human osteoblasts and human bone marrow stromal cells by bone morphogenetic protein-2. *J Cell Biochem* 67:386-398, 1997.
24. Nakashima K, Zhou X, Kunkel G, Zhang Z, Deng J M, Behringer R R, De Crombrugghe B: The novel zinc finger-containing transcription factor osterix is required for osteoblast differentiation and bone formation. *Cell* 108:17-29, 2002.
25. Lee M-H, Kwon T-G, Park H-S, Wozney J M, Ryoo H-M: BMP-2 induced osterix expression is mediated by Dlx5 but is independent of Runx2. *Biochem Biophys Res Com* 309:689-694, 2003.
26. Towler D A, Bidder M, Latifi T, Coleman T, Semenkovich C F: Diet-induced diabetes activates an osteogenic gene regulatory program in the aortas of low density lipoprotein receptor-deficient mice. *J Biol Chem* 273: 30427-30434, 1998.
27. Shao J S, Cheng S L, Pingsterhaus J M, Charlton-Kachigian N, Loewy A P, Towler D A: Msx2 promotes cardiovascular calcification by activating paracrine Wnt signals. *J Clin Invest* 115:1210-1220, 2005.
28. Dorai H, Vukicevic S, Sampath T K: Bone morphogenetic protein-7 (osteogenic protein-1) inhibits smooth muscle cell proliferation and stimulates the expression of markers that are characteristic of SMC phenotype in vitro. *J Cellular Physiol* 184:37-45, 2000.
29. Dorai H, Sampath T K: Bone Morphogenetic Protein-7 Modulates Genes that Maintain the Vascular Smooth Muscle Cell Phenotype in Culture. *J Bone and Joint Surg* 83:S70-S78, 2001.
30. Mathew S, Lund R, Strebeck F, Tustison K S, Geurs T, Hruska K A: Reversal of the adynamic bone disorder and decreased vascular calcification in chronic kidney disease by sevelamer carbonate therapy. *J Am Soc Nephrol* 18:122-130, 2007.
31. Aubin J E, Liu F: The osteoblast lineage. In: Principles of Bone Biology, edited by Bilezikian J P, Raisz L G, Rodan G A, New York, Academic Press, 1996, pp 51-67.
32. Hoffmann H M, Catron K M, van Wijnen A J, McCabe L R, Lian J B, Stein G S, Stein J L: Transcriptional control of the tissue-specific, developmentally regulated osteocalcin gene requires a binding motif for the Msx family of homeodomain proteins. *Proceedings of the National Academy of Sciences, USA* 91:12887-12891, 1994.
33. Cheng S L, Shao J S, Charlton-Kachigian N, Loewy A P, Towler D A: Msx2 Promotes Osteogenesis and Suppresses Adipogenic Differentiation of Multipotent Mesenchymal Progenitors. *J Biol Chem* 278:45969-45977, 2003
34. Harris S E, Feng J Q, Harris M A, Ghosh-Choudhury N, Wozney J, Mundy G R: Recombinant bone morphogenetic protein 2 accelerates the bone cell differentiation program and auto-regulates BMP 2 expression and BMP 2 promoter activity in fetal rat calvariae osteoblast cultures. *Mol Cell Different* 3:137-155, 1995.
35. Komori T, Yagi H, Nomura S, Yamaguchi A, Sasaki K, Deguchi K, Shimizu Y, Bronson R T, Gao Y-H, Inada M: Targeted Disruption of Cbfa1 Results in a Complete Lack of Bone Formation owing to Maturational Arrest of Osteoblasts. *Cell* 89:755-764, 1997.
36. Li, X., Yang, H-Y., and Giachelli, C. BMP-2 promotes phosphate uptake, phenotypic modulation, and calcification of vascular smooth muscle cells. 2007.
Ref Type: Unpublished Work.
37. Asahina I, Sampath T K, Hauschka P V: Human osteogenic protein-1 induces chondroblastic, osteoblastic, and/or adipocytic differentiation of clonal murine target cells. *Exp Cell Res* 222:38-47, 1996.
38. Piscione T D, Yager T D, Gupta I R, Grinfeld B, Pei Y, Attisano L, Wrana J L, Rosenblum N D: BMP-2 and OP-1 exert direct and opposite effects on renal branching morphogenesis. *Am J Phys (Renal)* 273:F961-F975, 1997.
39. Piscione T D, Phan T, Rosenblum N D: BMP7 controls collecting tubule cell proliferation and apoptosis via Smad1-dependent and -independent pathways. *Am J Physiol Renal Physiol* 280:F19-F33, 2001.
40. Macias-Silva M, Hoodless P A, Tang S J, Buchwald M, Wrana J L: Specific Activation of Smad1 Signaling Pathways by the BMP7 Type I Receptor, ALK2. *J Biol Chem* 273:25628-25636, 1998.
41. Ducy P, Karsenty G: Two distinct osteoblast-specific cis acting elements control expression of a mouse osteocalcin gene. *Mol Cell Biol* 15:1858-1869, 1995.
42. Phan O, Ivanovski O, Nguyen-Khoa T, Mothu N, Angulo J, Westenfeld R, Ketteler M, Meert N, Maizel J, Nikolov I G, Vanholder R, Lacour B, Drueke T B, Massy Z A: Sevelamer Prevents Uremia-Enhanced Atherosclerosis Progression in Apolipoprotein E-Deficient Mice. *Circulation* 112:2875-2882, 2005.
43. Tamagaki K, Yuan Q, Ohkawa H, Imazeki I, Moriguchi Y, Imai N, Sasaki S, Takeda K, Fukagawa M: Severe hyperparathyroidism with bone abnormalities and metastatic calcification in rats with adenine-induced uraemia. *Nephrol Dial Transplant* 21:651-659, 2006.
44. Surendran K, Schiavi S, Hruska K A: Wnt-dependent-b-catenin signaling is activated after unilateral ureteral obstruction, and recombinant secreted frizzled-related protein 4 alters the progression of renal fibrosis. *J Am Soc Neph* 16:2373-2384, 2005.
45. Chen N X, Moe S M: Vascular calcification in chronic kidney disease. *Sem Nephrol* 24:61-68, 2004.
46. Doherty T M, Uzui H, Fitzpatrick L A, Tripathi P V, Dunstan C R, Asotra K, Rajavashisth T B: Rationale for 46. the role of osteoclast-like cells in arterial calcification. *FASEB J* 16:577-582, 2002.
47. Koga T, Matsui Y, Asagiri M, Kodama T, De Crombrugghe B, Nakashima K, Takayanagi H: NFAT and Osterix cooperatively regulate bone formation. *Nature Medicine* 11:880-885, 2005.
48. Beck G R, Jr., Zerler B, Moran E: Phosphate is a specific signal for induction of osteopontin gene expression. *Proc Natl Acad Sci* 97:8352-8357, 2000.
49. Biber J, Gisler S M, Hernando N, Wagner C A, Murer H: PDZ interactions and proximal tubular phosphate reabsorption. *Am J Physiol Renal Physiol* 287:871-5, 2004.
50. Chertow G M, Burke S K, Raggi P: Sevelamer attenuates the progression of coronary and aortic calcification in hemodialysis patients. *Kidney Int* 62:245-252, 2002.
51. Block G A, Spiegel D M, Ehrlich J, Mehta R, Lindbergh J, Dreisbach A, Raggi P: Effects of sevelamer and calcium on coronary artery calcification in patients new to hemodialysis. *Kidney Int* 68:1815-1824, 2005.
52. Moe S M, Reslerova M, Ketteler M, O'Neill K, Duan D, Koczman J, Westenfeld R, Jahnen-Dechent W, Chen N X: Role of calcification inhibitors in the pathogenesis of vascular calcification in chronic kidney disease (CKD). *Kidney Int* 67:2295-2304, 2005.
53. Leidenfrost J E, Khan M F, Boc K P, Villa B R, Collins E T, Parks W C, Abendschein D R, Choi E T. A model of primary atherosclerosis and post-angioplasty restenosis in mice. *Am J Pathol.* 2003; 163(2):773-778.
54. Shenoy S, Miller A, Petersen F, Kirsch W M, Konkin T, Kim P, Dickson C, Schild A F, Stewart L, Reyes M, Anton L, Woodward R S. A multicenter study of permanent hemodialysis access patency: beneficial effect of clipped vascular anastomotic technique. *J Vasc Surg.* 2003; 38(2):229-235.
55. Lee H, Manns B, Taub K, Ghali W A, Dean S, Johnson D, Donaldson C. Cost analysis of ongoing care of patients with end-stage renal disease: the impact of dialysis modality and dialysis access. *Am J Kidney Dis.* 2002; 40(3):611-622.
56. Mattana J, Effiong C, Kapasi A, Singhal P C. Leukocyte-polytetrafluoroethylene interaction enhances proliferation of vascular smooth muscle cells via tumor necrosis factor-alpha secretion. *Kidney Int.* 1997; 52(6): 1478-1485.
57. Ezzahiri R, Lemson M S, Kitslaar P J, Leunissen K M, Tordoir J H. Haemodialysis vascular access and fistula surveillance methods in The Netherlands. *Nephrol Dial Transplant.* 1999; 14(9):2110-2115.
58. Cinat M E, Hopkins J, Wilson S E. A prospective evaluation of PTFE graft patency and surveillance techniques in hemodialysis access. *Ann Vasc Surg.* 1999; 13(2):191-198.
59. Tordoir J H, Hofstra L, Leunissen K M, Kitslaar P J. Early experience with stretch polytetrafluoroethylene grafts for haemodialysis access surgery: results of a prospective randomised study. *Eur J Vasc Endovasc Surg.* 1995; 9(3):305-309.
60. Roy-Chaudhury P, Sukhatme V P, Cheung A K. Hemodialysis vascular access dysfunction: a cellular and molecular viewpoint. *J Am Soc Nephrol.* 2006; 17(4): 1112-1127.
61. Nikkari S T, Clowes A W. Restenosis after vascular reconstruction. *Ann Med.* 1994; 26(2):95-100.
62. Mathew, S, Geurs, S and Hruska, K A. Bone morphogenetic protein-7 (BMP-7) inhibits vascular calcification (VC) by stimulating the contractile vascular smooth muscle cell (VSMC) phenotype. *J Am Soc Nephrol.,* 2005 16:52a (Abstract).

SEQUENCE LISTING

```
<160> NUMBER OF SEQ ID NOS: 68

<210> SEQ ID NO 1
<211> LENGTH: 431
<212> TYPE: PRT
<213> ORGANISM: Homo sapiens

<400> SEQUENCE: 1

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Gly Gly
                85                  90                  95

Gly Pro Gly Gly Gln Gly Phe Ser Tyr Pro Tyr Lys Ala Val Phe Ser
            100                 105                 110

Thr Gln Gly Pro Pro Leu Ala Ser Leu Gln Asp Ser His Phe Leu Thr
        115                 120                 125
```

```
Asp Ala Asp Met Val Met Ser Phe Val Asn Leu Val Glu His Asp Lys
    130                 135                 140

Glu Phe Phe His Pro Arg Tyr His His Arg Glu Arg Phe Asp Leu
145                 150                 155                 160

Ser Lys Ile Pro Glu Gly Glu Ala Val Thr Ala Ala Glu Phe Arg Ile
                165                 170                 175

Tyr Lys Asp Tyr Ile Arg Glu Arg Phe Asp Asn Glu Thr Phe Arg Ile
                180                 185                 190

Ser Val Tyr Gln Val Leu Gln Glu His Leu Gly Arg Glu Ser Asp Leu
            195                 200                 205

Phe Leu Leu Asp Ser Arg Thr Leu Trp Ala Ser Glu Glu Gly Trp Leu
    210                 215                 220

Val Phe Asp Ile Thr Ala Thr Ser Asn His Trp Val Val Asn Pro Arg
225                 230                 235                 240

His Asn Leu Gly Leu Gln Leu Ser Val Glu Thr Leu Asp Gly Gln Ser
                245                 250                 255

Ile Asn Pro Lys Leu Ala Gly Leu Ile Gly Arg His Gly Pro Gln Asn
                260                 265                 270

Lys Gln Pro Phe Met Val Ala Phe Phe Lys Ala Thr Glu Val His Phe
                275                 280                 285

Arg Ser Ile Arg Ser Thr Gly Ser Lys Gln Arg Ser Gln Asn Arg Ser
290                 295                 300

Lys Thr Pro Lys Asn Gln Glu Ala Leu Arg Met Ala Asn Val Ala Glu
305                 310                 315                 320

Asn Ser Ser Ser Asp Gln Arg Gln Ala Cys Lys Lys His Glu Leu Tyr
                325                 330                 335

Val Ser Phe Arg Asp Leu Gly Trp Gln Asp Trp Ile Ile Ala Pro Glu
                340                 345                 350

Gly Tyr Ala Ala Tyr Tyr Cys Glu Gly Glu Cys Ala Phe Pro Leu Asn
                355                 360                 365

Ser Tyr Met Asn Ala Thr Asn His Ala Ile Val Gln Thr Leu Val His
            370                 375                 380

Phe Ile Asn Pro Glu Thr Val Pro Lys Pro Cys Cys Ala Pro Thr Gln
385                 390                 395                 400

Leu Asn Ala Ile Ser Val Leu Tyr Phe Asp Asp Ser Ser Asn Val Ile
                405                 410                 415

Leu Lys Lys Tyr Arg Asn Met Val Val Arg Ala Cys Gly Cys His
                420                 425                 430

<210> SEQ ID NO 2
<211> LENGTH: 97
<212> TYPE: PRT
<213> ORGANISM: Homo sapiens

<400> SEQUENCE: 2

Leu Tyr Val Ser Phe Arg Asp Leu Gly Trp Gln Asp Trp Ile Ile Ala
1               5                   10                  15

Pro Glu Gly Tyr Ala Ala Tyr Tyr Cys Glu Gly Glu Cys Ala Phe Pro
                20                  25                  30

Leu Asn Ser Tyr Met Asn Ala Thr Asn His Ala Ile Val Gln Thr Leu
            35                  40                  45

Val His Phe Ile Asn Pro Glu Thr Val Pro Lys Pro Cys Cys Ala Pro
        50                  55                  60

Thr Gln Leu Asn Ala Ile Ser Val Leu Tyr Phe Asp Asp Ser Ser Asn
65                  70                  75                  80
```

```
Val Ile Leu Lys Lys Tyr Arg Asn Met Val Arg Ala Cys Gly Cys
                85                  90                  95

His

<210> SEQ ID NO 3
<211> LENGTH: 139
<212> TYPE: PRT
<213> ORGANISM: Homo sapiens

<400> SEQUENCE: 3

Ser Thr Gly Ser Lys Gln Arg Ser Gln Asn Arg Ser Lys Thr Pro Lys
1               5                   10                  15

Asn Gln Glu Ala Leu Arg Met Ala Asn Val Ala Glu Asn Ser Ser Ser
            20                  25                  30

Asp Gln Arg Gln Ala Cys Lys Lys His Glu Leu Tyr Val Ser Phe Arg
        35                  40                  45

Asp Leu Gly Trp Gln Asp Trp Ile Ile Ala Pro Glu Gly Tyr Ala Ala
    50                  55                  60

Tyr Tyr Cys Glu Gly Glu Cys Ala Phe Pro Leu Asn Ser Tyr Met Asn
65                  70                  75                  80

Ala Thr Asn His Ala Ile Val Gln Thr Leu Val His Phe Ile Asn Pro
                85                  90                  95

Glu Thr Val Pro Lys Pro Cys Cys Ala Pro Thr Gln Leu Asn Ala Ile
            100                 105                 110

Ser Val Leu Tyr Phe Asp Asp Ser Asn Val Ile Leu Lys Lys Tyr
        115                 120                 125

Arg Asn Met Val Val Arg Ala Cys Gly Cys His
    130                 135

<210> SEQ ID NO 4
<211> LENGTH: 430
<212> TYPE: PRT
<213> ORGANISM: Mus sp.

<400> SEQUENCE: 4

Met His Val Arg Ser Leu Arg Ala Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
        35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
            100                 105                 110

Gln Gly Pro Pro Leu Ala Ser Leu Gln Asp Ser His Phe Leu Thr Asp
        115                 120                 125

Ala Asp Met Val Met Ser Phe Val Asn Leu Val Glu His Asp Lys Glu
    130                 135                 140

Phe Phe His Pro Arg Tyr His His Arg Glu Phe Arg Phe Asp Leu Ser
145                 150                 155                 160

Lys Ile Pro Glu Gly Glu Ala Val Thr Ala Ala Glu Phe Arg Ile Tyr
                165                 170                 175
```

-continued

Lys Asp Tyr Ile Arg Glu Arg Phe Asp Asn Glu Thr Phe Gln Ile Thr
                180                 185                 190

Val Tyr Gln Val Leu Gln Glu His Ser Gly Arg Glu Ser Asp Leu Phe
            195                 200                 205

Leu Leu Asp Ser Arg Thr Ile Trp Ala Ser Glu Gly Trp Leu Val
        210                 215                 220

Phe Asp Ile Thr Ala Thr Ser Asn His Trp Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
                260                 265                 270

Gln Pro Phe Met Val Ala Phe Lys Ala Thr Glu Val His Leu Arg
            275                 280                 285

Ser Ile Arg Ser Thr Gly Gly Lys Gln Arg Ser Gln Asn Arg Ser Lys
                290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys His Glu Leu Tyr Val
            325                 330                 335

Ser Phe Arg Asp Leu Gly Trp Gln Asp Trp Ile Ile Ala Pro Glu Gly
                340                 345                 350

Tyr Ala Ala Tyr Tyr Cys Glu Gly Glu Cys Ala Phe Pro Leu Asn Ser
                355                 360                 365

Tyr Met Asn Ala Thr Asn His Ala Ile Val Gln Thr Leu Val His Phe
            370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Ile Leu
                405                 410                 415

Lys Lys Tyr Arg Asn Met Val Val Arg Ala Cys Gly Cys His
            420                 425                 430

<210> SEQ ID NO 5
<211> LENGTH: 139
<212> TYPE: PRT
<213> ORGANISM: Homo sapiens

<400> SEQUENCE: 5

Ala Val Arg Pro Leu Arg Arg Arg Gln Pro Lys Lys Ser Asn Glu Leu
1               5                   10                  15

Pro Gln Ala Asn Arg Leu Pro Gly Ile Phe Asp Asp Val His Gly Ser
            20                  25                  30

His Gly Arg Gln Val Cys Arg Arg His Glu Leu Tyr Val Ser Phe Gln
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ser Phe Pro Leu Asp Ser Cys Met Asn
65                  70                  75                  80

Ala Thr Asn His Ala Ile Leu Gln Ser Leu Val His Leu Met Met Pro
                85                  90                  95

Asp Ala Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

<210> SEQ ID NO 6
<211> LENGTH: 139
<212> TYPE: PRT
<213> ORGANISM: Mus sp.

<400> SEQUENCE: 6

Ala Ala Arg Pro Leu Lys Arg Arg Gln Pro Lys Lys Thr Asn Glu Leu
1               5                   10                  15

Pro His Pro Asn Lys Leu Pro Gly Ile Phe Asp Asp Gly His Gly Ser
            20                  25                  30

Arg Gly Arg Glu Val Cys Arg Arg His Glu Leu Tyr Val Ser Phe Arg
        35                  40                  45

Asp Leu Gly Trp Leu Asp Trp Val Ile Ala Pro Gln Gly Tyr Ser Ala
    50                  55                  60

Tyr Tyr Cys Glu Gly Glu Cys Ala Phe Pro Leu Asp Ser Cys Met Asn
65                  70                  75                  80

Ala Thr Asn His Ala Ile Leu Gln Ser Leu Val His Leu Met Lys Pro
                85                  90                  95

Asp Val Val Pro Lys Ala Cys Cys Ala Pro Thr Lys Leu Ser Ala Thr
            100                 105                 110

Ser Val Leu Tyr Tyr Asp Ser Ser Asn Asn Val Ile Leu Arg Lys His
        115                 120                 125

Arg Asn Met Val Val Lys Ala Cys Gly Cys His
    130                 135

<210> SEQ ID NO 7
<211> LENGTH: 588
<212> TYPE: PRT
<213> ORGANISM: Drosophila sp.

<400> SEQUENCE: 7

Met Arg Ala Trp Leu Leu Leu Ala Val Leu Ala Thr Phe Gln Thr
1               5                   10                  15

Ile Val Arg Val Ala Ser Thr Glu Asp Ile Ser Gln Arg Phe Ile Ala
            20                  25                  30

Ala Ile Ala Pro Val Ala Ala His Ile Pro Leu Ala Ser Ala Ser Gly
        35                  40                  45

Ser Gly Ser Gly Arg Ser Gly Ser Arg Ser Gly Gly Ala Ser Thr Ser
    50                  55                  60

Thr Ala Leu Ala Lys Ala Phe Asn Pro Phe Ser Glu Pro Ala Ser Phe
65                  70                  75                  80

Ser Asp Ser Asp Lys Ser His Arg Ser Lys Thr Asn Lys Lys Pro Ser
                85                  90                  95

Lys Ser Asp Ala Asn Arg Gln Phe Asn Glu Val His Lys Pro Arg Thr
            100                 105                 110

Asp Gln Leu Glu Asn Ser Lys Asn Met Ser Lys Gln Leu Val Asn Lys
        115                 120                 125

Pro Asn His Asn Lys Met Ala Val Lys Glu Gln Arg Ser His His Lys
    130                 135                 140

Lys Ser His His His Arg Ser His Gln Pro Lys Gln Ala Ser Ala Ser
145                 150                 155                 160

Thr Glu Ser His Gln Ser Ser Ser Ile Glu Ser Ile Phe Val Glu Glu
                165                 170                 175

-continued

Pro Thr Leu Val Leu Asp Arg Glu Val Ala Ser Ile Asn Val Pro Ala
            180                 185                 190

Asn Ala Lys Ala Ile Ile Ala Glu Gln Gly Pro Ser Thr Tyr Ser Lys
        195                 200                 205

Glu Ala Leu Ile Lys Asp Lys Leu Lys Pro Asp Pro Ser Thr Leu Val
210                 215                 220

Glu Ile Glu Lys Ser Leu Leu Ser Leu Phe Asn Met Lys Arg Pro Pro
225                 230                 235                 240

Lys Ile Asp Arg Ser Lys Ile Ile Pro Glu Pro Met Lys Lys Leu
            245                 250                 255

Tyr Ala Glu Ile Met Gly His Glu Leu Asp Ser Val Asn Ile Pro Lys
            260                 265                 270

Pro Gly Leu Leu Thr Lys Ser Ala Asn Thr Val Arg Ser Phe Thr His
        275                 280                 285

Lys Asp Ser Lys Ile Asp Asp Arg Phe Pro His His His Arg Phe Arg
290                 295                 300

Leu His Phe Asp Val Lys Ser Ile Pro Ala Asp Glu Lys Leu Lys Ala
305                 310                 315                 320

Ala Glu Leu Gln Leu Thr Arg Asp Ala Leu Ser Gln Gln Val Val Ala
            325                 330                 335

Ser Arg Ser Ser Ala Asn Arg Thr Arg Tyr Gln Val Leu Val Tyr Asp
        340                 345                 350

Ile Thr Arg Val Gly Val Arg Gly Gln Arg Glu Pro Ser Tyr Leu Leu
        355                 360                 365

Leu Asp Thr Lys Thr Val Arg Leu Asn Ser Thr Asp Thr Val Ser Leu
        370                 375                 380

Asp Val Gln Pro Ala Val Asp Arg Trp Leu Ala Ser Pro Gln Arg Asn
385                 390                 395                 400

Tyr Gly Leu Leu Val Glu Val Arg Thr Val Arg Ser Leu Lys Pro Ala
            405                 410                 415

Pro His His His Val Arg Leu Arg Arg Ser Ala Asp Glu Ala His Glu
        420                 425                 430

Arg Trp Gln His Lys Gln Pro Leu Leu Phe Thr Tyr Thr Asp Asp Gly
        435                 440                 445

Arg His Lys Ala Arg Ser Ile Arg Asp Val Ser Gly Gly Glu Gly Gly
        450                 455                 460

Gly Lys Gly Gly Arg Asn Lys Arg Gln Pro Arg Arg Pro Thr Arg Arg
465                 470                 475                 480

Lys Asn His Asp Asp Thr Cys Arg Arg His Ser Leu Tyr Val Asp Phe
            485                 490                 495

Ser Asp Val Gly Trp Asp Asp Trp Ile Val Ala Pro Leu Gly Tyr Asp
        500                 505                 510

Ala Tyr Tyr Cys His Gly Lys Cys Pro Phe Pro Leu Ala Asp His Phe
        515                 520                 525

Asn Ser Thr Asn His Ala Val Val Gln Thr Leu Val Asn Asn Met Asn
530                 535                 540

Pro Gly Lys Val Pro Lys Ala Cys Cys Val Pro Thr Gln Leu Asp Ser
545                 550                 555                 560

Val Ala Met Leu Tyr Leu Asn Asp Gln Ser Thr Val Val Leu Lys Asn
            565                 570                 575

Tyr Gln Glu Met Thr Val Val Gly Cys Gly Cys Arg
            580                 585

<210> SEQ ID NO 8

```
<211> LENGTH: 360
<212> TYPE: PRT
<213> ORGANISM: Xenopus sp.

<400> SEQUENCE: 8

Met Val Trp Leu Arg Leu Trp Ala Phe Leu His Ile Leu Ala Ile Val
1               5                   10                  15

Thr Leu Asp Pro Glu Leu Lys Arg Arg Glu Glu Leu Phe Leu Arg Ser
            20                  25                  30

Leu Gly Phe Ser Ser Lys Pro Asn Pro Val Ser Pro Pro Val Pro
        35                  40                  45

Ser Ile Leu Trp Arg Ile Phe Asn Gln Arg Met Gly Ser Ser Ile Gln
    50                  55                  60

Lys Lys Lys Pro Asp Leu Cys Phe Val Glu Glu Phe Asn Val Pro Gly
65                  70                  75                  80

Ser Val Ile Arg Val Phe Pro Asp Gln Gly Arg Phe Ile Ile Pro Tyr
                85                  90                  95

Ser Asp Asp Ile His Pro Thr Gln Cys Leu Glu Lys Arg Leu Phe Phe
            100                 105                 110

Asn Ile Ser Ala Ile Glu Lys Glu Arg Val Thr Met Gly Ser Gly
        115                 120                 125

Ile Glu Val Gln Pro Glu His Leu Leu Arg Lys Gly Ile Asp Leu Arg
130                 135                 140

Leu Tyr Arg Thr Leu Gln Ile Thr Leu Lys Gly Met Gly Arg Ser Lys
145                 150                 155                 160

Thr Ser Arg Lys Leu Leu Val Ala Gln Thr Phe Arg Leu Leu His Lys
                165                 170                 175

Ser Leu Phe Phe Asn Leu Thr Glu Ile Cys Gln Ser Trp Gln Asp Pro
            180                 185                 190

Leu Lys Asn Leu Gly Leu Val Leu Glu Ile Phe Pro Lys Lys Glu Ser
        195                 200                 205

Ser Trp Met Ser Thr Ala Asn Asp Glu Cys Lys Asp Ile Gln Thr Phe
    210                 215                 220

Leu Tyr Thr Ser Leu Leu Thr Val Thr Leu Asn Pro Leu Arg Cys Lys
225                 230                 235                 240

Arg Pro Arg Arg Lys Arg Ser Tyr Ser Lys Leu Pro Phe Thr Ala Ser
                245                 250                 255

Asn Ile Cys Lys Lys Arg His Leu Tyr Val Glu Phe Lys Asp Val Gly
            260                 265                 270

Trp Gln Asn Trp Val Ile Ala Pro Gln Gly Tyr Met Ala Asn Tyr Cys
        275                 280                 285

Tyr Gly Glu Cys Pro Tyr Pro Leu Thr Glu Ile Leu Asn Gly Ser Asn
    290                 295                 300

His Ala Ile Leu Gln Thr Leu Val His Ser Ile Glu Pro Glu Asp Ile
305                 310                 315                 320

Pro Leu Pro Cys Cys Val Pro Thr Lys Met Ser Pro Ile Ser Met Leu
                325                 330                 335

Phe Tyr Asp Asn Asn Asp Asn Val Val Leu Arg His Tyr Glu Asn Met
            340                 345                 350

Ala Val Asp Glu Cys Gly Cys Arg
        355                 360

<210> SEQ ID NO 9
<211> LENGTH: 438
<212> TYPE: PRT
<213> ORGANISM: Mus sp.
```

<400> SEQUENCE: 9

```
Met Arg Lys Met Gln Lys Glu Ile Leu Ser Val Leu Gly Pro Pro His
1               5                   10                  15

Arg Pro Arg Pro Leu His Gly Leu Gln Gln Pro Gln Pro Pro Val Leu
            20                  25                  30

Pro Pro Gln Gln Gln Gln Gln Gln Gln Gln Thr Ala Arg Glu
        35                  40                  45

Glu Pro Pro Gly Arg Leu Lys Ser Ala Pro Leu Phe Met Leu Asp
50                  55                  60

Leu Tyr Asn Ala Leu Ser Asn Asp Asp Glu Glu Asp Gly Ala Ser Glu
65                  70                  75                  80

Gly Val Gly Gln Glu Pro Gly Ser His Gly Ala Ser Ser Ser Gln
            85                  90                  95

Leu Arg Gln Pro Ser Pro Gly Ala Ala His Ser Leu Asn Arg Lys Ser
            100                 105                 110

Leu Leu Ala Pro Gly Pro Gly Gly Ala Ser Pro Leu Thr Ser Ala
        115                 120                 125

Gln Asp Ser Ala Phe Leu Asn Asp Ala Asp Met Val Met Ser Phe Val
130                 135                 140

Asn Leu Val Glu Tyr Asp Lys Glu Phe Ser Pro His Gln Arg His His
145                 150                 155                 160

Lys Glu Phe Lys Phe Asn Leu Ser Gln Ile Pro Glu Gly Glu Ala Val
                165                 170                 175

Thr Ala Ala Glu Phe Arg Val Tyr Lys Asp Cys Val Val Gly Ser Phe
            180                 185                 190

Lys Asn Gln Thr Phe Leu Ile Ser Ile Tyr Gln Val Leu Gln Glu His
        195                 200                 205

Gln His Arg Asp Ser Asp Leu Phe Leu Leu Asp Thr Arg Val Val Trp
    210                 215                 220

Ala Ser Glu Glu Gly Trp Leu Glu Phe Asp Ile Thr Ala Thr Ser Asn
225                 230                 235                 240

Leu Trp Val Val Thr Pro Gln His Asn Met Gly Leu Gln Leu Ser Val
                245                 250                 255

Val Thr Arg Asp Gly Leu His Val Asn Pro Arg Ala Ala Gly Leu Val
            260                 265                 270

Gly Arg Asp Gly Pro Tyr Asp Lys Gln Pro Phe Met Val Ala Phe Phe
        275                 280                 285

Lys Val Ser Glu Val His Val Arg Thr Thr Arg Ser Ala Ser Ser Arg
290                 295                 300

Arg Arg Gln Gln Ser Arg Asn Arg Ser Thr Gln Ser Gln Asp Val Ser
305                 310                 315                 320

Arg Gly Ser Gly Ser Ser Asp Tyr Asn Gly Ser Glu Leu Lys Thr Ala
                325                 330                 335

Cys Lys Lys His Glu Leu Tyr Val Ser Phe Gln Asp Leu Gly Trp Gln
            340                 345                 350

Asp Trp Ile Ile Ala Pro Lys Gly Tyr Ala Ala Asn Tyr Cys Asp Gly
        355                 360                 365

Glu Cys Ser Phe Pro Leu Asn Ala His Met Asn Ala Thr Asn His Ala
    370                 375                 380

Ile Val Gln Thr Leu Val His Leu Met Asn Pro Glu Tyr Val Pro Lys
385                 390                 395                 400

Pro Cys Cys Ala Pro Thr Lys Leu Asn Ala Ile Ser Val Leu Tyr Phe
                405                 410                 415
```

```
Asp Asp Asn Ser Asn Val Ile Leu Lys Lys Tyr Arg Asn Met Val Val
            420                 425                 430

Arg Ala Cys Gly Cys His
        435

<210> SEQ ID NO 10
<211> LENGTH: 396
<212> TYPE: PRT
<213> ORGANISM: Homo sapiens

<400> SEQUENCE: 10

Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
    50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
    210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
    290                 295                 300

Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350
```

Asn Ser Lys Ile Pro Lys Ala Cys Cys Val Pro Thr Glu Leu Ser Ala
            355                 360                 365

Ile Ser Met Leu Tyr Leu Asp Glu Asn Glu Lys Val Val Leu Lys Asn
            370                 375                 380

Tyr Gln Asp Met Val Val Glu Gly Cys Gly Cys Arg
385                 390                 395

<210> SEQ ID NO 11
<211> LENGTH: 408
<212> TYPE: PRT
<213> ORGANISM: Homo sapiens

<400> SEQUENCE: 11

Met Ile Pro Gly Asn Arg Met Leu Met Val Val Leu Leu Cys Gln Val
1               5                   10                  15

Leu Leu Gly Gly Ala Ser His Ala Ser Leu Ile Pro Glu Thr Gly Lys
            20                  25                  30

Lys Lys Val Ala Glu Ile Gln Gly His Ala Gly Gly Arg Arg Ser Gly
        35                  40                  45

Gln Ser His Glu Leu Leu Arg Asp Phe Glu Ala Thr Leu Leu Gln Met
    50                  55                  60

Phe Gly Leu Arg Arg Arg Pro Gln Pro Ser Lys Ser Ala Val Ile Pro
65                  70                  75                  80

Asp Tyr Met Arg Asp Leu Tyr Arg Leu Gln Ser Gly Glu Glu Glu Glu
                85                  90                  95

Glu Gln Ile His Ser Thr Gly Leu Glu Tyr Pro Glu Arg Pro Ala Ser
            100                 105                 110

Arg Ala Asn Thr Val Arg Ser Phe His His Glu Glu His Leu Glu Asn
        115                 120                 125

Ile Pro Gly Thr Ser Glu Asn Ser Ala Phe Arg Phe Leu Phe Asn Leu
    130                 135                 140

Ser Ser Ile Pro Glu Asn Glu Val Ile Ser Ser Ala Glu Leu Arg Leu
145                 150                 155                 160

Phe Arg Glu Gln Val Asp Gln Gly Pro Asp Trp Glu Arg Gly Phe His
                165                 170                 175

Arg Ile Asn Ile Tyr Glu Val Met Lys Pro Pro Ala Glu Val Val Pro
            180                 185                 190

Gly His Leu Ile Thr Arg Leu Leu Asp Thr Arg Leu Val His His Asn
        195                 200                 205

Val Thr Arg Trp Glu Thr Phe Asp Val Ser Pro Ala Val Leu Arg Trp
    210                 215                 220

Thr Arg Glu Lys Gln Pro Asn Tyr Gly Leu Ala Ile Glu Val Thr His
225                 230                 235                 240

Leu His Gln Thr Arg Thr His Gln Gly Gln His Val Arg Ile Ser Arg
                245                 250                 255

Ser Leu Pro Gln Gly Ser Gly Asn Trp Ala Gln Leu Arg Pro Leu Leu
            260                 265                 270

Val Thr Phe Gly His Asp Gly Arg Gly His Ala Leu Thr Arg Arg Arg
        275                 280                 285

Arg Ala Lys Arg Ser Pro Lys His His Ser Gln Arg Ala Arg Lys Lys
    290                 295                 300

Asn Lys Asn Cys Arg Arg His Ser Leu Tyr Val Asp Phe Ser Asp Val
305                 310                 315                 320

Gly Trp Asn Asp Trp Ile Val Ala Pro Pro Gly Tyr Gln Ala Phe Tyr
                325                 330                 335

```
Cys His Gly Asp Cys Pro Phe Pro Leu Ala Asp His Leu Asn Ser Thr
            340                 345                 350

Asn His Ala Ile Val Gln Thr Leu Val Asn Ser Val Asn Ser Ser Ile
        355                 360                 365

Pro Lys Ala Cys Cys Val Pro Thr Glu Leu Ser Ala Ile Ser Met Leu
370                 375                 380

Tyr Leu Asp Glu Tyr Asp Lys Val Val Leu Lys Asn Tyr Gln Glu Met
385                 390                 395                 400

Val Val Glu Gly Cys Gly Cys Arg
                405

<210> SEQ ID NO 12
<211> LENGTH: 472
<212> TYPE: PRT
<213> ORGANISM: Homo sapiens

<400> SEQUENCE: 12

Met Ala Gly Ala Ser Arg Leu Leu Phe Leu Trp Leu Gly Cys Phe Cys
1               5                   10                  15

Val Ser Leu Ala Gln Gly Glu Arg Pro Lys Pro Pro Phe Pro Glu Leu
            20                  25                  30

Arg Lys Ala Val Pro Gly Asp Arg Thr Ala Gly Gly Gly Pro Asp Ser
        35                  40                  45

Glu Leu Gln Pro Gln Asp Lys Val Ser Glu His Met Leu Arg Leu Tyr
50                  55                  60

Asp Arg Tyr Ser Thr Val Gln Ala Ala Arg Thr Pro Gly Ser Leu Glu
65                  70                  75                  80

Gly Gly Ser Gln Pro Trp Arg Pro Arg Leu Leu Arg Glu Gly Asn Thr
                85                  90                  95

Val Arg Ser Phe Arg Ala Ala Ala Glu Thr Leu Glu Arg Lys Gly
            100                 105                 110

Leu Tyr Ile Phe Asn Leu Thr Ser Leu Thr Lys Ser Glu Asn Ile Leu
        115                 120                 125

Ser Ala Thr Leu Tyr Phe Cys Ile Gly Glu Leu Gly Asn Ile Ser Leu
130                 135                 140

Ser Cys Pro Val Ser Gly Gly Cys Ser His His Ala Gln Arg Lys His
145                 150                 155                 160

Ile Gln Ile Asp Leu Ser Ala Trp Thr Leu Lys Phe Ser Arg Asn Gln
                165                 170                 175

Ser Gln Leu Leu Gly His Leu Ser Val Asp Met Ala Lys Ser His Arg
            180                 185                 190

Asp Ile Met Ser Trp Leu Ser Lys Asp Ile Thr Gln Phe Leu Arg Lys
        195                 200                 205

Ala Lys Glu Asn Glu Glu Phe Leu Ile Gly Phe Asn Ile Thr Ser Lys
210                 215                 220

Gly Arg Gln Leu Pro Lys Arg Arg Leu Pro Phe Pro Glu Pro Tyr Ile
225                 230                 235                 240

Leu Val Tyr Ala Asn Asp Ala Ala Ile Ser Glu Pro Glu Ser Val Val
                245                 250                 255

Ser Ser Leu Gln Gly His Arg Asn Phe Pro Thr Gly Thr Val Pro Lys
            260                 265                 270

Trp Asp Ser His Ile Arg Ala Ala Leu Ser Ile Glu Arg Arg Lys Lys
        275                 280                 285

Arg Ser Thr Gly Val Leu Leu Pro Leu Gln Asn Asn Glu Leu Pro Gly
290                 295                 300
```

```
Ala Glu Tyr Gln Tyr Lys Lys Asp Glu Val Trp Glu Arg Lys Pro
305                 310                 315                 320

Tyr Lys Thr Leu Gln Ala Gln Ala Pro Glu Lys Ser Lys Asn Lys Lys
            325                 330                 335

Lys Gln Arg Lys Gly Pro His Arg Lys Ser Gln Thr Leu Gln Phe Asp
            340                 345                 350

Glu Gln Thr Leu Lys Lys Ala Arg Arg Lys Gln Trp Ile Glu Pro Arg
            355                 360                 365

Asn Cys Ala Arg Arg Tyr Leu Lys Val Asp Phe Ala Asp Ile Gly Trp
        370                 375                 380

Ser Glu Trp Ile Ile Ser Pro Lys Ser Phe Asp Ala Tyr Tyr Cys Ser
385                 390                 395                 400

Gly Ala Cys Gln Phe Pro Met Pro Lys Ser Leu Lys Pro Ser Asn His
                405                 410                 415

Ala Thr Ile Gln Ser Ile Val Arg Ala Val Gly Val Val Pro Gly Ile
            420                 425                 430

Pro Glu Pro Cys Cys Val Pro Glu Lys Met Ser Ser Leu Ser Ile Leu
            435                 440                 445

Phe Phe Asp Glu Asn Lys Asn Val Val Leu Lys Val Tyr Pro Asn Met
450                 455                 460

Thr Val Glu Ser Cys Ala Cys Arg
465                 470

<210> SEQ ID NO 13
<211> LENGTH: 372
<212> TYPE: PRT
<213> ORGANISM: Homo sapiens

<400> SEQUENCE: 13

Met Pro Pro Pro Gln Gln Gly Pro Cys Gly His His Leu Leu Leu Leu
1               5                   10                  15

Leu Ala Leu Leu Leu Pro Ser Leu Pro Leu Thr Arg Ala Pro Val Pro
            20                  25                  30

Pro Gly Pro Ala Ala Ala Leu Leu Gln Ala Leu Gly Leu Arg Asp Glu
        35                  40                  45

Pro Gln Gly Ala Pro Arg Leu Arg Pro Val Pro Pro Val Met Trp Arg
    50                  55                  60

Leu Phe Arg Arg Arg Asp Pro Gln Glu Thr Arg Ser Gly Ser Arg Arg
65                  70                  75                  80

Thr Ser Pro Gly Val Thr Leu Gln Pro Cys His Val Glu Glu Leu Gly
                85                  90                  95

Val Ala Gly Asn Ile Val Arg His Ile Pro Asp Arg Gly Ala Pro Thr
            100                 105                 110

Arg Ala Ser Glu Pro Val Ser Ala Ala Gly His Cys Pro Glu Trp Thr
        115                 120                 125

Val Val Phe Asp Leu Ser Ala Val Glu Pro Ala Glu Arg Pro Ser Arg
    130                 135                 140

Ala Arg Leu Glu Leu Arg Phe Ala Ala Ala Ala Ala Ala Pro Glu
145                 150                 155                 160

Gly Gly Trp Glu Leu Ser Val Ala Gln Ala Gly Gln Gly Ala Gly Ala
                165                 170                 175

Asp Pro Gly Pro Val Leu Leu Arg Gln Leu Val Pro Ala Leu Gly Pro
            180                 185                 190

Pro Val Arg Ala Glu Leu Leu Gly Ala Ala Trp Ala Arg Asn Ala Ser
        195                 200                 205
```

```
Trp Pro Arg Ser Leu Arg Leu Ala Leu Ala Leu Arg Pro Arg Ala Pro
    210                 215                 220

Ala Ala Cys Ala Arg Leu Ala Glu Ala Ser Leu Leu Val Thr Leu
225                 230                 235                 240

Asp Pro Arg Leu Cys His Pro Leu Ala Arg Pro Arg Asp Ala Glu
                    245                 250                 255

Pro Val Leu Gly Gly Gly Pro Gly Ala Cys Arg Ala Arg Arg Leu
            260                 265                 270

Tyr Val Ser Phe Arg Glu Val Gly Trp His Arg Trp Val Ile Ala Pro
        275                 280                 285

Arg Gly Phe Leu Ala Asn Tyr Cys Gln Gly Gln Cys Ala Leu Pro Val
    290                 295                 300

Ala Leu Ser Gly Ser Gly Gly Pro Pro Ala Leu Asn His Ala Val Leu
305                 310                 315                 320

Arg Ala Leu Met His Ala Ala Ala Pro Gly Ala Ala Asp Leu Pro Cys
                    325                 330                 335

Cys Val Pro Ala Arg Leu Ser Pro Ile Ser Val Leu Phe Phe Asp Asn
                340                 345                 350

Ser Asp Asn Val Val Leu Arg Gln Tyr Glu Asp Met Val Val Asp Glu
                    355                 360                 365

Cys Gly Cys Arg
    370

<210> SEQ ID NO 14
<211> LENGTH: 455
<212> TYPE: PRT
<213> ORGANISM: Drosophila sp.

<400> SEQUENCE: 14

Met Ser Gly Leu Arg Asn Thr Ser Glu Ala Val Ala Val Leu Ala Ser
1               5                   10                  15

Leu Gly Leu Gly Met Val Leu Leu Met Phe Val Ala Thr Thr Pro Pro
                20                  25                  30

Ala Val Glu Ala Thr Gln Ser Gly Ile Tyr Ile Asp Asn Gly Lys Asp
                35                  40                  45

Gln Thr Ile Met His Arg Val Leu Ser Glu Asp Asp Lys Leu Asp Val
    50                  55                  60

Ser Tyr Glu Ile Leu Glu Phe Leu Gly Ile Ala Glu Arg Pro Thr His
65                  70                  75                  80

Leu Ser Ser His Gln Leu Ser Leu Arg Lys Ser Ala Pro Lys Phe Leu
                85                  90                  95

Leu Asp Val Tyr His Arg Ile Thr Ala Glu Glu Gly Leu Ser Asp Gln
                100                 105                 110

Asp Glu Asp Asp Tyr Glu Arg Gly His Arg Ser Arg Arg Ser Ala
            115                 120                 125

Asp Leu Glu Glu Asp Glu Gly Glu Gln Gln Lys Asn Phe Ile Thr Asp
    130                 135                 140

Leu Asp Lys Arg Ala Ile Asp Glu Ser Asp Ile Ile Met Thr Phe Leu
145                 150                 155                 160

Asn Lys Arg His His Asn Val Asp Glu Leu Arg His Glu His Gly Arg
                165                 170                 175

Arg Leu Trp Phe Asp Val Ser Asn Val Pro Asn Asp Asn Tyr Leu Val
            180                 185                 190

Met Ala Glu Leu Arg Ile Tyr Gln Asn Ala Asn Glu Gly Lys Trp Leu
        195                 200                 205
```

Thr Ala Asn Arg Glu Phe Thr Ile Thr Val Tyr Ala Ile Gly Thr Gly
            210                 215                 220

Thr Leu Gly Gln His Thr Met Glu Pro Leu Ser Ser Val Asn Thr Thr
225                 230                 235                 240

Gly Asp Tyr Val Gly Trp Leu Glu Leu Asn Val Thr Glu Gly Leu His
                245                 250                 255

Glu Trp Leu Val Lys Ser Lys Asp Asn His Gly Ile Tyr Ile Gly Ala
            260                 265                 270

His Ala Val Asn Arg Pro Asp Arg Glu Val Lys Leu Asp Asp Ile Gly
        275                 280                 285

Leu Ile His Arg Lys Val Asp Asp Glu Phe Gln Pro Phe Met Ile Gly
    290                 295                 300

Phe Phe Arg Gly Pro Glu Leu Ile Lys Ala Thr Ala His Ser Ser His
305                 310                 315                 320

His Arg Ser Lys Arg Ser Ala Ser His Pro Arg Lys Arg Lys Lys Ser
                325                 330                 335

Val Ser Pro Asn Asn Val Pro Leu Leu Glu Pro Met Glu Ser Thr Arg
            340                 345                 350

Ser Cys Gln Met Gln Thr Leu Tyr Ile Asp Phe Lys Asp Leu Gly Trp
        355                 360                 365

His Asp Trp Ile Ile Ala Pro Glu Gly Tyr Gly Ala Phe Tyr Cys Ser
    370                 375                 380

Gly Glu Cys Asn Phe Pro Leu Asn Ala His Met Asn Ala Thr Asn His
385                 390                 395                 400

Ala Ile Val Gln Thr Leu Val His Leu Leu Glu Pro Lys Lys Val Pro
                405                 410                 415

Lys Pro Cys Cys Ala Pro Thr Arg Leu Gly Ala Leu Pro Val Leu Tyr
            420                 425                 430

His Leu Asn Asp Glu Asn Val Asn Leu Lys Lys Tyr Arg Asn Met Ile
        435                 440                 445

Val Lys Ser Cys Gly Cys His
    450                 455

<210> SEQ ID NO 15
<211> LENGTH: 454
<212> TYPE: PRT
<213> ORGANISM: Homo sapiens

<400> SEQUENCE: 15

Met His Leu Thr Val Phe Leu Leu Lys Gly Ile Val Gly Phe Leu Trp
1               5                   10                  15

Ser Cys Trp Val Leu Val Gly Tyr Ala Lys Gly Gly Leu Gly Asp Asn
            20                  25                  30

His Val His Ser Ser Phe Ile Tyr Arg Arg Leu Arg Asn His Glu Arg
        35                  40                  45

Arg Glu Ile Gln Arg Glu Ile Leu Ser Ile Leu Gly Leu Pro His Arg
    50                  55                  60

Pro Arg Pro Phe Ser Pro Gly Lys Gln Ala Ser Ser Ala Pro Leu Phe
65                  70                  75                  80

Met Leu Asp Leu Tyr Asn Ala Met Thr Asn Glu Glu Asn Pro Glu Glu
                85                  90                  95

Ser Glu Tyr Ser Val Arg Ala Ser Leu Ala Glu Glu Thr Arg Gly Ala
            100                 105                 110

Arg Lys Gly Tyr Pro Ala Ser Pro Asn Gly Tyr Pro Arg Arg Ile Gln
        115                 120                 125

-continued

Leu Ser Arg Thr Thr Pro Leu Thr Thr Gln Ser Pro Pro Leu Ala Ser
    130                 135                 140

Leu His Asp Thr Asn Phe Leu Asn Asp Ala Asp Met Val Met Ser Phe
145                 150                 155                 160

Val Asn Leu Val Glu Arg Asp Lys Asp Phe Ser His Gln Arg Arg His
                165                 170                 175

Tyr Lys Glu Phe Arg Phe Asp Leu Thr Gln Ile Pro His Gly Glu Ala
            180                 185                 190

Val Thr Ala Ala Glu Phe Arg Ile Tyr Lys Asp Arg Ser Asn Asn Arg
        195                 200                 205

Phe Glu Asn Glu Thr Ile Lys Ile Ser Ile Tyr Gln Ile Ile Lys Glu
210                 215                 220

Tyr Thr Asn Arg Asp Ala Asp Leu Phe Leu Asp Thr Arg Lys Ala
225                 230                 235                 240

Gln Ala Leu Asp Val Gly Trp Leu Val Phe Asp Ile Thr Val Thr Ser
                245                 250                 255

Asn His Trp Val Ile Asn Pro Gln Asn Asn Leu Gly Leu Gln Leu Cys
            260                 265                 270

Ala Glu Thr Gly Asp Gly Arg Ser Ile Asn Val Lys Ser Ala Gly Leu
        275                 280                 285

Val Gly Arg Gln Gly Pro Gln Ser Lys Gln Pro Phe Met Val Ala Phe
290                 295                 300

Phe Lys Ala Ser Glu Val Leu Leu Arg Ser Val Arg Ala Ala Asn Lys
305                 310                 315                 320

Arg Lys Asn Gln Asn Arg Asn Lys Ser Ser His Gln Asp Ser Ser
                325                 330                 335

Arg Met Ser Ser Val Gly Asp Tyr Asn Thr Ser Glu Gln Lys Gln Ala
            340                 345                 350

Cys Lys Lys His Glu Leu Tyr Val Ser Phe Arg Asp Leu Gly Trp Gln
        355                 360                 365

Asp Trp Ile Ile Ala Pro Glu Gly Tyr Ala Ala Phe Tyr Cys Asp Gly
370                 375                 380

Glu Cys Ser Phe Pro Leu Asn Ala His Met Asn Ala Thr Asn His Ala
385                 390                 395                 400

Ile Val Gln Thr Leu Val His Leu Met Phe Pro Asp His Val Pro Lys
                405                 410                 415

Pro Cys Cys Ala Pro Thr Lys Leu Asn Ala Ile Ser Val Leu Tyr Phe
            420                 425                 430

Asp Asp Ser Ser Asn Val Ile Leu Lys Lys Tyr Arg Asn Met Val Val
        435                 440                 445

Arg Ser Cys Gly Cys His
    450

<210> SEQ ID NO 16
<211> LENGTH: 513
<212> TYPE: PRT
<213> ORGANISM: Homo sapiens

<400> SEQUENCE: 16

Met Pro Gly Leu Gly Arg Arg Ala Gln Trp Leu Cys Trp Trp Trp Gly
1               5                   10                  15

Leu Leu Cys Ser Cys Cys Gly Pro Pro Pro Leu Arg Pro Pro Leu Pro
                20                  25                  30

Ala Ala Ala Ala Ala Ala Gly Gly Gln Leu Leu Gly Asp Gly Gly
            35                  40                  45

Ser Pro Gly Arg Thr Glu Gln Pro Pro Ser Pro Gln Ser Ser Ser
    50                  55                  60

Gly Phe Leu Tyr Arg Arg Leu Lys Thr Gln Glu Lys Arg Glu Met Gln
 65                  70                  75                  80

Lys Glu Ile Leu Ser Val Leu Gly Leu Pro His Arg Pro Arg Pro Leu
                 85                  90                  95

His Gly Leu Gln Gln Pro Gln Pro Ala Leu Arg Gln Gln Glu Glu
                100                 105                 110

Gln Gln Gln Gln Gln Leu Pro Arg Gly Glu Pro Pro Gly Arg
            115                 120                 125

Leu Lys Ser Ala Pro Leu Phe Met Leu Asp Leu Tyr Asn Ala Leu Ser
130                 135                 140

Ala Asp Asn Asp Glu Asp Gly Ala Ser Glu Gly Glu Arg Gln Gln Ser
145                 150                 155                 160

Trp Pro His Glu Ala Ala Ser Ser Ser Gln Arg Arg Gln Pro Pro Pro
                165                 170                 175

Gly Ala Ala His Pro Leu Asn Arg Lys Ser Leu Leu Ala Pro Gly Ser
                180                 185                 190

Gly Ser Gly Gly Ala Ser Pro Leu Thr Ser Ala Gln Asp Ser Ala Phe
    195                 200                 205

Leu Asn Asp Ala Asp Met Val Met Ser Phe Val Asn Leu Val Glu Tyr
210                 215                 220

Asp Lys Glu Phe Ser Pro Arg Gln Arg His His Lys Glu Phe Lys Phe
225                 230                 235                 240

Asn Leu Ser Gln Ile Pro Glu Gly Glu Val Val Thr Ala Ala Glu Phe
                245                 250                 255

Arg Ile Tyr Lys Asp Cys Val Met Gly Ser Phe Lys Asn Gln Thr Phe
                260                 265                 270

Leu Ile Ser Ile Tyr Gln Val Leu Gln Glu His Gln His Arg Asp Ser
            275                 280                 285

Asp Leu Phe Leu Leu Asp Thr Arg Val Val Trp Ala Ser Glu Glu Gly
        290                 295                 300

Trp Leu Glu Phe Asp Ile Thr Ala Thr Ser Asn Leu Trp Val Val Thr
305                 310                 315                 320

Pro Gln His Asn Met Gly Leu Gln Leu Ser Val Val Thr Arg Asp Gly
                325                 330                 335

Val His Val His Pro Arg Ala Ala Gly Leu Val Gly Arg Asp Gly Pro
                340                 345                 350

Tyr Asp Lys Gln Pro Phe Met Val Ala Phe Phe Lys Val Ser Glu Val
            355                 360                 365

His Val Arg Thr Thr Arg Ser Ala Ser Ser Arg Arg Gln Gln Ser
        370                 375                 380

Arg Asn Arg Ser Thr Gln Ser Gln Asp Val Ala Arg Val Ser Ser Ala
385                 390                 395                 400

Ser Asp Tyr Asn Ser Ser Glu Leu Lys Thr Ala Cys Arg Lys His Glu
                405                 410                 415

Leu Tyr Val Ser Phe Gln Asp Leu Gly Trp Gln Asp Trp Ile Ile Ala
                420                 425                 430

Pro Lys Gly Tyr Ala Ala Asn Tyr Cys Asp Gly Glu Cys Ser Phe Pro
            435                 440                 445

Leu Asn Ala His Met Asn Ala Thr Asn His Ala Ile Val Gln Thr Leu
    450                 455                 460

Val His Leu Met Asn Pro Glu Tyr Val Pro Lys Pro Cys Cys Ala Pro

```
                465                 470                 475                 480
Thr Lys Leu Asn Ala Ile Ser Val Leu Tyr Phe Asp Asp Asn Ser Asn
                    485                 490                 495
Val Ile Leu Lys Lys Tyr Arg Asn Met Val Val Arg Ala Cys Gly Cys
                500                 505                 510
His
```

<210> SEQ ID NO 17
<211> LENGTH: 1878
<212> TYPE: DNA
<213> ORGANISM: Homo sapiens

<400> SEQUENCE: 17

```
gggcgcagcg gggcccgtct gcagcaagtg accgacggcc gggacggccg cctgccccct      60
ctgccacctg gggcggtgcg ggcccggagc ccggagcccg ggtagcgcgt agagccggcg     120
cgatgcacgt gcgctcactg cgagctgcgg cgccgcacag cttcgtggcg ctctgggcac     180
ccctgttcct gctgcgctcc gccctggccg acttcagcct ggacaacgag gtgcactcga     240
gcttcatcca ccggcgcctc cgcagccagg agcggcggga gatgcagcgc gagatcctct     300
ccattttggg cttgccccac cgcccgcgcc cgcacctcca gggcaagcac aactcggcac     360
ccatgttcat gctggacctg tacaacgcca tggcggtgga ggagggcggc gggcccggcg     420
gccagggctt ctcctacccc tacaaggccg tcttcagtac ccagggcccc cctctggcca     480
gcctgcaaga tagccatttc ctcaccgacg ccgacatggt catgagcttc gtcaacctcg     540
tggaacatga caaggaattc ttccacccac gctaccacca tcgagagttc cggtttgatc     600
tttccaagat cccagaaggg gaagctgtca cggcagccga attccggatc tacaaggact     660
acatccggga acgcttcgac aatgagacgt tccggatcag cgtttatcag gtgctccagg     720
agcacttggg cagggaatcg gatctcttcc tgctcgacag ccgtaccctc tgggcctcgg     780
aggagggctg gctggtgttt gacatcacag ccaccagcaa ccactgggtg gtcaatccgc     840
ggcacaacct gggcctgcag ctctcggtgg agacgctgga tgggcagagc atcaacccca     900
agttggcggg cctgattggg cggcacgggc ccagaacaa gcagccctttc atggtggctt     960
tcttcaaggc cacggaggtc cacttccgca gcatccggtc cacggggagc aaacagcgca    1020
gccagaaccg ctccaagacg cccaagaacc aggaagccct gcggatggcc aacgtggcag    1080
agaacagcag cagcgaccag aggcaggcct gtaagaagca cgagctgtat gtcagcttcc    1140
gagacctggg ctggcaggac tggatcatcg cgcctgaagg ctacgccgcc tactactgtg    1200
agggggagtg tgccttccct ctgaactcct acatgaacgc caccaaccac gccatcgtgc    1260
agacgctggt ccacttcatc aacccggaaa cggtgcccaa gccctgctgt gcgcccacgc    1320
agctcaatgc catctccgtc ctctacttcg atgacagctc caacgtcatc ctgaagaaat    1380
acagaaacat ggtggtccgg gcctgtggct gccactagct cctccgagaa ttcagaccct    1440
tggggccaa gttttttctgg atcctccatt gctcgccttg gcaggaacc agcagaccaa    1500
ctgcctttg tgagaccttc ccctcccctat ccccaacttt aaaggtgtga gagtattagg    1560
aaacatgagc agcatatggc tttttgatcag tttttcagtg gcagcatcca atgaacaaga    1620
tcctacaagc tgtgcaggca aaacctagca ggaaaaaaaa acaacgcata agaaaaatg     1680
gccgggccag gtcattggct gggaagtctc agccatgcac ggactcgttt ccagaggtaa    1740
ttatgagcgc ctaccagcca ggccacccag ccgtgggagg aagggggcgt ggcaaggggt    1800
gggcacattg gtgtctgtgc gaaaggaaaa ttgacccgga agttcctgta ataaatgtca    1860
```
caataaaacg aatgaatg                                                      1878

<210> SEQ ID NO 18
<211> LENGTH: 1872
<212> TYPE: DNA
<213> ORGANISM: Mus sp.

<400> SEQUENCE: 18
ctgcagcaag tgacctcggg tcgtggaccg ctgccctgcc cctccgctg ccacctgggg           60 cggcgcgggc ccggtgcccc ggatcgcgcg tagagccggc gcgatgcacg tgcgctcgct         120
gcgcgctgcg gcgccacaca gcttcgtggc gctctgggcg cctctgttct tgctgcgctc         180
cgccctggcc gatttcagcc tggacaacga ggtgcactcc agcttcatcc accggcgcct         240
ccgcagccag gagcggcggg agatgcagcg ggagatcctg tccatcttag ggttgcccca         300
tcgcccgcgc ccgcacctcc agggaaagca taattcggcg cccatgttca tgttggacct         360
gtacaacgcc atggcggtgg aggagagcgg gccggacgga cagggcttct cctaccccta         420
caaggccgtc ttcagtaccc agggcccccc tttagccagc ctgcaggaca gccacttcct         480
cactgacgcc gacatggtca tgagcttcgt caacctagtg gaacatgaca agaattcttt         540
ccaccctcga taccaccatc gggagttccg gtttgatctt tccaagatcc ccgagggcga         600
acgggtgacc gcagccgaat tcaggatcta aaggactac atccgggagc gatttgacaa          660
cgagaccttc cagatcacag tctatcaggt gctccaggag cactcaggca gggagtcgga         720
cctcttcttg ctggacagcc gcaccatctg ggcttctgag gagggctggt tggtgtttga         780
tatcacagcc accagcaacc actgggtggt caaccctcgg cacaacctgg gcttacagct         840
ctctgtggag accctggatg gcagagcat caaccccaag ttggcaggcc tgattggacg          900
gcatggaccc cagaacaagc aacccttcat ggtggccttc ttcaaggcca cggaagtcca         960
tctccgtagt atccggtcca cggggggcaa gcagcgcagc cagaatcgct ccaagacgcc        1020
aaagaaccaa gaggccctga ggatggccag tgtggcagaa acagcagca gtgaccagag         1080 gcaggcctgc aagaaacatg agctgtacgt cagcttccga gaccttggct ggcaggactg        1140
gatcattgca cctgaaggct atgctgccta ctactgtgag ggagagtgcg ccttccctct        1200
gaactcctac atgaacgcca ccaaccacgc catcgtccag acactggttc acttcatcaa        1260
cccagacaca gtacccaagc cctgctgtgc gcccacccag ctcaacgcca tctctgtcct        1320
ctacttcgac gacagctcta atgtcatcct gaagaagtac agaaacatgg tggtccgggc        1380
ctgtggctgc cactagctct tcctgagacc ctgacctttg cggggccaca cctttccaaa        1440
tcttcgatgt ctcaccatct aagtctctca ctgcccacct tggcgaggag ccaacagacc        1500
aacctctcct gagccttccc ctcacctccc aaccggaag catgtaaggg ttccagaaac         1560
ctgagcgtgc aggcagctga tgagcgccct ttccttctgg cacgtgacgg acaagatcct        1620
accagctacc acagcaaacg cctaagagca ggaaaaatgt ctgccaggaa agtgtccatt        1680
ggccacatgg cccctggcgc tctgagtctt tgaggagtaa tcgcaagcct cgttcagctg        1740
cagcagaagg aagggcttag ccagggtggg cgctggcgtc tgtgttgaag ggaaaccaag        1800
cagaagccac tgtaatgata tgtcacaata aacccatga atgaaaaaaa aaaaaaaaaa        1860
aaaaaaaaaa aa                                                             1872

<210> SEQ ID NO 19
<211> LENGTH: 430
<212> TYPE: PRT
<213> ORGANISM: Mus sp.

<400> SEQUENCE: 19

```
Met His Val Arg Ser Leu Arg Ala Ala Pro His Ser Phe Val Ala
1               5                   10                  15

Leu Trp Ala Pro Leu Phe Leu Leu Arg Ser Ala Leu Ala Asp Phe Ser
            20                  25                  30

Leu Asp Asn Glu Val His Ser Ser Phe Ile His Arg Arg Leu Arg Ser
                35                  40                  45

Gln Glu Arg Arg Glu Met Gln Arg Glu Ile Leu Ser Ile Leu Gly Leu
    50                  55                  60

Pro His Arg Pro Arg Pro His Leu Gln Gly Lys His Asn Ser Ala Pro
65                  70                  75                  80

Met Phe Met Leu Asp Leu Tyr Asn Ala Met Ala Val Glu Glu Ser Gly
                85                  90                  95

Pro Asp Gly Gln Gly Phe Ser Tyr Pro Tyr Lys Ala Val Phe Ser Thr
                100                 105                 110

Gln Gly Pro Pro Leu Ala Ser Leu Gln Asp Ser His Phe Leu Thr Asp
            115                 120                 125

Ala Asp Met Val Met Ser Phe Val Asn Leu Val Glu His Asp Lys Glu
130                 135                 140

Phe Phe His Pro Arg Tyr His His Arg Glu Phe Arg Phe Asp Leu Ser
145                 150                 155                 160

Lys Ile Pro Glu Gly Glu Arg Val Thr Ala Ala Glu Phe Arg Ile Tyr
                165                 170                 175

Lys Asp Tyr Ile Arg Glu Arg Phe Asp Asn Glu Thr Phe Gln Ile Thr
            180                 185                 190

Val Tyr Gln Val Leu Gln Glu His Ser Gly Arg Glu Ser Asp Leu Phe
    195                 200                 205

Leu Leu Asp Ser Arg Thr Ile Trp Ala Ser Glu Glu Gly Trp Leu Val
210                 215                 220

Phe Asp Ile Thr Ala Thr Ser Asn His Trp Val Val Asn Pro Arg His
225                 230                 235                 240

Asn Leu Gly Leu Gln Leu Ser Val Glu Thr Leu Asp Gly Gln Ser Ile
                245                 250                 255

Asn Pro Lys Leu Ala Gly Leu Ile Gly Arg His Gly Pro Gln Asn Lys
            260                 265                 270

Gln Pro Phe Met Val Ala Phe Phe Lys Ala Thr Glu Val His Leu Arg
    275                 280                 285

Ser Ile Arg Ser Thr Gly Gly Lys Gln Arg Ser Gln Asn Arg Ser Lys
290                 295                 300

Thr Pro Lys Asn Gln Glu Ala Leu Arg Met Ala Ser Val Ala Glu Asn
305                 310                 315                 320

Ser Ser Ser Asp Gln Arg Gln Ala Cys Lys Lys His Glu Leu Tyr Val
                325                 330                 335

Ser Phe Arg Asp Leu Gly Trp Gln Asp Trp Ile Ile Ala Pro Glu Gly
            340                 345                 350

Tyr Ala Ala Tyr Tyr Cys Glu Gly Glu Cys Ala Phe Pro Leu Asn Ser
    355                 360                 365

Tyr Met Asn Ala Thr Asn His Ala Ile Val Gln Thr Leu Val His Phe
370                 375                 380

Ile Asn Pro Asp Thr Val Pro Lys Pro Cys Cys Ala Pro Thr Gln Leu
385                 390                 395                 400

Asn Ala Ile Ser Val Leu Tyr Phe Asp Asp Ser Ser Asn Val Ile Leu
                405                 410                 415
```

| Lys | Lys | Tyr | Arg | Asn | Met | Val | Val | Arg | Ala | Cys | Gly | Cys | His |
| | | | 420 | | | | 425 | | | | | 430 | |

<210> SEQ ID NO 20
<211> LENGTH: 1842
<212> TYPE: DNA
<213> ORGANISM: Homo sapiens

<400> SEQUENCE: 20

| | | | | | |
|---|---|---|---|---|---|
| ccacagtggc | gccggcagag | caggagtggc | tggaggagct | gtggttggag | caggaggtgg | 60 |
| cacggcaggg | ctggagggct | ccctatgagt | ggcggagacg | gcccaggagg | cgctggagca | 120 |
| acagctccca | caccgcacca | agcggtggct | gcaggagctc | gcccatcgcc | cctgcgctgc | 180 |
| tcggaccgcg | gccacagccg | gactggcggg | tacggcggcg | acagacggat | tggccgagag | 240 |
| tcccagtccg | cagagtagcc | ccggcctcga | ggcggtggcg | tcccggtcct | ctccgtccag | 300 |
| gagccaggac | aggtgtcgcg | cggcggggct | ccagggaccg | cgcctgaggc | cggctgcccg | 360 |
| cccgtcccgc | cccgccccgc | cgcccgccgc | ccgccgagcc | cagcctcctt | gccgtcgggg | 420 |
| cgtccccagg | ccctgggtcg | gccgcggagc | cgatgcgcgc | ccgctgagcg | ccccagctga | 480 |
| gcgccccgg | cctgccatga | ccgcgctccc | cggcccgctc | tggctcctgg | gctggcgct | 540 |
| atgcgcgctg | ggcggggggcg | gccccggcct | gcgaccccg | ccggctgtc | cccagcgacg | 600 |
| tctgggcgcg | cgcgagcgcc | gggacgtgca | gcgcgagatc | ctggcggtgc | tcgggctgcc | 660 |
| tgggcggccc | cggccccgcg | cgccaccgc | cgcctcccgg | ctgcccgcgt | ccgcgccgct | 720 |
| cttcatgctg | gacctgtacc | acgccatggc | cggcgacgac | gacgaggacg | gcgcgcccgc | 780 |
| ggagcggcgc | ctgggccgcg | ccgacctggt | catgagcttc | gttaacatgg | tggagcgaga | 840 |
| ccgtgccctg | ggccaccagg | agccccattg | gaaggagttc | cgctttgacc | tgacccagat | 900 |
| cccggctggg | gaggcggtca | gctgcgcga | gttccggatt | tacaaggtgc | ccagcatcca | 960 |
| cctgctcaac | aggaccctcc | acgtcagcat | gttccaggtg | gtccaggagc | agtccaacag | 1020 |
| ggagtctgac | ttgttctttt | tggatcttca | gacgctccga | gctggagacg | agggctggct | 1080 |
| ggtgctggat | gtcacagcag | ccagtgactg | ctggttgctg | aagcgtcaca | aggacctggg | 1140 |
| actccgcctc | tatgtggaga | ctgaggacgg | gcacagcgtg | gatcctggcc | tggccggcct | 1200 |
| gctgggtcaa | cgggcccac | gctcccaaca | gcctttcgtg | gtcactttct | tcagggccag | 1260 |
| tccgagtccc | atccgcaccc | ctcgggcagt | gaggccactg | aggaggaggc | agccgaagaa | 1320 |
| aagcaacgag | ctgccgcagg | ccaaccgact | cccaggatc | tttgatgacg | tccacggctc | 1380 |
| ccacggccgg | caggtctgcc | gtcggcacga | gctctacgtc | agcttccagg | acctcggctg | 1440 |
| gctggactgg | gtcatcgctc | ccaaggcta | ctcggcctat | tactgtgagg | gggagtgctc | 1500 |
| cttcccactg | gactcctgca | tgaatgccac | caaccacgcc | atcctgcagt | ccctggtgca | 1560 |
| cctgatgaag | ccaaacgcag | tccccaaggc | gtgctgtgca | cccaccaagc | tgagcgccac | 1620 |
| ctctgtgctc | tactatgaca | gcagcaacaa | cgtcatcctg | cgcaagcacc | gcaacatggt | 1680 |
| ggtcaaggcc | tgcggctgcc | actgagtcag | cccgcccagc | cctactgcag | ccacccttct | 1740 |
| catctggatc | gggccctgca | gaggcagaaa | accccttaaat | gctgtcacag | ctcaagcagg | 1800 |
| agtgtcaggg | gccctcactc | tctgtgccta | cttcctgtca | gg | | 1842 |

<210> SEQ ID NO 21
<211> LENGTH: 402
<212> TYPE: PRT
<213> ORGANISM: Homo sapiens

<400> SEQUENCE: 21

```
Met Thr Ala Leu Pro Gly Pro Leu Trp Leu Leu Gly Leu Ala Leu Cys
1               5                   10                  15

Ala Leu Gly Gly Gly Pro Gly Leu Arg Pro Pro Gly Cys Pro
            20                  25                  30

Gln Arg Arg Leu Gly Ala Arg Glu Arg Arg Asp Val Gln Arg Glu Ile
        35                  40                  45

Leu Ala Val Leu Gly Leu Pro Gly Arg Pro Arg Pro Arg Ala Pro Pro
        50                  55                  60

Ala Ala Ser Arg Leu Pro Ala Ser Ala Pro Leu Phe Met Leu Asp Leu
65                  70                  75                  80

Tyr His Ala Met Ala Gly Asp Asp Glu Asp Gly Ala Pro Ala Glu
            85                  90                  95

Arg Arg Leu Gly Arg Ala Asp Leu Val Met Ser Phe Val Asn Met Val
            100                 105                 110

Glu Arg Asp Arg Ala Leu Gly His Gln Glu Pro His Trp Lys Glu Phe
            115                 120                 125

Arg Phe Asp Leu Thr Gln Ile Pro Ala Gly Glu Ala Val Thr Ala Ala
            130                 135                 140

Glu Phe Arg Ile Tyr Lys Val Pro Ser Ile His Leu Leu Asn Arg Thr
145                 150                 155                 160

Leu His Val Ser Met Phe Gln Val Val Gln Glu Gln Ser Asn Arg Glu
            165                 170                 175

Ser Asp Leu Phe Phe Leu Asp Leu Gln Thr Leu Arg Ala Gly Asp Glu
            180                 185                 190

Gly Trp Leu Val Leu Asp Val Thr Ala Ala Ser Asp Cys Trp Leu Leu
            195                 200                 205

Lys Arg His Lys Asp Leu Gly Leu Arg Leu Tyr Val Glu Thr Glu Asp
210                 215                 220

Gly His Ser Val Asp Pro Gly Leu Ala Gly Leu Leu Gly Gln Arg Ala
225                 230                 235                 240

Pro Arg Ser Gln Gln Pro Phe Val Val Thr Phe Phe Arg Ala Ser Pro
            245                 250                 255

Ser Pro Ile Arg Thr Pro Arg Ala Val Arg Pro Leu Arg Arg Arg Gln
            260                 265                 270

Pro Lys Lys Ser Asn Glu Leu Pro Gln Ala Asn Arg Leu Pro Gly Ile
            275                 280                 285

Phe Asp Asp Val His Gly Ser His Gly Arg Gln Val Cys Arg Arg His
            290                 295                 300

Glu Leu Tyr Val Ser Phe Gln Asp Leu Gly Trp Leu Asp Trp Val Ile
305                 310                 315                 320

Ala Pro Gln Gly Tyr Ser Ala Tyr Tyr Cys Glu Gly Glu Cys Ser Phe
            325                 330                 335

Pro Leu Asp Ser Cys Met Asn Ala Thr Asn His Ala Ile Leu Gln Ser
            340                 345                 350

Leu Val His Leu Met Lys Pro Asn Ala Val Pro Lys Ala Cys Cys Ala
            355                 360                 365

Pro Thr Lys Leu Ser Ala Thr Ser Val Leu Tyr Tyr Asp Ser Ser Asn
            370                 375                 380

Asn Val Ile Leu Arg Lys His Arg Asn Met Val Val Lys Ala Cys Gly
385                 390                 395                 400

Cys His

<210> SEQ ID NO 22
```

<211> LENGTH: 1917
<212> TYPE: DNA
<213> ORGANISM: Mus sp.

<400> SEQUENCE: 22

```
gccaggcaca ggtgcgccgt ctggtcctcc ccgtctggcg tcagccgagc ccgaccagct      60
accagtggat gcgcgccggc tgaaagtccg agatggctat gcgtcccggg ccactctggc     120
tattgggcct tgctctgtgc gcgctgggag gcggccacgg tccgcgtccc cgcacacct      180
gtccccagcg tcgcctggga gcgcgcgagc gccgcgacat gcagcgtgaa atcctggcgg     240
tgctcgggct accgggacgg ccccgacccc gtgcacaacc cgccgctgcc cggcagccag     300
cgtccgcgcc cctcttcatg ttggacctat accacgccat gaccgatgac gacgacggcg     360
ggccaccaca ggctcactta ggccgtgccg acctggtcat gagcttcgtc aacatggtgg     420
aacgcgaccg taccctgggc taccaggagc acactggaa ggaattccac tttgacctaa      480
cccagatccc tgctggggag ctgtcacag ctgctgagtt ccggatctac aaagaaccca      540
gcacccaccc gctcaacaca accctccaca tcagcatgtt cgaagtggtc caagagcact     600
ccaacaggga gtctgacttg ttctttttgg atcttcagac gctccgatct ggggacgagg     660
gctggctggt gctggacatc acagcagcca gtgaccgatg gctgctgaac catcacaagg     720
acctgggact ccgcctctat gtggaaaccg cggatgggca cagcatggat cctgcctgg     780
ctggtctgct tggacgacaa gcaccacgct ccagacagcc tttcatggta accttcttca     840
gggccagcca gagtcctgtg cgggcccctc gggcagcgag accactgaag gaggaggcagc    900
caaagaaaac gaacgagctt ccgcaccca acaaactccc agggatcttt gatgatggcc      960
acggttccg cggcagagag gtttgccgca ggcatgagct ctacgtcagc ttccgtgacc     1020
ttggctggct ggactgggtc atcgccccc agggctactc tgcctattac tgtgaggggg     1080
agtgtgcttt cccactggac tcctgtatga acgccaccaa ccatgccatc ttgcagtctc     1140
tggtgcacct gatgaagcca gatgttgtcc ccaaggcatg ctgtgcaccc accaaactga     1200
gtgccacctc tgtgctgtac tatgacagca gcaacaatgt catcctgcgt aaacaccgta     1260
acatggtggt caaggcctgt ggctgccact gaggcccccgc ccagcatcct gcttctacta     1320
ccttaccatc tggccgggcc cctctccaga ggcagaaacc cttctatgtt atcatagctc     1380
agacaggggc aatgggaggc ccttcacttc ccctggccac ttcctgctaa aattctggtc     1440
tttcccagtt cctctgtcct tcatggggtt tcggggctat caccccgccc tctccatcct     1500
cctaccccaa gcatagactg aatgcacaca gcatcccaga gctatgctaa ctgagaggtc     1560
tggggtcagc actgaaggcc cacatgagga agactgatcc ttggccatcc tcagcccaca     1620
atggcaaatt ctgatggtc taagaagccc tggaattcta aactagatga tctgggctct     1680
ctgcaccatt cattgtggca gttgggacat tttaggtat aacagacaca tacacttaga     1740
tcaatgcatc gctgtactcc ttgaaatcag agctagcttt ttagaaaaag aatcagagcc     1800
aggtatagcg gtgcatgtca ttaatcccag cgctaaagag acagagacag gagaatctct     1860
gtgagttcaa ggccacatag aaagagcctg tctcgggagc aggaaaaaaa aaaaaaa       1917
```

<210> SEQ ID NO 23
<211> LENGTH: 399
<212> TYPE: PRT
<213> ORGANISM: Mus sp.

<400> SEQUENCE: 23

```
Met Ala Met Arg Pro Gly Pro Leu Trp Leu Leu Gly Leu Ala Leu Cys
1               5                   10                  15
```

Ala Leu Gly Gly Gly His Gly Pro Arg Pro His Thr Cys Pro Gln
            20                  25                  30

Arg Arg Leu Gly Ala Arg Glu Arg Asp Met Gln Arg Glu Ile Leu
        35                  40                  45

Ala Val Leu Gly Leu Pro Gly Arg Pro Arg Pro Ala Gln Pro Ala
50                  55                  60

Ala Ala Arg Gln Pro Ala Ser Ala Pro Leu Phe Met Leu Asp Leu Tyr
65                  70                  75                  80

His Ala Met Thr Asp Asp Asp Gly Gly Pro Pro Gln Ala His Leu
                85                  90                  95

Gly Arg Ala Asp Leu Val Met Ser Phe Val Asn Met Val Glu Arg Asp
                100                 105                 110

Arg Thr Leu Gly Tyr Gln Glu Pro His Trp Lys Glu Phe His Phe Asp
            115                 120                 125

Leu Thr Gln Ile Pro Ala Gly Glu Ala Val Thr Ala Ala Glu Phe Arg
130                 135                 140

Ile Tyr Lys Glu Pro Ser Thr His Pro Leu Asn Thr Thr Leu His Ile
145                 150                 155                 160

Ser Met Phe Glu Val Val Gln Glu His Ser Asn Arg Glu Ser Asp Leu
                165                 170                 175

Phe Phe Leu Asp Leu Gln Thr Leu Arg Ser Gly Asp Glu Gly Trp Leu
            180                 185                 190

Val Leu Asp Ile Thr Ala Ala Ser Asp Arg Trp Leu Leu Asn His His
                195                 200                 205

Lys Asp Leu Gly Leu Arg Leu Tyr Val Glu Thr Ala Asp Gly His Ser
210                 215                 220

Met Asp Pro Gly Leu Ala Gly Leu Leu Gly Arg Gln Ala Pro Arg Ser
225                 230                 235                 240

Arg Gln Pro Phe Met Val Thr Phe Phe Arg Ala Ser Gln Ser Pro Val
                245                 250                 255

Arg Ala Pro Arg Ala Ala Arg Pro Leu Lys Arg Arg Gln Pro Lys Lys
            260                 265                 270

Thr Asn Glu Leu Pro His Pro Asn Lys Leu Pro Gly Ile Phe Asp Asp
                275                 280                 285

Gly His Gly Ser Arg Gly Arg Glu Val Cys Arg Arg His Glu Leu Tyr
290                 295                 300

Val Ser Phe Arg Asp Leu Gly Trp Leu Asp Trp Val Ile Ala Pro Gln
305                 310                 315                 320

Gly Tyr Ser Ala Tyr Tyr Cys Glu Gly Glu Cys Ala Phe Pro Leu Asp
                325                 330                 335

Ser Cys Met Asn Ala Thr Asn His Ala Ile Leu Gln Ser Leu Val His
            340                 345                 350

Leu Met Lys Pro Asp Val Val Pro Lys Ala Cys Cys Ala Pro Thr Lys
            355                 360                 365

Leu Ser Ala Thr Ser Val Leu Tyr Tyr Asp Ser Ser Asn Asn Val Ile
            370                 375                 380

Leu Arg Lys His Arg Asn Met Val Val Lys Ala Cys Gly Cys His
385                 390                 395

<210> SEQ ID NO 24
<211> LENGTH: 97
<212> TYPE: PRT
<213> ORGANISM: Artificial Sequence
<220> FEATURE:
<221> NAME/KEY: source -continued

```
<223> OTHER INFORMATION: /note="Description of Artificial Sequence:
      Synthetic peptide"
<220> FEATURE:
<221> NAME/KEY: VARIANT
<222> LOCATION: (6)..(6)
<223> OTHER INFORMATION: /replace="Gln"
<220> FEATURE:
<221> NAME/KEY: misc_feature
<222> LOCATION: (6)..(6)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (8)..(8)
<223> OTHER INFORMATION: /replace="Val"
<220> FEATURE:
<221> NAME/KEY: misc_feature
<222> LOCATION: (8)..(8)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (18)..(18)
<223> OTHER INFORMATION: /replace="Lys"
<220> FEATURE:
<221> NAME/KEY: misc_feature
<222> LOCATION: (18)..(18)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (23)..(23)
<223> OTHER INFORMATION: /replace="Asn" or "Phe"
<220> FEATURE:
<221> NAME/KEY: misc_feature
<222> LOCATION: (23)..(23)
<223> OTHER INFORMATION: /note="Residue given in the sequence has no
      preference with respect to those in the annotation for said
      position"
<220> FEATURE:
<221> NAME/KEY: VARIANT
<222> LOCATION: (26)..(26)
<223> OTHER INFORMATION: /replace="Asp"
<220> FEATURE:
<221> NAME/KEY: misc_feature
<222> LOCATION: (26)..(26)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (30)..(30)
<223> OTHER INFORMATION: /replace="Ser"
<220> FEATURE:
<221> NAME/KEY: misc_feature
<222> LOCATION: (30)..(30)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (31)..(31)
<223> OTHER INFORMATION: /replace="Leu" or "Tyr"
<220> FEATURE:
<221> NAME/KEY: misc_feature
<222> LOCATION: (31)..(31)
<223> OTHER INFORMATION: /note="Residue given in the sequence has no
      preference with respect to those in the annotation for said
      position"
<220> FEATURE:
<221> NAME/KEY: VARIANT
<222> LOCATION: (33)..(33)
<223> OTHER INFORMATION: /replace="Val" or "Met"
<220> FEATURE:
<221> NAME/KEY: misc_feature
<222> LOCATION: (33)..(33)
<223> OTHER INFORMATION: /note="Residue given in the sequence has no
```

```
      preference with respect to those in the annotation for said
      position"
<220> FEATURE:
<221> NAME/KEY: VARIANT
<222> LOCATION: (34)..(34)
<223> OTHER INFORMATION: /replace="Asp" or "Ala" or "Thr" or "Pro"
<220> FEATURE:
<221> NAME/KEY: misc_feature
<222> LOCATION: (34)..(34)
<223> OTHER INFORMATION: /note="Residue given in the sequence has no
      preference with respect to those in the annotation for said
      position"
<220> FEATURE:
<221> NAME/KEY: VARIANT
<222> LOCATION: (35)..(35)
<223> OTHER INFORMATION: /replace="Ala"
<220> FEATURE:
<221> NAME/KEY: misc_feature
<222> LOCATION: (35)..(35)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (36)..(36)
<223> OTHER INFORMATION: /replace="His"
<220> FEATURE:
<221> NAME/KEY: misc_feature
<222> LOCATION: (36)..(36)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (51)..(51)
<223> OTHER INFORMATION: /replace="Leu" or "Val"
<220> FEATURE:
<221> NAME/KEY: misc_feature
<222> LOCATION: (51)..(51)
<223> OTHER INFORMATION: /note="Residue given in the sequence has no
      preference with respect to those in the annotation for said
      position"
<220> FEATURE:
<221> NAME/KEY: VARIANT
<222> LOCATION: (52)..(52)
<223> OTHER INFORMATION: /replace="Met"
<220> FEATURE:
<221> NAME/KEY: misc_feature
<222> LOCATION: (52)..(52)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (53)..(53)
<223> OTHER INFORMATION: /replace="Phe"
<220> FEATURE:
<221> NAME/KEY: misc_feature
<222> LOCATION: (53)..(53)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (55)..(55)
<223> OTHER INFORMATION: /replace="Asp"
<220> FEATURE:
<221> NAME/KEY: misc_feature
<222> LOCATION: (55)
<223> OTHER INFORMATION: /note="Residue given in the sequence has no
      preference with respect to the residue in the annotation for said
      position"
<220> FEATURE:
<221> NAME/KEY: MOD_RES
<222> LOCATION: (56)..(56)
<223> OTHER INFORMATION: Any amino acid
<220> FEATURE:
<221> NAME/KEY: VARIANT
<222> LOCATION: (66)..(66)
<223> OTHER INFORMATION: /replace="Lys"
```

```
<220> FEATURE:
<221> NAME/KEY: misc_feature
<222> LOCATION: (66)..(66)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (67)..(67)
<223> OTHER INFORMATION: /replace="Val"
<220> FEATURE:
<221> NAME/KEY: misc_feature
<222> LOCATION: (67)..(67)
<223> OTHER INFORMATION: /note="Residue given in the sequence has no
      preference with respect to the residue in the annotation for said
      position"
<220> FEATURE:
<221> NAME/KEY: MOD_RES
<222> LOCATION: (78)..(78)
<223> OTHER INFORMATION: Any amino acid
<220> FEATURE:
<221> NAME/KEY: VARIANT
<222> LOCATION: (88)..(88)
<223> OTHER INFORMATION: /replace="Trp"
<220> FEATURE:
<221> NAME/KEY: misc_feature
<222> LOCATION: (88)..(88)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (90)..(90)
<223> OTHER INFORMATION: /replace="Thr" or "Ala" or "Ile"
<220> FEATURE:
<221> NAME/KEY: misc_feature
<222> LOCATION: (90)..(90)
<223> OTHER INFORMATION: /note="Residue given in the sequence has no
      preference with respect to those in the annotation for said
      position"
<220> FEATURE:
<221> NAME/KEY: VARIANT
<222> LOCATION: (92)..(92)
<223> OTHER INFORMATION: /replace="Lys" or "Val" or "Asp" or "Gln" or
      "Glu"
<220> FEATURE:
<221> NAME/KEY: misc_feature
<222> LOCATION: (92)..(92)
<223> OTHER INFORMATION: /note="Residue given in the sequence has no
      preference with respect to those in the annotation for said
      position"
<220> FEATURE:
<221> NAME/KEY: VARIANT
<222> LOCATION: (93)..(93)
<223> OTHER INFORMATION: /replace="Ser"
<220> FEATURE:
<221> NAME/KEY: misc_feature
<222> LOCATION: (93)..(93)
<223> OTHER INFORMATION: /note="Residue given in the sequence has no
      preference with respect to the residue in the annotation for said
      position"

<400> SEQUENCE: 24

Leu Tyr Val Ser Phe Arg Asp Leu Gly Trp Gln Asp Trp Ile Ile Ala
1               5                   10                  15

Pro Glu Gly Tyr Ala Ala Tyr Tyr Cys Glu Gly Glu Cys Ala Phe Pro
                20                  25                  30

Leu Asn Ser Tyr Met Asn Ala Thr Asn His Ala Ile Val Gln Thr Leu
            35                  40                  45

Val His Phe Ile Asn Pro Glu Xaa Val Pro Lys Pro Cys Cys Ala Pro
        50                  55                  60

Thr Gln Leu Asn Ala Ile Ser Val Leu Tyr Phe Asp Asp Xaa Ser Asn
65                  70                  75                  80

Val Ile Leu Lys Lys Tyr Arg Asn Met Val Val Arg Ala Cys Gly Cys
```

-continued

```
                85                  90                  95
His

<210> SEQ ID NO 25
<211> LENGTH: 101
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic polypeptide"
<220> FEATURE:
<221> NAME/KEY: VARIANT
<222> LOCATION: (2)..(2)
<223> OTHER INFORMATION: /replace="Arg"
<220> FEATURE:
<221> NAME/KEY: misc_feature
<222> LOCATION: (2)..(2)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (3)..(3)
<223> OTHER INFORMATION: /replace="Arg"
<220> FEATURE:
<221> NAME/KEY: misc_feature
<222> LOCATION: (3)..(3)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (11)..(11)
<223> OTHER INFORMATION: /replace="Gln"
<220> FEATURE:
<221> NAME/KEY: misc_feature
<222> LOCATION: (11)..(11)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (16)..(16)
<223> OTHER INFORMATION: /replace="Leu"
<220> FEATURE:
<221> NAME/KEY: misc_feature
<222> LOCATION: (16)..(16)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (19)..(19)
<223> OTHER INFORMATION: /replace="Val"
<220> FEATURE:
<221> NAME/KEY: misc_feature
<222> LOCATION: (19)..(19)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (23)..(23)
<223> OTHER INFORMATION: /replace="Gln"
<220> FEATURE:
<221> NAME/KEY: misc_feature
<222> LOCATION: (23)..(23)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (26)..(26)
<223> OTHER INFORMATION: /replace="Ser"
<220> FEATURE:
<221> NAME/KEY: misc_feature
<222> LOCATION: (26)..(26)
```

```
<223> OTHER INFORMATION: /note="Residue given in the sequence has no
      preference with respect to the residue in the annotation for said
      position"
<220> FEATURE:
<221> NAME/KEY: VARIANT
<222> LOCATION: (35)..(35)
<223> OTHER INFORMATION: /replace="Ser"
<220> FEATURE:
<221> NAME/KEY: misc_feature
<222> LOCATION: (35)..(35)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (39)..(39)
<223> OTHER INFORMATION: /replace="Asp"
<220> FEATURE:
<221> NAME/KEY: misc_feature
<222> LOCATION: (39)..(39)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (41)..(41)
<223> OTHER INFORMATION: /replace="Cys"
<220> FEATURE:
<221> NAME/KEY: misc_feature
<222> LOCATION: (41)..(41)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (50)..(50)
<223> OTHER INFORMATION: /replace="Leu"
<220> FEATURE:
<221> NAME/KEY: misc_feature
<222> LOCATION: (50)..(50)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (52)..(52)
<223> OTHER INFORMATION: /replace="Thr"
<220> FEATURE:
<221> NAME/KEY: misc_feature
<222> LOCATION: (52)..(52)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (56)..(56)
<223> OTHER INFORMATION: /replace="Leu"
<220> FEATURE:
<221> NAME/KEY: misc_feature
<222> LOCATION: (56)..(56)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (57)..(57)
<223> OTHER INFORMATION: /replace="Met"
<220> FEATURE:
<221> NAME/KEY: misc_feature
<222> LOCATION: (57)..(57)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (58)..(58)
<223> OTHER INFORMATION: /replace="Lys"
<220> FEATURE:
<221> NAME/KEY: misc_feature
<222> LOCATION: (58)..(58)
```

```
<223> OTHER INFORMATION: /note="Residue given in the sequence has no
      preference with respect to the residue in the annotation for said
      position"
<220> FEATURE:
<221> NAME/KEY: VARIANT
<222> LOCATION: (60)..(60)
<223> OTHER INFORMATION: /replace="Asp" or "Asn"
<220> FEATURE:
<221> NAME/KEY: misc_feature
<222> LOCATION: (60)..(60)
<223> OTHER INFORMATION: /note="Residue given in the sequence has no
      preference with respect to those in the annotation for said
      position"
<220> FEATURE:
<221> NAME/KEY: VARIANT
<222> LOCATION: (61)..(61)
<223> OTHER INFORMATION: /replace="Ala" or "Val"
<220> FEATURE:
<221> NAME/KEY: misc_feature
<222> LOCATION: (61)..(61)
<223> OTHER INFORMATION: /note="Residue given in the sequence has no
      preference with respect to those in the annotation for said
      position"
<220> FEATURE:
<221> NAME/KEY: VARIANT
<222> LOCATION: (65)..(65)
<223> OTHER INFORMATION: /replace="Ala"
<220> FEATURE:
<221> NAME/KEY: misc_feature
<222> LOCATION: (65)..(65)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (71)..(71)
<223> OTHER INFORMATION: /replace="Lys"
<220> FEATURE:
<221> NAME/KEY: misc_feature
<222> LOCATION: (71)..(71)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (73)..(73)
<223> OTHER INFORMATION: /replace="Ser"
<220> FEATURE:
<221> NAME/KEY: misc_feature
<222> LOCATION: (73)..(73)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (75)..(75)
<223> OTHER INFORMATION: /replace="Thr"
<220> FEATURE:
<221> NAME/KEY: misc_feature
<222> LOCATION: (75)..(75)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (80)..(80)
<223> OTHER INFORMATION: /replace="Tyr"
<220> FEATURE:
<221> NAME/KEY: misc_feature
<222> LOCATION: (80)..(80)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (82)..(82)
<223> OTHER INFORMATION: /replace="Ser"
<220> FEATURE:
<221> NAME/KEY: misc_feature
<222> LOCATION: (82)..(82)
```

```
<223> OTHER INFORMATION: /note="Residue given in the sequence has no
      preference with respect to the residue in the annotation for said
      position"
<220> FEATURE:
<221> NAME/KEY: VARIANT
<222> LOCATION: (84)..(84)
<223> OTHER INFORMATION: /replace="Asn"
<220> FEATURE:
<221> NAME/KEY: misc_feature
<222> LOCATION: (84)..(84)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (89)..(89)
<223> OTHER INFORMATION: /replace="Arg"
<220> FEATURE:
<221> NAME/KEY: misc_feature
<222> LOCATION: (89)..(89)
<223> OTHER INFORMATION: /note="Residue given in the sequence has no
      preference with respect to the residue in the annotation for said
      position"
<220> FEATURE:
<221> NAME/KEY: VARIANT
<222> LOCATION: (91)..(91)
<223> OTHER INFORMATION: /replace="His"
<220> FEATURE:
<221> NAME/KEY: misc_feature
<222> LOCATION: (91)..(91)
<223> OTHER INFORMATION: /note="Residue given in the sequence has no
      preference with respect to the residue in the annotation for said
      position"
<220> FEATURE:
<221> NAME/KEY: MOD_RES
<222> LOCATION: (96)..(96)
<223> OTHER INFORMATION: /replace="Lys"
<220> FEATURE:
<221> NAME/KEY: misc_feature
<222> LOCATION: (96)..(96)
<223> OTHER INFORMATION: /note="Residue given in the sequence has no
      preference with respect to the residue in the annotation for said
      position"

<400> SEQUENCE: 25

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
            20                  25                  30

Glu Cys Ala Phe Pro Leu Asn Ser Tyr Met Asn Ala Thr Asn His Ala
        35                  40                  45

Ile Val Gln Ser Leu Val His Phe Ile Asn Pro Glu Thr Val Pro Lys
    50                  55                  60

Pro Cys Cys Ala Pro Thr Gln Leu Asn Ala Ile Ser Val Leu Tyr Phe
65                  70                  75                  80

Asp Asp Ser Ser Asn Val Ile Leu Lys Lys Tyr Arg Asn Met Val Arg
                85                  90                  95

Ala Cys Gly Cys His
            100

<210> SEQ ID NO 26
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 26
gagaggtcca ttccaactgc tcagatgaag                                    30
```

```
<210> SEQ ID NO 27
<211> LENGTH: 30
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 27
gtcttcactt cgagtctgat ccggagaaag                                        30

<210> SEQ ID NO 28
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 28
agcatgtcct ctgctcactt caacc                                             25

<210> SEQ ID NO 29
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 29
cgtccatgaa gttgttgccg at                                                22

<210> SEQ ID NO 30
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 30
tgggtggtga tccactggat c                                                 21

<210> SEQ ID NO 31
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 31
ttgccttgag tcagtgcgcc                                                   20

<210> SEQ ID NO 32
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"
```

-continued

<400> SEQUENCE: 32
agcccagcca agcactgtca                                           20

<210> SEQ ID NO 33
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 33
gagcatcgtc cccagcaaag                                           20

<210> SEQ ID NO 34
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 34
gaagatcgtc gacatgtaca aggg                                      24

<210> SEQ ID NO 35
<211> LENGTH: 23
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 35
tgcatagaat ggactggtcc tcc                                       23

<210> SEQ ID NO 36
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 36
gctacacaag accctgagac tgacc                                     25

<210> SEQ ID NO 37
<211> LENGTH: 22
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 37
tctccatctc tgctgagggg at                                        22

<210> SEQ ID NO 38
<211> LENGTH: 20
<212> TYPE: DNA
<213> ORGANISM: Artificial Sequence

```
<220> FEATURE:
<221> NAME/KEY: source
<223> OTHER INFORMATION: /note="Description of Artificial Sequence:
      Synthetic primer"

<400> SEQUENCE: 38
cacgacaacc gcaccatggt                                                      20

<210> SEQ ID NO 39
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 39
tgacagtaac cacagtccca tctg                                                 24

<210> SEQ ID NO 40
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 40
gctggtgaag cccttcgaga                                                      20

<210> SEQ ID NO 41
<211> LENGTH: 19
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 41
atgtggtaaa gggcgtgcg                                                       19

<210> SEQ ID NO 42
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 42
agttcatggc tccagtcccc                                                      20

<210> SEQ ID NO 43
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 43
tggaggctga aaggtcactg c                                                    21
```

```
<210> SEQ ID NO 44
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 44
agccaacact gtgcgcagct                                                   20

<210> SEQ ID NO 45
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 45
cctgaagctc tgctgaggtg ataa                                              24

<210> SEQ ID NO 46
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 46
atgagagccc tcacactcct c                                                 21

<210> SEQ ID NO 47
<211> LENGTH: 21
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 47
gccgtagaag cgccgatagg c                                                 21

<210> SEQ ID NO 48
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 48
tcctgttcga cagtcagccg                                                   20

<210> SEQ ID NO 49
<211> LENGTH: 20
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 49
```

```
tggtgaccag gcgcccaata                                          20

<210> SEQ ID NO 50
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 50
tcccttctca agcaccaatg gact                                     24

<210> SEQ ID NO 51
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 51
agctgtgaat gggcttcttc ctca                                     24

<210> SEQ ID NO 52
<211> LENGTH: 24
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 52
tgttccagta tgactccact cacg                                     24

<210> SEQ ID NO 53
<211> LENGTH: 25
<212> TYPE: DNA
<213> ORGANISM: Artificial Sequence
<220> FEATURE:
<221> NAME/KEY: source
<223> OTHER INFORMATION: /note="Description of Artificial Sequence:
      Synthetic primer"

<400> SEQUENCE: 53
gaagacacca gtagactcca cgaca                                    25

<210> SEQ ID NO 54
<211> LENGTH: 102
<212> TYPE: PRT
<213> ORGANISM: Homo sapiens

<400> SEQUENCE: 54

Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
            20                  25                  30

Glu Cys Ala Phe Pro Leu Asn Ser Tyr Met Asn Ala Thr Asn His Ala
        35                  40                  45

Ile Val Gln Thr Leu Val His Phe Ile Asn Pro Glu Thr Val Pro Lys
    50                  55                  60

Pro Cys Cys Ala Pro Thr Gln Leu Asn Ala Ile Ser Val Leu Tyr Phe
```

```
                 65                  70                  75                  80
Asp Asp Ser Ser Asn Val Ile Leu Lys Lys Tyr Arg Asn Met Val Val
                 85                  90                  95
Arg Ala Cys Gly Cys His
            100
```

<210> SEQ ID NO 55
<211> LENGTH: 102
<212> TYPE: PRT
<213> ORGANISM: Mus sp.

<400> SEQUENCE: 55

```
Cys Lys Lys His Glu Leu Tyr Val Ser Phe Arg Asp Leu Gly Trp Gln
  1               5                  10                  15
Asp Trp Ile Ile Ala Pro Glu Gly Tyr Ala Ala Tyr Tyr Cys Glu Gly
                 20                  25                  30
Glu Cys Ala Phe Pro Leu Asn Ser Tyr Met Asn Ala Thr Asn His Ala
             35                  40                  45
Ile Val Gln Thr Leu Val His Phe Ile Asn Pro Asp Thr Val Pro Lys
         50                  55                  60
Pro Cys Cys Ala Pro Thr Gln Leu Asn Ala Ile Ser Val Leu Tyr Phe
 65                  70                  75                  80
Asp Asp Ser Ser Asn Val Ile Leu Lys Lys Tyr Arg Asn Met Val Val
                 85                  90                  95
Arg Ala Cys Gly Cys His
            100
```

<210> SEQ ID NO 56
<211> LENGTH: 102
<212> TYPE: PRT
<213> ORGANISM: Homo sapiens

<400> SEQUENCE: 56

```
Cys Lys Lys His Glu Leu Tyr Val Ser Phe Arg Asp Leu Gly Trp Gln
  1               5                  10                  15
Asp Trp Ile Ile Ala Pro Glu Gly Tyr Ala Ala Phe Tyr Cys Asp Gly
                 20                  25                  30
Glu Cys Ser Phe Pro Leu Asn Ala His Met Asn Ala Thr Asn His Ala
             35                  40                  45
Ile Val Gln Thr Leu Val His Leu Met Phe Pro Asp His Val Pro Lys
         50                  55                  60
Pro Cys Cys Ala Pro Thr Lys Leu Asn Ala Ile Ser Val Leu Tyr Phe
 65                  70                  75                  80
Asp Asp Ser Ser Asn Val Ile Leu Lys Lys Tyr Arg Asn Met Val Val
                 85                  90                  95
Arg Ser Cys Gly Cys His
            100
```

<210> SEQ ID NO 57
<211> LENGTH: 102
<212> TYPE: PRT
<213> ORGANISM: Homo sapiens

<400> SEQUENCE: 57

```
Cys Arg Lys His Glu Leu Tyr Val Ser Phe Gln Asp Leu Gly Trp Gln
  1               5                  10                  15
Asp Trp Ile Ile Ala Pro Lys Gly Tyr Ala Ala Asn Tyr Cys Asp Gly
                 20                  25                  30
```

-continued

Glu Cys Ser Phe Pro Leu Asn Ala His Met Asn Ala Thr Asn His Ala
            35                  40                  45

Ile Val Gln Thr Leu Val His Leu Met Asn Pro Glu Tyr Val Pro Lys
 50                  55                  60

Pro Cys Cys Ala Pro Thr Lys Leu Asn Ala Ile Ser Val Leu Tyr Phe
 65                  70                  75                  80

Asp Asp Asn Ser Asn Val Ile Leu Lys Lys Tyr Arg Trp Met Val Val
            85                  90                  95

Arg Ala Cys Gly Cys His
            100

<210> SEQ ID NO 58
<211> LENGTH: 102
<212> TYPE: PRT
<213> ORGANISM: Mus sp.

<400> SEQUENCE: 58

Cys Lys Lys His Gly Leu Tyr Val Ser Phe Gln Asp Val Gly Trp Gln
 1               5                  10                  15

Asp Trp Ile Ile Ala Pro Lys Gly Tyr Ala Ala Asn Tyr Cys Asp Gly
            20                  25                  30

Glu Cys Ser Phe Pro Leu Asn Ala His Met Asn Ala Thr Asn His Ala
            35                  40                  45

Ile Val Gln Thr Leu Val His Val Met Asn Pro Glu Tyr Val Pro Lys
 50                  55                  60

Pro Cys Cys Ala Pro Thr Lys Val Asn Ala Ile Ser Val Leu Tyr Phe
 65                  70                  75                  80

Asp Asp Asn Ser Asn Val Ile Leu Lys Lys Tyr Arg Asn Met Val Val
            85                  90                  95

Arg Ala Cys Gly Cys His
            100

<210> SEQ ID NO 59
<211> LENGTH: 102
<212> TYPE: PRT
<213> ORGANISM: Homo sapiens

<400> SEQUENCE: 59

Cys Arg Arg His Glu Leu Tyr Val Ser Phe Gln Asp Leu Gly Trp Leu
 1               5                  10                  15

Asp Trp Val Ile Ala Pro Gln Gly Tyr Ser Ala Tyr Tyr Cys Glu Gly
            20                  25                  30

Glu Cys Ser Phe Pro Leu Asp Ser Cys Met Asn Ala Thr Asn His Ala
            35                  40                  45

Ile Leu Gln Ser Leu Val His Leu Met Lys Pro Asn Ala Val Pro Lys
 50                  55                  60

Ala Cys Cys Ala Pro Thr Lys Leu Ser Ala Thr Ser Val Leu Tyr Tyr
 65                  70                  75                  80

Asp Ser Ser Asn Asn Val Ile Leu Arg Lys His Arg Asn Met Val Val
            85                  90                  95

Lys Ala Cys Gly Cys His
            100

<210> SEQ ID NO 60
<211> LENGTH: 102
<212> TYPE: PRT
<213> ORGANISM: Mus sp.

<400> SEQUENCE: 60

```
Cys Arg Arg His Glu Leu Tyr Val Ser Phe Arg Asp Leu Gly Trp Leu
1               5                   10                  15

Asp Trp Val Ile Ala Pro Gln Gly Tyr Ser Ala Tyr Tyr Cys Glu Gly
            20                  25                  30

Glu Cys Ala Phe Pro Leu Asp Ser Cys Met Asn Ala Thr Asn His Ala
        35                  40                  45

Ile Leu Gln Ser Leu Val His Leu Met Lys Pro Asp Val Val Pro Lys
50                  55                  60

Ala Cys Cys Ala Pro Thr Lys Leu Ser Ala Thr Ser Val Leu Tyr Tyr
65                  70                  75                  80

Asp Ser Ser Asn Asn Val Ile Leu Arg Lys His Arg Asn Met Val Val
                85                  90                  95

Lys Ala Cys Gly Cys His
            100

<210> SEQ ID NO 61
<211> LENGTH: 102
<212> TYPE: PRT
<213> ORGANISM: Drosophila sp.

<400> SEQUENCE: 61

Cys Arg Arg His Ser Leu Tyr Val Asp Phe Ser Asp Val Gly Trp Asp
1               5                   10                  15

Asp Trp Ile Val Ala Pro Leu Gly Tyr Asp Ala Tyr Tyr Cys His Gly
            20                  25                  30

Lys Cys Pro Phe Pro Leu Ala Asp His Phe Asn Ser Thr Asn His Ala
        35                  40                  45

Val Val Gln Thr Leu Val Asn Asn Asn Pro Gly Lys Val Pro Lys
50                  55                  60

Ala Cys Cys Val Pro Thr Gln Leu Asn Ser Val Ala Met Leu Tyr Leu
65                  70                  75                  80

Asn Asp Gln Ser Thr Val Val Leu Lys Asn Tyr Gln Glu Met Thr Val
                85                  90                  95

Val Gly Cys Gly Cys Arg
            100

<210> SEQ ID NO 62
<211> LENGTH: 101
<212> TYPE: PRT
<213> ORGANISM: Homo sapiens

<400> SEQUENCE: 62

Cys Lys Arg His Pro Leu Tyr Val Asp Phe Ser Asp Val Gly Trp Asn
1               5                   10                  15

Asp Trp Ile Val Ala Pro Pro Gly Tyr His Ala Phe Tyr Cys His Gly
            20                  25                  30

Glu Cys Pro Phe Pro Leu Ala Asp His Leu Asn Ser Thr Asn His Ala
        35                  40                  45

Ile Val Gln Thr Leu Val Asn Ser Val Asn Ser Lys Ile Pro Lys Ala
50                  55                  60

Cys Cys Val Pro Thr Glu Leu Ser Ala Ile Ser Met Leu Tyr Leu Asp
65                  70                  75                  80

Glu Asn Glu Lys Val Val Leu Lys Asn Tyr Gln Asp Met Val Val Glu
                85                  90                  95

Gly Cys Gly Cys Arg
            100
```

```
<210> SEQ ID NO 63
<211> LENGTH: 101
<212> TYPE: PRT
<213> ORGANISM: Homo sapiens

<400> SEQUENCE: 63

Cys Arg Arg His Ser Leu Tyr Val Asp Phe Ser Asp Val Gly Trp Asn
1               5                   10                  15

Asp Trp Ile Val Ala Pro Pro Gly Tyr Gln Ala Phe Tyr Cys His Gly
            20                  25                  30

Asp Cys Pro Phe Pro Leu Ala Asp His Leu Asn Ser Thr Asn His Ala
        35                  40                  45

Ile Val Gln Thr Leu Val Asn Ser Val Asn Ser Ser Ile Pro Lys Ala
    50                  55                  60

Cys Cys Val Pro Thr Glu Leu Ser Ala Ile Ser Met Leu Tyr Leu Asp
65                  70                  75                  80

Glu Tyr Asp Lys Val Val Leu Lys Asn Tyr Gln Glu Met Val Val Glu
                85                  90                  95

Gly Cys Gly Cys Arg
            100

<210> SEQ ID NO 64
<211> LENGTH: 103
<212> TYPE: PRT
<213> ORGANISM: Homo sapiens

<400> SEQUENCE: 64

Cys Ala Arg Arg Tyr Leu Lys Val Asp Phe Ala Asp Ile Gly Trp Ser
1               5                   10                  15

Glu Trp Ile Ile Ser Pro Lys Ser Phe Asp Ala Tyr Tyr Cys Ser Gly
            20                  25                  30

Ala Cys Gln Leu Pro Val Ala Leu Ser Gly Ser Ala Ser Asn His Ala
        35                  40                  45

Thr Ile Gln Ser Ile Val Arg Ala Val Gly Val Val Pro Gly Ile Pro
    50                  55                  60

Glu Pro Cys Cys Val Pro Glu Lys Met Ser Ser Leu Ser Ile Leu Phe
65                  70                  75                  80

Tyr Asp Glu Asn Lys Asn Val Val Leu Lys Val Tyr Pro Asn Met Thr
                85                  90                  95

Val Glu Ser Cys Ala Cys Arg
            100

<210> SEQ ID NO 65
<211> LENGTH: 102
<212> TYPE: PRT
<213> ORGANISM: Xenopus sp.

<400> SEQUENCE: 65

Cys Lys Lys Arg His Leu Tyr Val Glu Phe Lys Asp Val Gly Trp Gln
1               5                   10                  15

Asn Trp Val Ile Ala Pro Gln Gly Tyr Met Ala Asn Tyr Cys Tyr Gly
            20                  25                  30

Glu Cys Pro Tyr Pro Leu Thr Glu Ile Leu Asn Gly Ser Asn His Ala
        35                  40                  45

Ile Leu Gln Thr Leu Val His Ser Ile Glu Pro Glu Asp Ile Pro Leu
    50                  55                  60

Pro Cys Cys Val Pro Thr Lys Met Ser Pro Ile Ser Met Leu Phe Tyr
65                  70                  75                  80
```

```
Asp Asn Asn Asp Asn Val Val Leu Arg His Tyr Glu Asn Met Ala Val
                85                  90                  95
Asp Glu Cys Gly Cys Arg
            100

<210> SEQ ID NO 66
<211> LENGTH: 106
<212> TYPE: PRT
<213> ORGANISM: Mus sp.

<400> SEQUENCE: 66

Cys Arg Ala Arg Arg Leu Tyr Val Ser Phe Arg Glu Val Gly Trp His
  1               5                  10                  15
Arg Trp Val Ile Ala Pro Arg Gly Phe Leu Ala Asn Tyr Cys Gln Gly
             20                  25                  30
Gln Cys Ala Phe Pro Met Pro Lys Ser Leu Lys Gly Gly Pro Pro Pro
         35                  40                  45
Leu Asn His Ala Val Leu Arg Ala Leu Met His Ala Ala Ala Pro Gly
     50                  55                  60
Ala Ala Asp Leu Pro Cys Cys Val Pro Ala Arg Leu Ser Pro Ile Ser
 65                  70                  75                  80
Val Leu Phe Phe Asp Asn Ser Asp Asn Val Val Leu Arg Gln Tyr Glu
                 85                  90                  95
Asp Met Val Val Asp Glu Cys Gly Cys Arg
            100                 105

<210> SEQ ID NO 67
<211> LENGTH: 102
<212> TYPE: PRT
<213> ORGANISM: Drosophila sp.

<400> SEQUENCE: 67

Cys Gln Met Glu Thr Leu Tyr Val Asp Phe Lys Asp Leu Gly Trp His
  1               5                  10                  15
Asp Trp Ile Ile Ala Pro Glu Gly Tyr Gly Ala Phe Tyr Cys Ser Gly
             20                  25                  30
Glu Cys Asn Phe Pro Leu Asn Ala His Met Asn Ala Thr Asn His Ala
         35                  40                  45
Ile Val Gln Thr Leu Val His Leu Leu Glu Pro Lys Lys Val Pro Lys
     50                  55                  60
Pro Cys Cys Ala Pro Thr Arg Leu Gly Ala Leu Pro Val Leu Tyr His
 65                  70                  75                  80
Leu Asn Asp Glu Asn Val Asn Leu Lys Lys Tyr Arg Asn Met Ile Val
                 85                  90                  95
Lys Ser Cys Gly Cys His
            100

<210> SEQ ID NO 68
<211> LENGTH: 4
<212> TYPE: PRT
<213> ORGANISM: Mus sp.

<400> SEQUENCE: 68

Gly Gly Pro Pro
  1
```

We claimed:

1. A method of treating neointimal hyperplasia in a subject suffering therefrom comprising the step of administering to said subject.

2. The method of claim 1, wherein the neointimal hyperplasia is associated with anastomosis.

3. The method of claim 1, wherein the neointimal hyperplasia is induced by chronic kidney disease.

\* \* \* \* \*